US011717558B2

(12) United States Patent
Seehra et al.

(10) Patent No.: US 11,717,558 B2
(45) Date of Patent: Aug. 8, 2023

(54) NUCLEIC ACID MOLECULES ENCODING ACTIVIN RECEPTOR TYPE IIA VARIANTS

(71) Applicant: Keros Therapeutics, Inc., Lexington, MA (US)

(72) Inventors: Jasbir S. Seehra, Lexington, MA (US); Jennifer Lachey, Lincoln, MA (US)

(73) Assignee: Keros Therapeutics, Inc., Lexington, MA (US)

( * ) Notice: Subject to any disclaimer, the term of this patent is extended or adjusted under 35 U.S.C. 154(b) by 158 days.

(21) Appl. No.: 17/327,914

(22) Filed: May 24, 2021

(65) Prior Publication Data

US 2021/0275637 A1 Sep. 9, 2021

Related U.S. Application Data

(62) Division of application No. 16/348,987, filed as application No. PCT/US2017/060960 on Nov. 9, 2017, now Pat. No. 11,013,785.

(60) Provisional application No. 62/531,943, filed on Jul. 13, 2017, provisional application No. 62/420,476, filed on Nov. 10, 2016.

(51) Int. Cl.

*C07H 21/04* (2006.01)
*C12N 15/86* (2006.01)
*C07K 14/71* (2006.01)
*A61K 38/18* (2006.01)
*A61K 47/65* (2017.01)
*A61P 19/08* (2006.01)
*C07K 14/76* (2006.01)
*C12N 15/85* (2006.01)
*C12P 21/02* (2006.01)
*A61K 38/00* (2006.01)
*A61K 47/64* (2017.01)

(52) U.S. Cl.

CPC .............. *A61K 38/18* (2013.01); *A61K 47/65* (2017.08); *A61P 19/08* (2018.01); *C07K 14/71* (2013.01); *C07K 14/76* (2013.01); *C12N 15/85* (2013.01); *C12P 21/02* (2013.01); *A61K 38/00* (2013.01); *A61K 47/64* (2017.08)

(58) Field of Classification Search

None

See application file for complete search history.

(56) References Cited

U.S. PATENT DOCUMENTS 7,612,041 B2 11/2009 Knopf et al.
7,709,605 B2 5/2010 Knopf et al.
7,842,663 B2 11/2010 Knopf et al.
7,947,646 B2 5/2011 Sun et al.
7,951,771 B2 5/2011 Knopf et al.
7,960,343 B2 6/2011 Knopf et al.
7,988,973 B2 8/2011 Sherman
8,007,809 B2 8/2011 Sherman
8,058,229 B2 11/2011 Seehra et al.
8,067,360 B2 11/2011 Knopf et al.
8,067,562 B2 11/2011 Han et al.
8,101,564 B2 1/2012 Choi et al.
8,138,142 B2 3/2012 Seehra et al.
8,173,601 B2 5/2012 Knopf et al.
8,178,488 B2 5/2012 Knopf et al.
8,216,997 B2 7/2012 Seehra et al.
8,252,900 B2 8/2012 Knopf et al.
8,293,881 B2 10/2012 Seehra et al.
8,343,933 B2 1/2013 Knopf et al.
8,361,957 B2 1/2013 Seehra et al.
8,367,611 B2 2/2013 Knopf et al.
8,614,292 B2 12/2013 Han et al.
8,629,109 B2 1/2014 Knopf et al.
8,703,927 B2 4/2014 Seehra et al.
8,710,016 B2 4/2014 Seehra et al.
8,716,459 B2 5/2014 Sun et al.
8,871,209 B2 10/2014 Stitt et al.
8,895,016 B2 11/2014 Sherman et al.
8,999,917 B2 4/2015 Sun et al.
9,138,459 B2 9/2015 Knopf et al.
9,163,075 B2 10/2015 Knopf et al.
9,181,533 B2 11/2015 Seehra et al.

(Continued)

FOREIGN PATENT DOCUMENTS

EP 2314617 A2 4/2011
WO WO-2006/012627 A2 2/2006

(Continued)

OTHER PUBLICATIONS

"A Phase 2 Study of Intravenous or Subcutaneous Dosing of Sotatercept (ACE-011) in Patients With End-Stage Kidney Disease on Hemodialysis," U.S. National Library of Medicine, <clinicaltrials.gov/ct2/show/NCT01999582?term=sotatercept&draw=2&rank=9>, first posted Dec. 3, 2013, retrieved on Mar. 30, 2020 (6 pages).

(Continued)

*Primary Examiner* — Christine J Saoud
*Assistant Examiner* — Jon M Lockard
(74) *Attorney, Agent, or Firm* — Clark & Elbing LLP

(57) ABSTRACT

The invention features polypeptides that include an extracellular ActRIIa variant. In some embodiments, a polypeptide of the invention includes an extracellular ActRIIa variant fused to an Fc domain monomer or moiety. The invention also features pharmaceutical compositions and methods of using the polypeptides to treat diseases and conditions involving weakness and atrophy of muscles, e.g., Duchenne muscular dystrophy, facioscapulohumeral muscular dystrophy, inclusion body myositis, amyotrophic lateral sclerosis, sarcopenia; or cancer cachexia; or metabolic diseases, e.g., obesity, Type-1 diabetes, or Type-2 diabetes.

12 Claims, 11 Drawing Sheets

Specification includes a Sequence Listing.

(56) References Cited

U.S. PATENT DOCUMENTS

| | | | |
|---|---|---|---|
| 9,273,114 | B2 | 3/2016 | Sun et al. |
| 9,284,364 | B2 | 3/2016 | Han et al. |
| 9,353,356 | B2 | 5/2016 | Knopf et al. |
| 9,399,669 | B2 | 7/2016 | Knopf et al. |
| 9,439,945 | B2 | 9/2016 | Seehra et al. |
| 9,447,165 | B2 | 9/2016 | Sun et al. |
| 9,493,556 | B2 | 11/2016 | Seehra et al. |
| 9,505,813 | B2 | 11/2016 | Seehra et al. |
| 9,526,759 | B2 | 12/2016 | Knopf et al. |
| 9,572,865 | B2 | 2/2017 | Knopf et al. |
| 9,610,327 | B2 | 4/2017 | Sun et al. |
| 9,617,319 | B2 | 4/2017 | Seehra et al. |
| 9,745,559 | B2 | 8/2017 | Seehra et al. |
| 9,809,638 | B2 | 11/2017 | Sun et al. |
| 9,850,298 | B2 | 12/2017 | Attie |
| 9,932,379 | B2 | 4/2018 | Seehra et al. |
| 10,093,707 | B2 | 10/2018 | Sherman et al. |
| 10,131,700 | B2 | 11/2018 | Seehra et al. |
| 10,189,882 | B2 | 1/2019 | Attie et al. |
| 10,259,861 | B2 | 4/2019 | Knopf et al. |
| 10,308,704 | B2 | 6/2019 | Sun et al. |
| 10,358,476 | B2 | 7/2019 | Kumar et al. |
| 10,358,633 | B2 | 7/2019 | Seehra et al. |
| 10,377,996 | B2 | 8/2019 | Seehra et al. |
| 10,407,487 | B2 | 9/2019 | Sun et al. |
| 10,487,144 | B2 | 11/2019 | Attie |
| 10,550,170 | B2 | 2/2020 | Sherman et al. |
| 11,013,785 | B2 | 5/2021 | Seehra et al. |
| 11,090,361 | B2 | 8/2021 | Seehra et al. |
| 2006/0068468 | A1 | 3/2006 | Knopf et al. |
| 2009/0005308 | A1 | 1/2009 | Knopf et al. |
| 2010/0267133 | A1 | 10/2010 | Knopf et al. |
| 2010/0316644 | A1 | 12/2010 | Seehra et al. |
| 2011/0038831 | A1 | 2/2011 | Seehra et al. |
| 2011/0092670 | A1 | 4/2011 | Knopf et al. |
| 2011/0135638 | A1 | 6/2011 | Seehra et al. |
| 2011/0250198 | A1 | 10/2011 | Wolfman et al. |
| 2012/0015877 | A1 | 1/2012 | Seehra et al. |
| 2012/0121576 | A1 | 5/2012 | Seehra et al. |
| 2012/0148588 | A1 | 6/2012 | Knopf et al. |
| 2013/0065299 | A1 | 3/2013 | Knopf et al. |
| 2013/0071393 | A1 | 3/2013 | Seehra et al. |
| 2013/0177559 | A1 | 7/2013 | Seehra et al. |
| 2013/0288983 | A1 | 10/2013 | Sun et al. |
| 2013/0315924 | A1 | 11/2013 | Hsu et al. |
| 2014/0079700 | A1 | 3/2014 | Knopf et al. |
| 2014/0314759 | A1 | 10/2014 | Seehra et al. |
| 2015/0023970 | A1 | 1/2015 | Seehra et al. |
| 2015/0030595 | A1 | 1/2015 | Lee et al. |
| 2015/0183845 | A1 | 7/2015 | Sherman et al. |
| 2016/0039922 | A1 | 2/2016 | Attie |
| 2016/0108379 | A1 | 4/2016 | Knopf et al. |
| 2016/0333418 | A1 | 11/2016 | Haqq |
| 2017/0058016 | A1 | 3/2017 | Knopf et al. |
| 2017/0327800 | A1 | 11/2017 | Seehra et al. |
| 2017/0360887 | A1 | 12/2017 | Attie et al. |
| 2018/0125928 | A1 | 5/2018 | Attie et al. |
| 2018/0148491 | A1 | 5/2018 | Han et al. |
| 2018/0161426 | A1 | 6/2018 | Cappellini et al. |
| 2018/0334673 | A1 | 11/2018 | Wood et al. |
| 2019/0085067 | A1 | 3/2019 | Schurpf et al. |
| 2019/0151463 | A1 | 5/2019 | Gegg et al. |
| 2019/0233486 | A1 | 8/2019 | Attie et al. |
| 2019/0256605 | A1 | 8/2019 | Han et al. |
| 2019/0282663 | A1 | 9/2019 | Seehra et al. |
| 2019/0284251 | A1 | 9/2019 | Seehra et al. |
| 2019/0330307 | A1 | 10/2019 | Han et al. |
| 2019/0352619 | A1 | 11/2019 | Knopf et al. |
| 2020/0055919 | A1 | 2/2020 | Kumar et al. |
| 2020/0071381 | A1 | 3/2020 | Knopf et al. |
| 2020/0407415 | A1 | 12/2020 | Seehra et al. |
| 2021/0030841 | A1 | 2/2021 | Lachey et al. |
| 2021/0052698 | A1 | 2/2021 | Seehra et al. |

FOREIGN PATENT DOCUMENTS

| | | | |
|---|---|---|---|
| WO | WO-2006/012627 | A3 | 2/2006 |
| WO | WO-2008/094708 | A2 | 8/2008 |
| WO | WO-2008/100384 | A2 | 8/2008 |
| WO | WO-2009/015345 | A1 | 1/2009 |
| WO | WO-2009/158015 | A3 | 12/2009 |
| WO | WO-2009/158025 | A2 | 12/2009 |
| WO | WO-2009/158035 | A2 | 12/2009 |
| WO | WO-2010/062383 | A2 | 6/2010 |
| WO | WO-2010/083034 | A1 | 7/2010 |
| WO | WO-2010/151426 | A1 | 12/2010 |
| WO | WO-2011/020045 | A1 | 2/2011 |
| WO | WO-2011/031901 | A1 | 3/2011 |
| WO | WO-2011/056896 | A1 | 5/2011 |
| WO | WO-2011/063018 | A1 | 5/2011 |
| WO | WO-2013/059347 | A1 | 4/2013 |
| WO | WO-2013/188448 | A3 | 12/2013 |
| WO | WO-2014/138485 | A1 | 9/2014 |
| WO | WO-2014/144903 | A1 | 9/2014 |
| WO | WO-2015/143403 | A1 | 9/2015 |
| WO | WO-2015/161220 | A1 | 10/2015 |
| WO | WO-2015/192111 | A1 | 12/2015 |
| WO | WO-2015/192127 | A2 | 12/2015 |
| WO | WO-2016/090188 | A1 | 6/2016 |
| WO | WO-2016/164501 | A1 | 10/2016 |
| WO | WO-2016/171948 | A1 | 10/2016 |
| WO | WO-2016/187378 | A1 | 11/2016 |
| WO | WO-2017/079591 | A2 | 5/2017 |
| WO | WO-2017/091706 | A1 | 6/2017 |
| WO | WO-2017/147182 | A1 | 8/2017 |
| WO | WO-2018/013936 | A1 | 1/2018 |
| WO | WO-2018/022762 | A1 | 2/2018 |
| WO | WO-2018/067740 | A1 | 4/2018 |
| WO | WO-2018/067874 | A1 | 4/2018 |
| WO | WO-2018/089706 | A2 | 5/2018 |
| WO | WO-2018/089715 | A1 | 5/2018 |
| WO | WO-2018/100483 | A1 | 6/2018 |
| WO | WO-2018/144542 | A1 | 8/2018 |
| WO | WO-2018/144968 | A1 | 8/2018 |
| WO | WO-2019/094751 | A1 | 5/2019 |
| WO | WO-2019/140283 | A1 | 7/2019 |
| WO | WO-2019/217715 | A1 | 11/2019 |
| WO | WO-2021/189006 | A1 | 9/2021 |
| WO | WO-2021/189010 | A1 | 9/2021 |
| WO | WO-2021/189019 | A1 | 9/2021 |

OTHER PUBLICATIONS

"A Phase IIa Study of Sotatercept on Bone Mass and Turnover in Patients With Multiple Myeloma," U.S. National Library of Medicine, <clinicaltrials.gov/ct2/show/NCT02230917?term=sotatercept&draw=2&rank=4>, first posted Sep. 3, 2014, retrieved Mar. 30, 2020 (7 pages).

"A Study of Sotatercept for the Treatment of Pulmonary Arterial Hypertension (PAH) (Pulsar)," U.S. National Library of Medicine, <clinicaltrials.gov/ct2/show/NCT03496207?term=sotatercept&draw=2&rank=3>, first posted Apr. 12, 2018, retrieved Mar. 30, 2020 (8 pages).

"A Study of Sotatercept for the Treatment of Pulmonary Arterial Hypertension (Spectra)," U.S. National Library of Medicine, <clinicaltrials.gov/ct2/show/NCT03738150?term=sotatercept&draw=2&rank=1>, first posted Nov. 13, 2018, retrieved on Mar. 30, 2020 (9 pages).

"Efficacy and Safety Study of Luspatercept (ACE-536) Versus Epoetin Alfa for the Treatment of Anemia Due to IPSS-R Very Low, Low or Intermediate Risk Myelodysplastic Syndromes (MDS) in ESA Naïve Subjects Who Require Red Blood Cell Transfusions (Commands)," U.S. National Library of Medicine, <clinicaltrials.gov/ct2/show/NCT03682536?term=luspatercept&draw=2&rank=10>, first posted Sep. 24, 2018, retrieved Mar. 30, 2020 (13 pages).

"Safety and Efficacy Study of Sotatercept in Adults With Transfusion Dependent Diamond Blackfan Anemia (ACE-011-DBA)," U.S. National Library of Medicine, <clinicaltrials.gov/ct2/show/NCT01464164?term=sotatercept&draw=2&rank=2>, first posted Nov. 3, 2011, retrieved Mar. 30, 2020 (10 pages).

(56) References Cited

OTHER PUBLICATIONS

"Sotatercept in Treating Patients With Myeloproliferative Neoplasm-Associated Myelofibrosis or Anemia," U.S. National Library of Medicine, <clinicaltrials.gov/ct2/show/NCT01712308?term=sotatercept&draw=2&rank=8>, first posted Oct. 23, 2012, retrieved Mar. 30, 2020 (7 pages).
"Study of ACE-536 for the Treatment of Anemia in Patients With Myelodysplastic Syndromes (MDS)," U.S. National Library of Medicine, <clinicaltrials.gov/ct2/show/NCT01749514?term=luspatercept&draw=2&rank=12>, first posted Dec. 13, 2012, retrieved Mar. 30, 2020 (8 pages).
"Study of ACE-536 in Healthy Postmenopausal Women," U.S. National Library of Medicine, <clinicaltrials.gov/ct2/show/NCT01432717?term=luspatercept&draw=2&rank=13>, first posted Sep. 13, 2011, retrieved Mar. 30, 2020 (5 pages).
"Study of Sotatercept for the Treatment of Anemia in low-or Intermediate-1 Risk Myelodysplastic Syndromes (MDS) or Non-proliferative Chronic Myelomonocytic Leukemia (CMML)," U.S. National Library of Medicine, <clinicaltrials.gov/ct2/show/NCT01736683?term=sotatercept&draw=2&rank=5>, first posted Nov. 29, 2012, retrieved Mar. 30, 2020 (12 pages).
"Study to Evaluate Effect of a Single Dose of Sotatercept (ACE-011) on Red Blood Cell Mass and Plasma Volume in Subjects With Solid Tumors," U.S. National Library of Medicine, <clinicaltrials.gov/ct2/show/NCT01190644?term=sotatercept&draw=2&rank=7>, first posted Aug. 27, 2010, retrieved Mar. 30, 2020 (6 pages).
"Study to Evaluate the Effects of ACE-536 in Patients With Beta-thalassemia," U.S. National Library of Medicine, <clinicaltrials.gov/ct2/show/NCT01749540?term=luspatercept&draw=2&rank=11>, first posted Dec. 13, 2012, retrieved Mar. 30, 2020 (8 pages).
"To Determine Safe and Effective Dose of ACE-011 for the Treatment of Chemotherapy Induced Anemia in Patients With Advanced Non-small Cell Lung Cancer," U.S. National Library of Medicine,<clinicaltrials.gov/ct2/show/NCT01284348?term=sotatercept&draw=2&rank=6>, first posted Jan. 27, 2011, retrieved Mar. 30, 2020 (10 pages).
"To Document the Burden of Illness on the Quality of Life and the Impact on Healthcare Utilization in (Beta)-thalassemia Subjects Who Are Transfusion Dependent (TD) and Non-transfusion Dependent (NTD) Receiving Standard of Care," U.S. National Library of Medicine, <clinicaltrials.gov/ct2/show/NCT02626689?term=luspatercept&draw=2&rank=14>, first posted Dec. 10, 2015, retrieved Mar. 30, 2020 (9 pages).
Abdulkadyrov et al., "Sotatercept in Patients with Osteolytic Lesions of Multiple Myeloma," Br J Haematol. 165(6):814-823 (2014).
Akpan et al., "The effects of a soluble activin type IIB receptor on obesity and insulin sensitivity," available in PMC May 1, 2010, published in final edited form as: Int J Obes (Lond). 33(11):1265-73 (2009) (17 pages).
Attie et al., "A phase 1 study of ACE-536, a regulator of erythroid differentiation, in healthy volunteers," Am J Hematol. 89(7): 766-770 (2014) (5 pages).
Attie et al., "A single ascending-dose study of muscle regulator ACE-031 in healthy volunteers." Muscle Nerve. 47(3):416-23 (2013).
Badesch et al., "Pulsar: A Phase 2, Randomized, Double-Blind, Placebo-Controlled Study to Assess the Efficacy and Safety of Sotatercept (ACE-011) When Added to Standard of Care for the Treatment of Pulmonary Arterial Hypertension (PAH)," ERS International Congress Sep. 28-Oct. 2, 2019, Madrid, Spain, Poster PA4750, Abstract 19918, retrieved from <acceleronpharma.com/wp-content/uploads/2019/10/Badesch-et-al-ERS-2019-PULSAR-TIP-Poster_FINAL-2.pdf> (2019) (1 page).
Bernstein et al., "Activin Decoy Receptor ActRIIB:Fc Lowers FSH and Therapeutically Restores Oocyte Yield, Prevents Oocyte Chromosome Misalignments and Spindle Aberrations, and Increases Fertility in Midlife Female SAMP8 Mice," Endocrinology. 157(3):1234-47 (2016).
Bond et al., "Modeling Energy Dynamics in Mice with Skeletal Muscle Hypertrophy Fed High Calorie Diets," Int J Biol Sci. 12(5):617-30 (2016).
Cadena et al., "Administration of a soluble activin type IIB receptor promotes skeletal muscle growth independent of fiber type," J Appl Physiol. 109(3):635-642 (2010).
Campbell et al., "Myostatin inhibitor ACE-031 treatment of ambulatory boys with Duchenne muscular dystrophy: Results of a randomized, placebo-controlled clinical trial," Muscle Nerve. 55(4):458-464 (2017).
Cappellini et al., "A Phase 2a, Open-Label, Dose-Finding Study to Determine the Safety and Tolerability of Sotatercept (ACE-011) in Adults With Beta-Thalassemia: Interim Results," 55th Annual Meeting of the American Society of Hematology (ASH), Dec. 7-10, New Orleans, LA, Poster 3448 (2013).
Cappellini et al., "The Believe Trial: Results of a Phase 3, Randomized, Double-Blind, Placebo-Controlled Study of Luspatercept in Adult Beta-Thalassemia Patients Who Require Regular Red Blood Cell (RBC) Transfusions," 60th Annual Meeting of the American Society of Hematology (ASH), Dec. 1-4, San Diego CA, Oral Presentation, retrieved from <http://acceleronpharma.com/wp-content/uploads/2018/12/BELIEVE-ASH-2018-Oral-Presentation-for-upload.pdf> (2018) (17 pages).
Carlson et al., "Soluble Activin Receptor Type IIB Increases Forward Pulling Tension in the MDX Mouse," available in PMC May 1, 2012, published in final edited form as: Muscle Nerve. 43(5):694-699 (2011) (11 pages).
Carrancio et al., "An activin receptor IIA ligand trap promotes erythropoiesis resulting in a rapid induction of red blood cells and haemoglobin," Br J Haematol. 165(6):870-882 (2014).
Cash et al., "The structure of myostatin:follistatin 288: insights into receptor utilization and heparin binding," EMBO J. 28(17):2662-76 (2009).
Chantry et al., "Inhibiting activin-A signaling stimulates bone formation and prevents cancer-induced bone destruction in vivo." J Bone Miner Res. 25(12):2633-46 (2010).
Chen et al., "Pharmacokinetics and Exposure-Response of Luspatercept in Patients With Anemia Due to Low- or Intermediate-1-Risk Myelodysplastic Syndromes (MDS): Preliminary Results From Phase 2 Studies," 58th Annual Meeting of the American Society of Hematology (ASH), Dec. 3-6, San Diego, California, Poster 1990, retrieved from <acceleronpharma.com/wp-content/uploads/2017/03/Chen-ASH-2016-Poster-Luspatercept-PK-MDS.pdf>, (2016) (1 page).
Chen et al., "Pharmacokinetics and Exposure-Response of Luspatercept in Patients With Beta-Thalassemia: Preliminary Results From Phase 2 Studies," 58th Annual Meeting of the American Society of Hematology (ASH), Dec. 3-6, San Diego, CA, Poster 2463, retrieved from <acceleronpharma.com/wp-content/uploads/2017/03/20161204-Chen-ASH-2016-Poster-Luspatercept-PK-B-thal.pdf>, (2016) (1 page).
Dellanna, "Safety and Hemoglobin Effect of Sotatercept, Administered Intravenously and Subcutaneously, for Maintenance of Hemoglobin in Hemodialysis Subjects: Interim Analysis of a Phase 2 Study," 48th Annual American Society of Nephrology Kidney Week, Nov. 3-8, San Diego, CA, retrieved from <acceleronpharma.com/wp-content/uploads/2017/03/20151106-ASN-2015_Sotatercept-REN-002-Oral-Presentation_10-22-15-v3-Final.pdf>, (2015) (14 pages).
DiGirolamo et al., "Administration of soluble activin receptor 2B increases bone and muscle mass in a mouse model of osteogenesis imperfecta," Bone Res. 3:14042 (2015) (6 pages).
Dussiot et al., "An activin receptor IIA ligand trap corrects ineffective erythropoiesis in beta-thalassemia," Nat Med. 20(4):398-407 (2014) (12 pages).
El-Shahawy et al., "Interim Analysis of ACE-011-REN-001: The First 28 Day Dose Cycle of Low and Medium Starting Doses of Sotatercept Compared to Placebo for Correction of Anemia in Hemodialysis Subjects," National Kidney Foundation (NKF) 2014 Spring Clinical Meeting, Apr. 22-26, Las Vegas, NV, retrieved from <acceleronpharma.com/wp-content/uploads/2017/03/20140423-NKF-2014_REN-001-Interim-Analysis-Poster_FINAL.pdf>, (2014) (7 pages).
El-Shahawy et al., "Long-term Effects of Sotatercept Compared With Placebo for Correction of Anemia in Hemodialysis Subjects: Interim Analysis of ACE-011-REN-001 Phase 2A Study," 51st Congress of the European Renal Association and European Dialysis and Transplant Association, May 31-Jun. 3, Amsterdam, Poster SP244, retrieved from <acceleronpharma.com/wp-content/uploads/

(56) References Cited

OTHER PUBLICATIONS

2014/06/20140601-Long-Term-Effects-of-Sotatercept-Compared-with-Placebo-for-Correction-of-Anemia.pdf>, (2014) (7 pages).
El-Shahawy et al., "Safety and Hemoglobin Effect of the First 28-Day Dose Cycle of Sotatercept 0.7 mg/kg Compared With Lower Doses and Placebo for Correction of Anemia in Hemodialysis Subjects: Interim Analysis," American Society of Nephrology Kidney Week 2014, Nov. 11-16, Philadelphia, PA. Poster, retrieved from <acceleronpharma.com/wp-content/uploads/2014/11/20141113-El-Shahawy-ASN-2014-Sotatercept-Safety-Poster.pdf>, (2014) (1 page).
Fajardo et al., "Treatment with a soluble receptor for activin improves bone mass and structure in the axial and appendicular skeleton of female cynomolgus macaques (*Macaca fascicularis*)," Bone. 46(1):64-71 (2010).
Fakhfakh et al., "Administration of a soluble activin type IIB receptor promotes the transplantation of human myoblasts in dystrophic mice," available in PMC Jul. 10, 2014, published in final edited form as: Cell Transplant. 21(7):1419-30 (2012) (19 pages).
Fenaux et al., "Assessment of Longer-Term Efficacy and Safety in the Phase 3, Randomized, Double-Blind, Placebo-Controlled Medalist Trial of Luspatercept to Treat Anemia in IPSS-R Very Low-, Low-, or Int-Risk RBC Transfusion-Dependent MDS with Ring Sideroblasts," 61st Annual Meeting of the American Society of Hematology (ASH), Dec. 7-10, Orlando, Florida, retrieved from <acceleronpharma.com/wp-content/uploads/2019/12/ASH-2019-MEDALIST-long-term-analysis-Fenaux-oral-7-Dec-2019V2.pdf>, (2019) (18 pages).
Fenaux et al., "Luspatercept in Patients with Lower-Risk Myelodysplastic Syndromes," N Engl J Med. 382(2):140-151 (2020).
Fenaux et al., "The MEDALIST Trial: Results of a Phase 3, Randomized, Double-Blind, Placebo-Controlled Study of Luspatercept to Treat Patients With Very Low-, Low-, or Intermediate-Risk Myelodysplastic Syndromes (MDS) Associated Anemia With Ring Sideroblasts (RS) Who Require Red Blood Cell (RBC) Transfusions," 60th Annual Meeting of the American Society of Hematology (ASH), Dec. 1-4, San Diego, California, Oral Presentation (2018) (18 pages).
Fields et al., "Activin receptor antagonists for cancer-related anemia and bone disease," Exp Opin Invest Drugs. 22(1):87-101 (2013).
Garcia-Manero et al., "Hematologic Improvement-Neutrophil and -Platelet in the Medalist Trial: Multilineage Data from a Phase 3, Randomized, Double-Blind, Placebo-Controlled Study of Luspatercept to Treat Anemia in Patients with Very Low-, Low-, or Intermediate-Risk Myelodysplastic Syndromes with Ring Sideroblasts Who Require Red Blood Cell (RBC) Transfusions," 61st Annual Meeting of the American Society of Hematology (ASH), Dec. 7-10, Orlando, Florida, Abstract 4243 (2019).
Gerds et al., "A Phase 2 Study of Luspatercept in Patients With Myelofibrosis-Associated Anemia," 61st Annual Meeting of the American Society of Hematology (ASH), Dec. 7-10, Orlando FL, Presentation, Abstract 557, retrieved from <acceleronpharma.com/wp-content/uploads/2019/12/Gerds-et-al.-Luspatercept-in-MF_ASH-2019-7-Dec-2019-FINAL-FOR-UPLOAD.pdf>, (2019) (13 pages).
Giagounidis et al., "Luspatercept Increases Hemoglobin and Reduces Transfusion Burden in Patients With Lower-Risk Myelodysplastic Syndromes (MDS): Long-Term Results From the Phase 2 PACE-MDS Study," 22nd European Hematology Association Congress, Jun. 22-25, Madrid, Spain, Abstract P666, retrieved from <acceleronpharma.com/wp-content/uploads/2017/06/EHA-2017-MDS-Poster-20Jun2017-FINAL.pdf>, (2017) (1 page).
Giagounidis et al., "Luspatercept Treatment Leads to Long Term Increases in Hemoglobin and Reductions in Transfusion Burden in Patients with Low or Intermediate-1 Risk Myelodysplastic Syndromes (MDS): Preliminary Results from the Phase 2 PACE-MDS Extension Study," Presentation. (2015) (16 pages).
Goh et al., "Activin receptor type 2A (ACVR2A) functions directly in osteoblasts as a negative regulator of bone mass," J Biol Chem. 292(33):13809-13822 (2017).
Graham et al., "A Soluble Activin Receptor IIB Fails to Prevent Muscle Atrophy in a Mouse Model of Spinal Cord Injury," J Neurotrauma. 33(12):1128-1135 (2016).
Guo et al., "Myostatin inhibition in muscle, but not adipose tissue, decreases fat mass and improves insulin sensitivity," PLoS One. 4(3):e4937 (2009) (11 pages).
Guo et al., "Myostatin inhibition prevents diabetes and hyperphagia in a mouse model of lipodystrophy," Diabetes. 61(10):2414-23 (2012).
Havill et al., "Sotatercept Improves Anemia, Vascular Calcification, and Bone Loss in Patients With End-Stage Kidney Disease on Hemodialysis," American Society of Nephrology Kidney Week Nov. 5-8, 2015, San Diego, CA, Poster TH-P0038, retrieved from <acceleronpharma.com/wp-content/uploads/2017/03/20151105-ASN-2015_Sotatercept-REN-001-Poster_10.20.15-Final-1.pdf>, (2015) (1 page).
International Search Report and Written Opinion for International Application No. PCT/US17/60960, dated Aug. 9, 2018 (14 pages).
International Search Report and Written Opinion for International Application No. PCT/US17/60970, dated Mar. 27, 2018 (15 pages).
International Search Report and Written Opinion for International Application No. PCT/US2018/060076, dated Mar. 14, 2019 (18 pages).
International Search Report and Written Opinion for International Application No. PCT/US2019/013329, dated May 13, 2019 (19 pages).
International Search Report and Written Opinion for International Application No. PCT/US2019/031573, dated Sep. 17, 2019 (16 pages).
Joshi et al., "ActRIIA-Fc (Sotatercept) Reverses Pulmonary Vascular Remodeling to Attenuate Pulmonary Arterial Hypertension by Rebalancing Activin/BMP Signaling in a Preclinical Model," American Thoracic Society 2019 International Conference, May 17-22, Dallas, TX, Poster, retrieved from <acceleronpharma.com/wp-content/uploads/2019/06/Joshi-SR-et-al-ATS-2019-Poster-Sotatercept-Reverses-Pulmonary-Vascular-R...-1.pdf>, (2019) (1 page).
Joshi et al., "RAP-011, a Murine Ortholog of ACTRIIA-FC (Sotatercept), Improves Pulmonary Hemodynamics and Restores Right Ventricular Structure and Function in a Preclinical Model of Severe Angio-obliterative Pulmonary Arterial Hypertension," American Heart Association Scientific Session, Nov. 10-12, Chicago, Illinois, retrieved from <http://acceleronpharma.com/wp-content/uploads/2018/11/SRJ-AHA-2018-Poster.pdf>, (2018) (1 page).
"Keros Therapeutics Presents Results from Preclinical Studies Investigating KER-012 at the American Society for Bone and Mineral Research 2020 Annual Meeting," Keros Therapeutics, <https://www.globenewswire.com/news-release/2020/09/11/2092586/0/en/Keros-Therapeutics-Presents-Results-from-Preclinical-Studies-Investigating-KER-012-at-the-American-Society-for-Bone-and-Mineral-Research-2020-Annual-Meeting.html>, dated Sep. 11, 2020, retrieved on Feb. 25, 2021 (4 pages).
Komrokji et al., "A Phase 2, Dose-Finding Study of Sotatercept (ACE-011) in Patients with Lower-Risk Myelodysplastic Syndromes or Non-Proliferative Chronic Myelomonocytic Leukemia and Anemia Requiring Transfusion," The 13th International Symposium on Myelodysplastic Syndromes, Apr. 29-May 2, Washington, D.C., retrieved from <http://acceleronpharma.com/wp-content/uploads/2017/03/20150429-Komrokji-MDS-001_MDSF-2015-presentation_29-April-2015_FINAL.pdf>, (2015) (21 pages).
Komrokji et al., "An Open-Label, Phase 2, Dose-Finding Study of Sotatercept (ACE-011) in Patients with Low or Intermediate (Int)-1-Risk Myelodysplastic Syndromes (MDS) or Non-Proliferative Chronic Myelomonocytic Leukemia (CMML) and Anemia Requiring Transfusion," 56th Annual Meeting of the American Society of Hematology (ASH), Dec. 6-9, San Francisco, California. Poster P3251 (2014).
Lee et al., "Growth differentiation factor 11 signaling controls retinoic acid activity for axial vertebral development," available in PMC Nov. 1, 2011, published in final edited form as: Dev Biol. 347(1):195-203 (2010) (19 pages).
Lee et al., "Myostatin and the control of skeletal muscle mass," Curr Opin Genet Devel. 9(5):604-607 (1999).

(56) References Cited

OTHER PUBLICATIONS

Lee et al., “Regulation of muscle growth by multiple ligands signaling through activin type II receptors,” Proc Natl Acad Sci U S A. 102(50):18117-18122 (2005).
Lee et al., “Regulation of myostatin activity and muscle growth,” Proc Natl Acad Sci U S A. 98(16):9306-9311 (2001).
Lee et al., “Role of satellite cells versus myofibers in muscle hypertrophy induced by inhibition of the myostatin/activin signaling pathway,” Proc Natl Acad Sci U S A. 109(35):E2353-60 (2012).
Lotinun et al., “A soluble activin receptor Type IIA fusion protein (ACE-011) increases bone mass via a dual anabolic-antiresorptive effect in Cynomolgus monkeys.” Bone. 46(4):1082-8 (2010).
MacDonald et al., “Denervation atrophy is independent from Akt and mTOR activation and is not rescued by myostatin inhibition,” first posted online on Feb. 6, 2014, published in final edited form as: Dis Model Mech. 7(4):471-81 (2014) (Author manuscript) (39 pages).
Malluche et al., “Sotatercept: Initial Signal-Seeking Quantitative Computed Tomography Results for Bone Mass and Vascular Calcification in Hemodialysis Subjects Treated With Escalating Doses: Interim Analysis of ACE-011-REN-001,” American Society of Nephrology Kidney Week 2014, Nov. 11-16, Philadelphia, PA, retrieved from <http://acceleronpharma.com/wp-content/uploads/2017/03/20141113-Malluche_ASN-2014_Sotatercept-Bone-Mass-VC-Poster_11-10-14-Final.pdf>, (2014) (1 page).
Malluche et al., “The Role of Activin Signaling in the Pathogenesis of Renal Osteodystrophy of CKD-MBD,” 52nd ERA-EDTA Congress, May 28-31, London, United Kingdom, Poster FP406, retrieved from <acceleronpharma.com/wp-content/uploads/2017/03/20150529-ERA-2015_RAP-011-Bone-Histomorphometry-Poster_05.22.15-Final-for-QR-Code.pdf>, (2015) (1 page).
Marisavljevic et al., “Myelofibrosis in primary myelodysplastic syndromes: clinical and biological significance,” Med Oncol. 21(4):325-31 (2004) (Abstract only).
Martinez, “Luspatercept Inhibits pSmad2/3 Signaling and Promotes Erythroid Maturation Through a GATA1 Dependent Mechanism,” 23rd European Hematology Association Congress, Jun. 14-17, Stockholm, Sweden, Oral Presentation, retrieved from <acceleronpharma.com/wp-content/uploads/2018/06/EHA2018PMFinal.pdf>, (2018) (25 pages).
Martinez, “RAP-536 (Murine ACE-536/Luspatercept) Inhibits Smad2/3 Signaling and Promotes Erythroid Differentiation by Restoring GATA1 Function in Murine Beta-thalassemia,” 21st European Hematology Association Congress, Jun. 9-12, Copenhagen, Denmark, Oral Presentation, retrieved from <acceleronpharma.com/wp-content/uploads/2017/03/20160610-PedroEHA2016Final.pdf> (2016) (23 pages).
Martinez, “RAP-536 (Murine ACE-536/Luspatercept) Inhibits Smad2/3 Signaling and Promotes Erythroid Differentiation by Restoring GATA1 Function in Murine Beta-thalassemia,” Oral Presentation, Blood. 126(23):751 (2015) (25 pages).
McPherron et al., “Double muscling in cattle due to mutations in the myostatin gene,” Proc Natl Acad Sci USA. 94(23):12457-61 (1997).
McPherron et al., “GDF-3 and GDF-9: two new members of the transforming growth factor-beta superfamily containing a novel pattern of cysteines,” J Biol Chem. 268(5):3444-3449 (1993) (7 pages).
McPherron et al., “Redundancy of myostatin and growth/differentiation factor 11 function,” BMC Dev Biol. 9:24 (2009) (9 pages).
McPherron et al., “Regulation of anterior/posterior patterning of the axial skeleton by growth/differentiation factor 11,” Nat Genet. 22(3):260-264 (1999).
McPherron et al., “Regulation of skeletal muscle mass in mice by a new TGF-beta superfamily member,” Nature. 387(6628):83-90 (1997).
McPherron et al., “Soluble activin receptor type IIB treatment does not cause fat loss in mice with diet-induced obesity,” available in PMC Mar. 1, 2013, published in final edited form as: Diabetes Obes Metab. 14(3):279-82 (2012) (6 pages).
McPherron et al., “Suppression of body fat accumulation in myostatin-deficient mice,” J Clin Invest. 109(5):595-601 (2002).
McPherron et al., “The transforming growth factor beta superfamily,” Growth Factors and Cytokines in Health and Disease. 1:357-393 (1996).
Mesa et al., “A Phase 2, Multicenter, Open-Label Study of the Safety and Efficacy of Luspatercept in Subjects With Myeloproliferative Neoplasm (MPN)-Associated Myelofibrosis and Anemia With or Without RBC Transfusion Dependence,” American Society of Clinical Oncology (ASCO) Annual Meeting, Jun. 1-5, Chicago Illinois, Poster TPS7083, retrieved from <http://acceleronpharma.com/wp-content/uploads/2018/06/Mesa-MF-TiP-ASCO-2018-Poster-May-24-2018_FINAL-1.pdf>, (2018) (1 page).
Morgenroth et al., “Insights into bone health in Duchenne muscular dystrophy,” Bonekey Rep. 1(9):1-11 (2012).
Morine et al., “Activin IIB receptor blockade attenuates dystrophic pathology in a mouse model of Duchenne muscular dystrophy,” available in PMC Jul. 17, 2015, published in final edited form as: Muscle Nerve. 42(5):722-30 (2010) (17 pages).
Nagy et al., “Electrical impedance myography as a biomarker of myostatin inhibition with ActRIIB-mFc: a study in wild-type mice,” Future Sci OA. 04(06):FSO308 (2018) (10 pages).
Ngo et al. *Computational Complexity, Protein Structure Prediction, and the Levinthal Paradox*. Birkhäuser Boston, 491 (1994).
Nielsen et al., “Postnatal Hyperplasic Effects of ActRIIB Blockade in a Severely Dystrophic Muscle,” J Cell Physiol. 232(7):1774-1793 (2016) (21 pages).
Paulson, “Targeting a new regulator of erythropoiesis to alleviate anemia,” Nat Med. 20(4):334-335 (2014).
Pearsall et al., “A soluble activin type IIA receptor induces bone formation and improves skeletal integrity,” Proc Nat Acad Sci U S A. 105(19):7082-7087 (2008).
Piga et al., “Improvements in Hemoglobin, Quality of Life, and Six-Minute-Walk Distance in Adults with beta-Thalassemia Treated with Luspatercept: Long-Term Phase 2 Study,” 23rd European Hematology Association Congress, Jun. 14-17, Stockholm, Sweden, Oral Presentation, retrieved from <acceleronpharma.com/wp-content/uploads/2018/06/Piga-et-al-EHA-2018-Presentation-Improvements-in-Hemoglobin-Quality-of-Life-and-Six-Minute-Walk-Distance.pdf>, (2018) (22 pages).
Piga et al., “Luspatercept (ACE-536) Increases Hemoglobin and Decreases Transfusion Burden and Liver Iron Concentration in Adults with Beta-Thalassemia: Preliminary Results from a Phase 2 Study,” EHA (2015) (22 pages).
Piga et al., “Luspatercept (ACE-536) Increases Hemoglobin and Decreases Transfusion Burden and Serum Ferritin in Adults with Beta-Thalassemia: Preliminary Results from a Phase 2 Study,” American Society of Hematology, Oral Presentation, dated Dec. 7, 2014 (21 pages).
Piga et al., “Luspatercept Decreases Transfusion Burden and Liver Iron Concentration in Regularly Transfused Adults with Beta-Thalassemia,” 21st European Hematology Association Congress, Jun. 9-12, Copenhagen, Denmark, Presentation, retrieved from <acceleronpharma.com/wp-content/uploads/2017/03/20160612-EHA-2016-Luspatercept-Thal-TD-FINAL.pdf>, (2016) (15 pages).
Piga et al., “Luspatercept improves hemoglobin levels and blood transfusion requirements in a study of patients with beta-thalassemia,” Blood. 133(12):1279-1289 (2019).
Piga et al., “Luspatercept Increases Hemoglobin and Reduces Transfusion Burden in Patients with Low-Intermediate Risk Myelodysplastic Syndromes (MDS): Long-Term Results From Phase 2 PACE-MDS Study,” 21st European Hematology Association Congress, Jun. 9-12, Copenhagen, Denmark, Presentation, retrieved from <http://acceleronpharma.com/wp-content/uploads/2017/03/20160610-EHA-2016-Luspatercept-MDS-FINAL.pdf> (2016) (16 pages).
Piga et al., “Luspatercept Increases Hemoglobin, Decreases Transfusion Burden, and Improves Patient-Reported Outcomes in Adults with Beta-Thalassemia,” 58th Annual Meeting of the American Society of Hematology (ASH), Dec. 3-6, San Diego, California, Oral Presentation, retrieved from <http://acceleronpharma.com/wp-content/uploads/2017/03/20161205-Luspatercept-Increases-Hemoglobin.pdf>, (2016) (21 pages).

(56) References Cited

OTHER PUBLICATIONS

Piga et al., "Luspatercept Increases Hemoglobin, Reduces Liver Iron Concentration and Improves Quality of Life in Non-Transfusion Dependent Adults with Beta-Thalassemia," 21st European Hematology Association Congress, Jun. 9-12, Copenhagen, Denmark, Abstract P758, retrieved from <http://acceleronpharma.com/wp-content/uploads/2017/03/20160611-EHA-2016-Luspatercept-BThal-NTD-poster-FINAL.pdf>, (2016) (1 page).

Piga et al., "Luspatercept Increases Hemoglobin, Reduces Liver Iron Concentration and Improves Quality of Life in Non-Transfusion Dependent Adults with Beta-Thalassemia," 2nd MEGMA Conference, Nov. 11-12, Amman, Jordan, retrieved from <http://acceleronpharma.com/wp-content/uploads/2017/03/20161111-TIF-2016-Luspatercept-BThal-NTD-poster_FINAL_16-10-31.pdf>, (2016) (1 page).

Platzbecker et al., "Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study," 57th American Society of Hematology Annual Meeting and Exposition, Dec. 5-8, Orlando, FL, Abstract 2862, retrieved from <Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study>, (2015) (1 page).

Platzbecker et al., "Luspatercept (ACE-536) Increases Hemoglobin and Reduces Transfusion Burden in Patients with Low or Intermediate-1 Risk Myelodysplastic Syndromes (MDS): Preliminary Results from a Phase 2 Study," American Society of Hematology, Oral Presentation (2014) (21 pages).

Platzbecker et al., "Luspatercept for the treatment of anaemia in patients with lower-risk myelodysplastic syndromes (PACE-MDS): a multicentre, open-label phase 2 dose-finding study with long-term extension study," Lancet Oncol. 18(10):P1338-1347 (2017).

Platzbecker et al., "Luspatercept Increases Hemoglobin and Reduces Transfusion Burden in Patients With Low or Intermediate-1 Risk Myelodysplastic Syndromes (MDS): Preliminary Results From a Phase 2 Study," EHA MDS Oral Presentation, Jun. 13, 2015 (16 pages).

Platzbecker et al., "Luspatercept Increases Hemoglobin and Reduces Transfusion Burden in Patients With Low or Intermediate-1 Risk Myelodysplastic Syndromes (MDS): Preliminary Results From a Phase 2 Study," Advancing Research & Patient Care, The 13th International Symposium on Myelodyplastic Syndromes, Washington, D.C., Apr. 19-May 2, 2015 (15 pages).

Platzbecker et al., "Luspatercept Response in New Subpopulations of Patients With Lower-Risk Myelodysplastic Syndromes (MDS): Update of the PACE Study," 14th International Symposium on Myelodysplastic Syndromes, May 3-6, Valencia, Spain, Oral Presentation, retrieved from <acceleronpharma.com/wp-content/uploads/2017/05/Platzbecker-U-MDS-Symposium-2017-Slides-Luspatercept-Response-in-New-Subpopulations-Website-Version.pdf>, (2017) (16 pages).

Platzbecker et al., "Luspatercept Significantly Reduces Red Blood Cell (RBC) Transfusion Burden, Regardless of Gene Mutation Frequency, Spectrum, and Prognostic Significance, Among Patients with Lower-Risk Myelodysplastic Syndromes Enrolled in the Medalist Trial," retrieved from < http://acceleronpharma.com/wp-content/uploads/2019/12/ASH-2019-Platzbecker-MEDALIST-Mutational-analysis.pdf>, (2019) (1 page).

Platzbecker et al., "Mutational and Subgroup Analyses of Lower-Risk Myelodysplastic Syndromes (MDS) Patients Treated With Luspatercept: Phase 2 PACE-MDS Study," 23rd European Hematology Association Congress, Jun. 14-17, Stockholm, Sweden, Abstract PF498, retrieved from <http://acceleronpharma.com/wp-content/uploads/2018/06/EHA-2018-MDS-Poster-06June2018.pdf>, (2018) (1 page).

Platzbecker et al., "Mutational Profile and Analysis of Lower-Risk Myelodysplastic Syndromes (MDS) Patients Treated with Luspatercept: Phase 2 PACE-MDS Study," American Society of Hematology (ASH) 59th Annual Meeting & Exposition, Dec. 9-12, Atlanta, GA, Abstract 2982, retrieved from <acceleronpharma.com/wp-content/uploads/2017/12/Platzbecker-U-ASH-2017-MDS-Luspatercept-Poster-Final.pdf> (2017) (1 page).

Platzebecker et al., "Erythropoietic cellular analyses in luspatercept-treated lower-risk myelodysplastic syndromes (MDS): Phase 2 PACE-MDS study," 2018 American Society of Clinical Oncology (ASCO) Annual Meeting, Jun. 1-5, Chicago, Illinois, Abstract 7018, retrieved from <http://acceleronpharma.com/wp-content/uploads/2018/06/Platzbecker-ASCO-2018-Poster-Erythropoietic-Cellular-Analyses-Ph-2-PACE-MDS-Study-1.pdf>, (2018) (1 page).

Porter et al., "Effects of Luspatercept on Iron Overload and Impact on Responders to Luspatercept: Results from the Believe Trial," 61st Annual Meeting of the American Society of Hematology (ASH), Abstract 2245, Blood. 134(Supplement 1):2245 (2019) (1 page).

Raftopoulos et al., "Sotatercept (ACE-011) for the treatment of chemotherapy-induced anemia in patients with metastatic breast cancer or advanced or metastatic solid tumors treated with platinum-based chemotherapeutic regimens: results from two phase 2 studies," Support Care Cancer. 24(4):1517-25 (2016).

Ruckle et al., "Single-Dose, Randomized, Double-Blind, Placebo-Controlled Study of ACE-011 (ActRIIA-IgG1) in Postmenopausal Women," J Bone Mineral Res. 24(4):744-752 (2009).

Sako et al., "Characterization of the ligand binding functionality of the extracellular domain of activin receptor Type IIB," J Biol Chem. 285(27):21037-48 (2010).

Sanchez et al., "Evaluation of Electrical Impedance as a Biomarker of Myostatin Inhibition in Wild Type and Muscular Dystrophy Mice," PLoS One. 10(10):e0140521 (2015) (14 pages).

Sherman et al., "Multiple-Dose, Safety, Pharmacokinetic, and Pharmacodynamic Study of Sotatercept (ActRIIA-IgGI), a Novel Erythropoietic Agent, in Healthy Postmenopausal Women," J Clin Pharmacol. 53(11):1121-1130 (2013).

Smith et al., "Long-term Effects of Sotatercept Compared With Placebo for Correction of Anemia in Hemodialysis Subjects: Interim Analysis of ACE-011-REN-001," 52nd ERA-EDTA Congress, May 28-31, London, UK, Poster FP661, retrieved from <http://acceleronpharma.com/wp-content/uploads/2017/03/20150529-ERA-2015_Sotatercept-Hb-Safety-Poster_05.22.15-Final-for-QR-Code-1.pdf>, (2015) (1 page).

Smith et al., "Quantitative Computed Tomography Results for Bone Mass and Abdominal Aortic Vascular Calcification in Hemodialysis Subjects Treated With Escalating Dose Levels of Sotatercept: Interim Analysis of ACE-011-REN-001," 52nd ERA-EDTA Congress, May 28-31, London, UK, Poster SP645, retrieved from <acceleronpharma.com/wp-content/uploads/2017/03/20150530-ERA-2015_Sotatercept-QCT-Poster_05.22.15-Final-for-QR-Code.pdf>, (2015) (1 page).

Sunada, "Anti-myostatin antibody therapy for myopathies," Clin Neurol. 51:1157-1159 (2011) (3 pages) (English abstract included).

Sunada, "Myostatin Blockade Therapy for Muscular Atrophy," Brain Nerve. 63(11):1271-7 (2011) (Abstract only) (2 pages).

Suragani et al., "Modified activin receptor IIB ligand trap mitigates ineffective erythropoiesis and disease complications in murine beta-thalassemia," Blood. 123(25):3864-3872 (2014).

Suragani et al., "Modified ActRIIB-Fc Fusion Protein (ACE-536) Decreases Irreversible Sickle Cells in a Murine Model of Sickle Cell Disease," EHA, Poster P535, retrieved from <acceleronpharma.com/wp-content/uploads/2017/03/20140614-ACE-536-20140613-Modified-ActRIIB-Fc-Fusion-Protein-Decreases-Irreversible-Sickle-Cells-in-a-Murine-Model-of-1.pdf>, (2014) (1 page).

Suragani et al., "Modified ActRIIB-mFc Fusion Protein (murine ortholog of Luspatercept) Mitigates Sickling and Red Cell Pathology in a Murine Model of Sickle Cell Disease," ASH 56th Annual Meeting, Dec. 6-9, San Francisco, California. Poster 4055 (2014).

Suragani et al., "Transforming growth factor-beta superfamily ligand trap ACE-536 corrects anemia by promoting late-stage erythropoiesis," Nat Med. 20(4):408-414 (2014) (10 pages).

Thevis et al., "Emerging drugs affecting skeletal muscle function and mitochondrial biogenesis—Potential implications for sports drug testing programs," Rapid Commun Mass Spectrom. 30(5):635-51 (2016).

(56) References Cited

OTHER PUBLICATIONS

Tomillero et al., “Gateways to Clinical Trials,” Methods Find Exp Clin Pharmacol. 32(1):47-86 (2010).
Townson et al., “Specificity and Structure of a High Affinity Activin Receptor-like Kinase 1 (ALK1) Signaling Complex,” J Biol Chem. 287(33):27313-27325 (2012).
Vallet et al., “Activin A promotes multiple myeloma-induced osteolysis and is a promising target for myeloma bone disease,” Proc Nat Acad Sci. 107(11):5124-9 (2010).
Viprakasit et al., “Evaluating Luspatercept Responders in the Phase 3, Randomized, Double-Blind, Placebo-Controlled Believe Trial of Luspatercept in Adult beta-Thalassemia Patients Who Require Regular Red Blood Cell Transfusions,” Blood. 134(Supplement 1):3545 (2019) (1 page).
Wagner et al., “Loss of myostatin attenuates severity of muscular dystrophy in mdx mice,” Ann Neurol. 52(6):832-6 (2002).
Wang et al., “A soluble activin receptor Type IIB does not improve blood glucose in streptozotocin-treated mice,” Int J Biol Sci. 11(2):199-208 (2015).
Wang et al., “Myostatin inhibition induces muscle fibre hypertrophy prior to satellite cell activation,” J Physiol. 590(9):2151-65 (2012).
Wells, “Additivity of mutational effects in proteins,” Biochemistry. 29(37):8509-17 (1990).
Wolfman et al., “Activation of latent myostatin by the BMP-1/tolloid family of metalloproteinases,” Proc Nat Acad Sci. 100(26):15842-6 (2003).
Yee et al., “Phase 1 Dose-Escalation Study of Sotatercept (ACE-011) in Combination with Lenalidomide and Dexamethasone in Patients with Relapsed and/or Refractory Multiple Myeloma,” Headache.1:0 (2015) (1 page).
Yu, “Sotatercept for rebalancing BMP/TGF-beta/activin signaling in PAH,” Scientific Sessions Presentation (2018) (12 pages).
Yung et al., “ACTRIIA-Fc rebalances BMP and activin/TGF-beta signaling to attenuate experimental pulmonary hypertension,” American Heart Association Scientific Session, Nov. 11-15, Anaheim, CA, retrieved from <acceleronpharma.com/wp-content/uploads/2017/11/Dr.-Yu-Presentation-AHA-17-1.pdf>, (2017) (15 pages).
Yung, “ACTRIIA-Fc Rebalances Activin/GDF and BMP9 Signaling to Attenuate Experimental Pulmonary Hypertension,” American Heart Association Scientific Session, Nov. 10-12, Chicago, Illinois, retrieved from <acceleronpharma.com/wp-content/uploads/2018/11/Lai-Ming-AHA-2018-ActRIIa-Fc-v2-final.pdf>, (2018) (14 pages).
Zimmers et al., “Induction of Cachexia in Mice by Systemically Administered Myostatin,” Science. 296(5572):1486-8 (2002) (4 pages).
International Search Report and Written Opinion for International Application No. PCT/US2021/023353, dated Jul. 20, 2021 (9 pages).
International Search Report and Written Opinion for International Application No. PCT/US2021/023335, dated Jul. 9, 2021 (41 pages).
International Search Report and Written Opinion for International Application No. PCT/US2021/023339, dated Jun. 21, 2021 (23 pages).
Kuo et al., “MB109 as bioactive human bone morphogenetic protein-9 refolded and purified from *E. coli* inclusion bodies,” Microb Cell Fact. 13(1):29 (2014) (13 pages).
Wu et al., “Identification and analysis of type II TGF-beta receptors in BMP-9-induced osteogenic differentiation of C3H10T1/2 mesenchymal stem cells,” Acta Biochim Biophys Sin (Shanghai). 42(10):699-708 (2010).

FIG. 1

| Construct | | |
| --- | --- | --- |
| ActRIIA | | C LFFNANWEKD RTNQTGVEPC YGDKDKRRHC FATWKNISGS IEIVKQGCWL DDINCYDRTD CVEKKDSPEV YFCCCEGNMC |
| ActRIIB | | C IYYNANWELE RTNQSGLERC EGEQDKRLHC YASWRNSSGT IELVKKGCWL DDFNCYDRQE CVATEENPQV YFCCCEGNFC |
| ActRIIA/B | GA | ILGRSETQEC LFYNANWELE RTNQTGVERC EGEKDKRLHC YATWRNISGS IEIVKKGCWL DDFNCYDRTD CVETEENPQV YFCCCEGNMC NEKFSYFPEM EVTQPTS |
| ActRIIB/A | | GRGEAETREC IYYNANWEKD RTNQSGLEPC YGDQDKRRHC FASWKNSSGT IELVKQGCWL DDINCYDRQE CVAKKDSPEV YFCCCEGNFC NERFTHLPEA GGPEVTYEPP PTAPT |
| ActRIIA/Bdelta9 | GA | ILGRSETQEC LFYNANWELD RTNQTGVERC EGEKDKRLHC YATWRNISGS IEIVKKGCWL DDFNCYDRTD CVETKENPQV YFCCCEGNMC NEKFSYFPEM EVTQPTS |
| ActRIIA/Bdelta9min | GA | ILGRSETQEC LFYNANWELD RTNQTGVEPC EGEKDKRLHC FATWKNISGS IEIVKKGCWL DDINCYDRTD CVETEENPQV YFCCCEGNMC NEKFSYFPEM EVTQPTS |
| ActRIIA/B+ | GA | ILGRSETQEC LFYNANWELE RTNQTGVERC EGEKDKRLHC YATWKNISGS IEIVAKGCWL DDFNCYDRTD CVETKENPQV YFCCCEGNMC NEKFSYFPEM EVTQPTS |
| ActRIIa/b-delta-9m2 | GA | ILGRSETQEC LFYNANWELD RTNQTGVERC EGEKDKRLHC YATWKNISGS IEIVKKGCWL DDINCYDRTD CVETKENPQV YFCCCEGNMC NEKFSYFPEM EVTQPTS |
| ActRIIa/b-delta-9m3 | GA | ILGRSETQEC LFYNANWELD RTNQTGVERC EGEKDKRLHC YATWKNISGS IEIVKKGCWL DDFNCYDRTD CVETEENPQV YFCCCEGNMC NEKFSYFPEM EVTQPTS |
| ActRIIa/b-delta-9m4 | GA | ILGRSETQEC LFYNANWELD RTNQTGVEPC YGEKDKRLHC YATWKNISGS IEIVKKGCWL DDFNCYDRTD CVETKENPQV YFCCCEGNMC NEKFSYFPEM EVTQPTS |
| ActRIIa/bmax1 | GA | ILGRSETQEC LYYNANWELE RTNQTGVERC EGEQDKRLHC YATWKNISGS IEIVKKGCWL DDFNCYDRTD CVETEENPQV YFCCCEGNMC NEKFSYFPEM EVTQPTS |
| ActRIIa/bmax2 | GA | ILGRSETQEC LFYNANWELE RTNQTGVERC EGEKDKRLHC YATWRNISGS IEIVKKGCWL DDFNCYDRTD CVETEENPQV YFCCCEGNMC NEKFSYFPEM EVTQPTSNP |
| ActRIIa/bmax3 | GA | ILGRSETQEC LFYNANWELE RTNQTGVERC EGEKDKRLHC YATWKNISGS IEIVKKGCWL DDFNCYDRTD CVETEENPQV YFCCCEGNMC NEKFSYFPEM EVTQPTSNPV TPK |
| | | |
| | | Blue = IIA residue into IIB |
| | | Red = IIB into IIA |
| | | Green = non IIa or IIb residue |

NUCLEIC ACID MOLECULES ENCODING ACTIVIN RECEPTOR TYPE IIA VARIANTS

SEQUENCE LISTING

The instant application contains a Sequence Listing which has been submitted electronically in ASCII format and is hereby incorporated by reference in its entirety. Said ASCII copy, created May 21, 2021, is named 51184-002005_Sequence_Listing_052121_ST25 and is 133,894 bytes in size.

BACKGROUND OF THE INVENTION

Duchenne muscular dystrophy (DMD), facioscapulohumeral muscular dystrophy (FSHD), inclusion body myositis (IBM), and amyotrophic lateral sclerosis (ALS) are examples of muscle diseases that involve weakness and atrophy of muscles and/or motor neurons that control voluntary muscle movements. DMD is caused by mutations in the X-linked dystrophin gene and characterized by progressive muscle degeneration and weakness in all skeletal muscles. FSHD particularly affects skeletal muscles of the face, shoulders, upper arms, and lower legs. IBM is an inflammatory muscle disease that mainly affects muscles of the thighs and muscles of the arms that control finger and wrist flexion. ALS is a motor neuron disease characterized by stiff muscles, muscle twitching, and muscle atrophy throughout the body due to the degeneration of the motor neurons. Efforts to improve treatment and survival of subjects having these devastating muscle diseases have not been successful.

Excess body weight is an increasing problem in the United States, with a prevalence of approximately 25% of the population. Increased visceral and subcutaneous fact causes dysfunction of various organs. Excessive body weight is a risk factor for an array of complications, including obesity, diabetes (e.g., Type-1 and Type-2 diabetes), cardiovascular disease, and several forms of cancer. Insulin resistance is also associated with obesity and occurs when pancreatic tissues require an elevated amount of insulin. Once pancreatic p cells can no longer produce sufficient insulin to meet the demand, hyperglycemia occurs and Type-2 diabetes develops. Adipocytes, which are increased in obesity, are believed to play a role in this process. Despite the prevalence of obesity and metabolic diseases such as diabetes (e.g., Type-1 and Type-2 diabetes) and insulin resistance, few therapeutic options are available.

There exists a need for novel treatments for these muscular and metabolic diseases.

SUMMARY OF THE INVENTION

The present invention features polypeptides that include an extracellular activin receptor type IIa (ActRIIa) variant. In some embodiments, a polypeptide of the invention includes an extracellular ActRIIa variant fused to the N- or C-terminus of an Fc domain monomer or moiety. Such moieties may be attached by amino acid or other covalent bonds and may increase stability of the polypeptide. A polypeptide including an extracellular ActRIIa variant fused to an Fc domain monomer may also form a dimer (e.g., a homodimer or heterodimer) through the interaction between two Fc domain monomers. The polypeptides of the invention may be used to increase muscle mass and strength in a subject having a disease or condition involving weakness and atrophy of muscles, e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia. The polypeptides of the invention may also be used to reduce body weight, reduce body fat, increase glucose clearance, increase insulin sensitivity, or reduce fasting insulin levels in a subject having or at risk of developing a metabolic disease, e.g., obesity, Type-1 diabetes, or Type-2 diabetes. Further, the polypeptides of the invention may also be used to affect myostatin, activin, and/or bone morphogenetic protein 9 (BMP9) signaling in a subject having a risk of developing or having a disease or condition involving weakness and atrophy of muscles or a metabolic disease.

In one aspect, the invention features a polypeptide including an extracellular activin receptor type IIa (ActRIIa) variant, the variant having a sequence of GAILGRSETQECL$X_1X_2$NANW$X_3X_4X_5X_6$TNQTGVE$X_7$C$X_8$GX$X_{10}X_{11}X_{12}X_{13}X_{14}$HC$X_{15}$ATW$X_{16}$NISGSIEIV$X_{17}X_{18}$GC$X_{19}X_{20}X_{21}$D$X_{22}$NCYDRTDCVE$X_{23}X_{24}X_{25}X_{26}$P$X_{27}$VYFCCCEGNMCNEKFSYFPEMEVTQPTS (SEQ ID NO: 1), wherein $X_1$ is F or Y; $X_2$ is F or Y; $X_3$ is E or A; $X_4$ is K or L; $X_5$ is D or E; $X_6$ is R or A; $X_7$ is P or R; $X_8$ is Y or E; $X_9$ is D or E; $X_{10}$ is K or Q; $X_1$ is D or A; $X_{12}$ is K or A; $X_{13}$ is R or A; $X_{14}$ is R or L; $X_{15}$ is F or Y; $X_{16}$ is K, R, or A; $X_{17}$ is K, A, Y, F, or I; $X_{18}$ is Q or K; $X_{19}$ is W or A; $X_{20}$ is L or A; $X_{21}$ is D, K, R, A, F, G, M, N, or I; $X_{22}$ is I, F, or A; $X_{23}$ is K or T; $X_{24}$ is K or E; $X_{25}$ is D or E; $X_{26}$ is S or N; and $X_{27}$ is E or Q, and wherein the variant has at least one amino acid substitution relative to a wild-type extracellular ActRIIa having the sequence of SEQ ID NO: 73 or an extracellular ActRIIa having any one of the sequences of SEQ ID NOs: 76-96.

In some embodiments, the variant has a sequence of GAILGRSETQECLF$X_2$NANW$X_3X_4X_5X_6$TNQTGVEXCXGXK$X_{11}X_{12}X_{13}X_{14}$HC$X_{15}$ATW$X_{16}$NISGSIEIV$X_{17}X_{18}$GC$X_{19}X_{20}X_{21}$D$X_{22}$NCYDRTDCVE$X_{23}X_{24}X_{25}X_2$P$X_{27}$VYFCCCEGNMCNEKFSYFPEMEVTQPTS (SEQ ID NO: 2), wherein $X_2$, $X_3$, $X_4$, $X_5$, $X_6$, $X_7$, $X_8$, $X_9$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, $X_{24}$, $X_{25}$, $X_{26}$, and $X_{27}$ are defined as above.

In some embodiments, the variant has a sequence of (SEQ ID NO: 3)

GAILGRSETQECLF$X_2$NANWE$X_4X_5$RTNQTGVE$X_7$C$X_8$G$X_9$KDKR$X_{14}$HC$X_{15}$ATW$X_{16}$NISGSIEIVK$X_{18}$GCWLDD$X_{22}$NCYDRTDCVE$X_{23}X_{24}X_{25}X_{26}$P$X_{27}$VYFCCCEGNMCNEKFSYFPEMEVTQPTS, wherein $X_2$, $X_4$, $X_7$, $X_8$, $X_9$, $X_{14}$, $X_{15}$, $X_{16}$, $X_{18}$, $X_{22}$, $X_{23}$, $X_{24}$, $X_{25}$, $X_{26}$, and $X_{27}$ are defined as above.

In some embodiments, the variant has a sequence of (SEQ ID NO: 4)

GAILGRSETQECLF$X_2$NANWE$X_4$DRTNQTGVE$X_7$C$X_8$G$X_9$KDKR$X_{14}$HC$X_{15}$ATW$X^{16}$NISGSIEIVK$X_{18}$GCWLDD$X_{22}$NCYDRTDCVE$X_{23}$K$X_{25}X_{26}$P$X_{27}$VYFCCCEGNMCNEKFSYFPEMEVTQPTS, wherein $X_2$, $X_4$, $X_7$, $X_8$, $X_9$, $X_{14}$, $X_{15}$, $X_{16}$, $X_{18}$, $X_{22}$, $X_{23}$, $X_{25}$, $X_{26}$, and $X_{27}$ are defined as above.

In some embodiments, the variant has a sequence of GAILGRSETQECLF$X_2$NANWE$X_4$DRTNQTGVEPC$X_8$G$X_9$KDKR$X_{14}$HCFATWKNISGSIEIVK$X_{18}$GCWLDDINCYDRTDCVE$X_{23}$K$X_{25}X_{26}$P$X_{27}$VYFCCCEGNMCNEKFSYFPEMEVTQPTS (SEQ ID NO: 5), wherein $X_2$, $X_4$, $X_8$, $X_9$, $X_{14}$, $X_{18}$, $X_{23}$, $X_{25}$, $X_{26}$, and $X_{27}$ are defined as above.

In any of the aforementioned embodiments, $X_1$ is F or Y. In any of the aforementioned embodiments, $X_2$ is F or Y. In any of the aforementioned embodiments, $X_3$ is E or A. In any of the aforementioned embodiments, $X_4$ is K or L. In any of the aforementioned embodiments, $X_s$ is D or E. In any of the aforementioned embodiments, $X_6$ is R or A. In any of the aforementioned embodiments, $X_7$ is P or R. In any of the aforementioned embodiments, $X_8$ is Y or E. In any of the aforementioned embodiments, $X_9$ is D or E. In any of the aforementioned embodiments, $X_{10}$ is K or Q. In any of the aforementioned embodiments, $X_{11}$ is D or A. In any of the aforementioned embodiments, $X_{12}$ is K or A. In any of the aforementioned embodiments, $X_{13}$ is R or A. In any of the aforementioned embodiments, $X_{14}$ is R or L. In any of the aforementioned embodiments, $X_{15}$ is F or Y. In any of the aforementioned embodiments, $X_{16}$ is K, R, or A. In any of the aforementioned embodiments, $X_{17}$ is K, A, Y, F, or I. In any of the aforementioned embodiments, $X_{18}$ is Q or K. In any of the aforementioned embodiments, $X_{1e}$ is W or A. In any of the aforementioned embodiments, $X_{20}$ is L or A. In any of the aforementioned embodiments, $X_{21}$ is D, K, R, A, F, G, M, N, or I. In any of the aforementioned embodiments, $X_{22}$ is I, F, or A. In any of the aforementioned embodiments, $X_{23}$ is K or T. In any of the aforementioned embodiments, $X_{24}$ is K or E. In any of the aforementioned embodiments, $X_{25}$ is D or E. In any of the aforementioned embodiments, $X_{26}$ is S or N. In any of the aforementioned embodiments, $X_{27}$ is E or Q. In any of the aforementioned embodiments, $X_{23}$ is T, $X_{24}$ is E, $X_{25}$ is E, and $X_{26}$ is N. In any of the aforementioned embodiments, $X_{23}$ is T, $X_{24}$ is K, $X_{25}$ is E, and $X_{26}$ is N. In any of the aforementioned embodiments, $X_{17}$ is K.

In any of the aforementioned embodiments, the variant has the sequence of any one of SEQ ID NOs: 6-72.

In any of the aforementioned embodiments, the amino acid at position $X_{24}$ may be replaced with the amino acid K.

In any of the aforementioned embodiments, the amino acid at position $X_{24}$ may be replaced with the amino acid E.

In any of the aforementioned embodiments, a polypeptide described herein may further include a C-terminal extension of one or more amino acids (e.g., 1, 2, 3, 4, 5, 6, or more amino acids). In some embodiments, the C-terminal extension is amino acid sequence NP. In some embodiments, the C-terminal extension is amino acid sequence NPVTPK (SEQ ID NO: 155).

In any of the aforementioned embodiments, a polypeptide described herein may further include a moiety fused or covalently linked to the C-terminus of the polypeptide. In some embodiments, the moiety increases stability or improves the pharmacokinetics of the polypeptide. In some embodiments, the moiety is an Fc domain, an albumin-binding peptide, a fibronectin domain, or human serum albumin.

In any of the aforementioned embodiments, a polypeptide described herein may further include an Fc domain monomer fused to the C-terminus of the polypeptide by way of a linker. In some embodiments, the polypeptide that includes an extracellular ActRIIa variant described herein fused to an Fc domain monomer may form a dimer (e.g., a homodimer or heterodimer) through the interaction between two Fc domain monomers. In some embodiments, the Fc domain monomer has the sequence of SEQ ID NO: 97 In any of the aforementioned embodiments, a polypeptide described herein may further include an Fc domain fused to the C-terminus of the polypeptide by way of a linker. In some embodiments, the Fc domain is a wild-type Fc domain. In some embodiments, the wild-type Fc domain has the sequence of SEQ ID NO: 151. In some embodiments, the Fc domain contains one or more amino acid substitutions.

In some embodiments, the Fc domain containing one or more amino acid substitutions does not form a dimer.

In any of the aforementioned embodiments, a polypeptide described herein may further include an albumin-binding peptide fused to the C-terminus of the polypeptide by way of a linker. In some embodiments, the albumin-binding peptide has the sequence of SEQ ID NO: 152.

In any of the aforementioned embodiments, a polypeptide described herein may further include a fibronectin domain fused to the C-terminus of the polypeptide by way of a linker. In some embodiments, the fibronectin domain peptide has the sequence of SEQ ID NO: 153.

In any of the aforementioned embodiments, a polypeptide described herein may further include a human serum albumin fused to the C-terminus of the polypeptide by way of a linker. In some embodiments, the human serum albumin has the sequence of SEQ ID NO: 154.

In some embodiments, the linker is an amino acid spacer. In some embodiments, the amino acid spacer is GGG, GGGA (SEQ ID NO: 98), GGGG (SEQ ID NO: 100), GGGAG (SEQ ID NO: 130), GGGAGG (SEQ ID NO: 131), or GGGAGGG (SEQ ID NO: 132).

In some embodiments, the amino acid spacer is GGGS (SEQ ID NO: 99), GGGGA (SEQ ID NO: 101), GGGGS (SEQ ID NO: 102), GGGGG (SEQ ID NO: 103), GGAG (SEQ ID NO: 104), GGSG (SEQ ID NO: 105), AGGG (SEQ ID NO: 106), SGGG (SEQ ID NO: 107), GAGA (SEQ ID NO: 108), GSGS (SEQ ID NO: 109), GAGAGA (SEQ ID NO: 110), GSGSGS (SEQ ID NO: 111), GAGAGAGA (SEQ ID NO: 112), GSGSGSGS (SEQ ID NO: 113), GAGAGAGAGA (SEQ ID NO: 114), GSGSGSGSGS (SEQ ID NO: 115), GAGAGAGAGAGA (SEQ ID NO: 116), and GSGSGSGSGSGS (SEQ ID NO: 117), GGAGGA (SEQ ID NO: 118), GGSGGS (SEQ ID NO: 119), GGAGGAGGA (SEQ ID NO: 120), GGSGGSGGS (SEQ ID NO: 121), GGAGGAGGAGGA (SEQ ID NO: 122), GGSGGSGGSGGS (SEQ ID NO: 123), GGAGGGAG (SEQ ID NO: 124), GGSGGGSG (SEQ ID NO: 125), GGAGGGAGGGAG (SEQ ID NO: 126), and GGSGGGSGGGSG (SEQ ID NO: 127), GGGGAGGGGAGGGGA (SEQ ID NO: 128), GGGGSGGGGSGGGGS (SEQ ID NO: 129), AAAL (SEQ ID NO: 133), AAAK (SEQ ID NO: 134), AAAR (SEQ ID NO: 135), EGKSSGSGSESKST (SEQ ID NO: 136), GSAGSAAGSGEF (SEQ ID NO: 137), AEAAAKEAAAKA (SEQ ID NO: 138), KESGSVSSEQLAQFRSLD (SEQ ID NO: 139), GENLYFQSGG (SEQ ID NO: 140), SACYCELS (SEQ ID NO: 141), RSIAT (SEQ ID NO: 142), RPACKIPNDLKQKVMNH (SEQ ID NO: 143), GGSAGGSGSGSSGGSSGASGTGTAGGTGSGSGTGSG (SEQ ID NO: 144), AAANSSIDLISVPVDSR (SEQ ID NO: 145), GGSGGGSEGGGSEGGGSEGGGSEGGGSEGGGSGGGS (SEQ ID NO: 146), EAAAK (SEQ ID NO: 147), or PAPAP (SEQ ID NO: 148).

In any of the aforementioned embodiments, the polypeptide described herein has a serum half-life of at least 7 days.

In any of the aforementioned embodiments, the polypeptide described herein binds to human bone morphogenetic protein 9 (BMP9) with a $K_D$ of 200 pM or higher. In some embodiments, the polypeptide binds to activin and/or myostatin and has reduced (e.g., weak) binding to human BMP9. In some embodiments, the polypeptide does not substantially bind to human BMP9.

In any of the aforementioned embodiments, the polypeptide described herein binds to human activin A with a $K_D$ of 800 pM or less.

In any of the aforementioned embodiments, the polypeptide described herein binds to human activin B with a $K_D$ of approximately 800 pM or less.

In any of the aforementioned embodiments, the polypeptide described herein binds to human GDF-11 with a $K_D$ of approximately 5 pM or higher.

In another aspect, the invention features a nucleic acid molecule encoding a polypeptide described herein (e.g., a polypeptide including an extracellular ActRIIa variant having a sequence of any one of SEQ ID NOs: 1-72 (e.g., SEQ ID NOs: 6-72)). In another aspect, the invention also features a vector including the nucleic acid molecule described herein.

In another aspect, the invention features a host cell that expresses a polypeptide described herein, wherein the host cell includes a nucleic acid molecule or a vector described in the previous two aspects, wherein the nucleic acid molecule or vector is expressed in the host cell.

In another aspect, the invention features a method of preparing a polypeptide described herein, wherein the method includes: a) providing a host cell including a nucleic acid molecule or a vector described herein, and b) expressing the nucleic acid molecule or vector in the host cell under conditions that allow for the formation of the polypeptide.

In another aspect, the invention features a pharmaceutical composition including a polypeptide, nucleic acid molecule, or vector described herein and one or more pharmaceutically acceptable carriers or excipients. In some embodiments of the pharmaceutical composition, the polypeptide, nucleic acid molecule, or vector is in a therapeutically effective amount.

In another aspect, the invention also features a construct including two identical polypeptides (e.g., a homodimer) each including an extracellular ActRIIa variant having a sequence of any one of SEQ ID NOs: 1-72 (e.g., SEQ ID NOs: 6-72)) fused to the N- or C-terminus of an Fc domain monomer (e.g., the sequence of SEQ ID NO: 97). The two Fc domain monomers in the two polypeptides interact to form an Fc domain in the construct.

In another aspect, the invention also features a construct including two different polypeptides (e.g., a heterodimer) each including an extracellular ActRIIa variant having a sequence of any one of SEQ ID NOs: 1-72 (e.g., SEQ ID NOs: 6-72)) fused to the N- or C-terminus of an Fc domain monomer (e.g., the sequence of SEQ ID NO: 97). The two Fc domain monomers in the two polypeptides interact to form an Fc domain in the construct.

In another aspect, the invention features a method of increasing muscle mass in a subject in need thereof. The method includes administering to the subject a therapeutically effective amount of a polypeptide, nucleic acid molecule, or vector described herein or a pharmaceutical composition described herein.

In some embodiments of the method of increasing muscle mass in a subject, the subject has Duchenne muscular dystrophy (DMD), facioscapulohumeral muscular dystrophy (FSHD), inclusion body myositis (IBM), amyotrophic lateral sclerosis (ALS), sarcopenia, or cancer cachexia.

In another aspect, the invention features a method of affecting myostatin, activin, and/or BMP9 signaling (e.g., reducing or inhibiting the binding of myostatin, activin, and/or BMP9 to their receptors) in a subject having a disease or condition involving weakness and atrophy of muscles, wherein method includes administering to the subject a therapeutically effective amount of a polypeptide, nucleic acid molecule, or vector described herein or a pharmaceutical composition described herein. In some embodiments of this aspect, the disease or condition is DMD, FSHD, IBM, ALS, sarcopenia, or cancer cachexia.

In another aspect, the invention features a method of treating a subject having DMD by administering to the subject a therapeutically effective amount of a polypeptide, nucleic acid molecule, or vector described herein or a pharmaceutical composition described herein.

In another aspect, the invention features a method of treating a subject having FSHD by administering to the subject a therapeutically effective amount of a polypeptide, nucleic acid molecule, or vector described herein or a pharmaceutical composition described herein.

In another aspect, the invention features a method of treating a subject having IBM by administering to the subject a therapeutically effective amount of a polypeptide, nucleic acid molecule, or vector described herein or a pharmaceutical composition described herein.

In another aspect, the invention features a method of treating a subject having ALS by administering to the subject a therapeutically effective amount of a polypeptide, nucleic acid molecule, or vector described herein or a pharmaceutical composition described herein.

In another aspect, the invention features a method of reducing body fat in a subject in need thereof by administering to the subject a therapeutically effective amount of a polypeptide, a nucleic acid molecule, or vector described herein or a pharmaceutical composition described herein.

In another aspect, the invention features a method of reducing body weight in a subject in need thereof by administering to the subject a therapeutically effective amount of a polypeptide, a nucleic acid molecule, or vector described herein or a pharmaceutical composition described herein.

In another aspect, the invention features a method of reducing blood glucose in a subject in need thereof by administering to the subject a therapeutically effective amount of a polypeptide, a nucleic acid molecule, or vector described herein or a pharmaceutical composition described herein.

In another aspect, the invention features a method of increasing insulin sensitivity in a subject in need thereof, by administering to the subject a therapeutically effective amount of a polypeptide, a nucleic acid molecule, or vector described herein or a pharmaceutical composition described herein.

In some embodiments of any of the above aspects, the subject has or is at risk of developing a metabolic disease. In some embodiments, the metabolic disease is selected from the group including obesity, Type-1 diabetes, and Type-2 diabetes.

In another aspect, the invention features a method of affecting myostatin, activin, and/or BMP9 signaling (e.g., reducing or inhibiting the binding of myostatin, activin, and/or BMP9 to their receptors) in a subject having or at risk of developing a metabolic disease by administering to the subject a therapeutically effective amount of a polypeptide, a nucleic acid molecule, or vector described herein or a pharmaceutical composition described herein.

In another aspect, the invention features a method of treating and/or preventing a metabolic disease in a subject by administering to the subject a therapeutically effective amount of a polypeptide, a nucleic acid molecule, or vector described herein or a pharmaceutical composition described herein.

In some embodiments of any of the above aspect, the metabolic disease is selected from the group including obesity, Type-1 diabetes, and Type-2 diabetes. In some embodiments of any of the above aspects, the metabolic disease is obesity. In some embodiments of any of the above aspects, the metabolic disease is Type-1 diabetes. In some embodiments of any of the above aspects, the metabolic disease is Type-2 diabetes.

In some embodiments of any of the above aspects, the method reduces body weight and/or percentage of body weight gain of said subject. In some embodiments of any of the above aspects, the method reduces amount of body fat and/or percentage of body fat of said subject. In some embodiments of any of the above aspects, the method does not affect the appetite for food intake of said subject. In some embodiments of any of the above aspects, the method reduces adiposity of said subject. In some embodiments of any of the above aspects, the method reduces the weights of epididymal and perirenal fat pads of said subject. In some embodiments of any of the above aspects, the method reduces the amount of subcutaneous and/or visceral fat of said subject. In some embodiments of any of the above aspects, the method lowers the level of fasting insulin of said subject. In some embodiments of any of the above aspects, the method lowers the level of blood glucose of said subject. In some embodiments of any of the above aspects, the method increases insulin sensitivity of said subject. In some embodiments of any of the above aspects, the method increases the rate of glucose clearance of said subject. In some embodiments of any of the above aspects, the method improves the serum lipid profile of said subject. In some embodiments of any of the above aspects, the method does not reduce lean mass.

In some embodiments of any of the above aspects, the method increases muscle mass.

In some embodiments of any of the above aspects, the method reduces or inhibits the binding of activin and/or myostatin to their receptors.

In some embodiments of any of the above aspects, the polypeptide, nucleic acid, vector, or pharmaceutical composition is administered in an amount sufficient to increase muscle mass and/or strength, affect myostatin, activin, and/or BMP9 signaling in the subject, or reduce or inhibit the binding of activin and/or myostatin to their receptors, In some embodiments of any of the above aspects, the polypeptide, nucleic acid, vector, or pharmaceutical composition is administered in an amount sufficient to reduce body fat, reduce the amount of subcutaneous fat, reduce the amount of visceral fat, reduce adiposity, reduce the weights of epididymal and perirenal fat pads, reduce body fat percentage, reduce body weight, reduce the percentage of body weight gain, reduce fasting insulin level, reduce blood glucose level, increase insulin sensitivity, affect myostatin, activin, and/or BMP9 signaling in the subject, reduce the proliferation of adipose cells, reduce or inhibit the binding of activin and/or myostatin to their receptors, reduce LDL, reduce triglycerides, improve the serum lipid profile, regulate insulin biosynthesis and/or secretion from p-cells, delay, postpone, or reduce the need for insulin, or increase glucose clearance.

In some embodiments of any of the methods described herein, the method does not cause a vascular complication (e.g., an increase vascular permeability or leakage) in the subject. In some embodiments of any of the methods described herein, the method increases bone mineral density in the subject.

In some embodiments of any of the above aspects, the variant has the sequence of SEQ ID NO: 69. In some embodiments, the variant having the sequence of SEQ ID NO: 69 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 69, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 58. In some embodiments, the variant having the sequence of SEQ ID NO: 58 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 58, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 6. In some embodiments, the variant having the sequence of SEQ ID NO: 6 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6, or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 6, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 38. In some embodiments, the variant having the sequence of SEQ ID NO: 38 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6, or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 38, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 41. In some embodiments, the variant having the sequence of SEQ ID NO: 41 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6, or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 41, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 44. In some embodiments, the variant having the sequence of SEQ ID NO: 44 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 44, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 70. In some embodiments, the variant having the sequence of SEQ ID NO: 70 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 70, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 71. In some embodiments, the variant having the sequence of SEQ ID NO: 71 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids VTPK). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 71, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 72. In some embodiments, the variant having the sequence of SEQ ID NO: 72 has the amino acid K at position $X_{17}$ and/or the amino acid sequence TEEN or TKEN at positions $X_{23}$, $X_{24}$, $X_{25}$, and $X_{26}$. In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 72, optionally having the amino acid K at position $X_{17}$ and/or the amino acid sequence TEEN or TKEN at positions $X_{23}$, $X_{24}$, $X_{25}$, and $X_{26}$.

Definitions

As used herein, the term "extracellular activin receptor type IIa (ActRIIa) variant" refers to a peptide including a soluble, extracellular portion of the single transmembrane receptor, ActRIIa, that has at least one amino acid substitution relative to a wild-type extracellular ActRIIa (e.g., bold portion of the sequence of SEQ ID NO: 75 shown below) or an extracellular ActRIIa having any one of the sequences of SEQ ID NOs: 76-96. The sequence of the wild-type, human ActRIIa precursor protein is shown below (SEQ ID NO: 75), in which the signal peptide is italicized and the extracellular portion is bold.

Wild-type, human ActRIIa precursor protein (SEQ ID NO: 75):

*MGAAAKLAFAVFLISCSS*GAILGRSETQECLFFNANWEKDRTNQTGVEP

CYGDKDKRRHCFATWKNISGSIEIVKQGCWLDDINCYDRTDCVEKKDSP

EVYFCCCEGNMCNEKFSYFPEMEVTQPTSNPVTPKPPYYNILLYSLVPL

MLIAGIVICAFWVYRHHKMAYPPVLVPTQDPGPPPPSPLLGLKPLQLLE

VKARGRFGCVWKAQLLNEYVAVKIFPIQDKQSWQNEYEVYSLPGMKHEN

ILQFIGAEKRGTSVDVDLWLITAFHEKGSLSDFLKANVVSWNELCHIAE

TMARGLAYLHEDIPGLKDGHKPAISHRDIKSKNVLLKNNLTACIADFGL

ALKFEAGKSAGDTHGQVGTRRYMAPEVLEGAINFQRDAFLRIDMYAMGL

VLWELASRCTAADGPVDEYMLPFEEEIGQHPSLEDMQEVVVHKKKRPVL

RDYWQKHAGMAMLCETIEECWDHDAEARLSAGCVGERITQMQRLTNIIT

TEDIVTVVTMVTNVDFPPKESSL

An extracellular ActRIIa variant may have a sequence of any one of SEQ ID NOs: 1-72. In particular embodiments, an extracellular ActRIIa variant has a sequence of any one of SEQ ID NOs: 6-72 (Table 2). In some embodiments, an extracellular ActRIIa variant may have at least 85% (e.g., at least 85%, 87%, 90%, 92%, 95%, 97%, or greater) amino acid sequence identity to the sequence of a wild-type extracellular ActRIIa (SEQ ID NO: 73).

As used herein, the term "extracellular ActRIIb variant" refers to a peptide including a soluble, extracellular portion of the single transmembrane receptor, ActRIIb, that has at least one amino acid substitution relative to a wild-type extracellular ActRIIb (e.g., the sequence of SEQ ID NO: 74). An extracellular ActRIIb variant may have the sequence of SEQ ID NO: 149 shown below:

extracellular ActRIIb variant (SEQ ID NO: 149):
GRGEAETRECIFYNANWEKDRTNQSGLEPCYGDQDKRRHCFASWKNSSG
TIELVKQGCWLDDINCYDRQECVAKKDSPEVYFCCCEGNFCNERFTHLP
EAGGPEVTYEPPPTAPT As used herein, the term "linker" refers to a linkage between two elements, e.g., peptides or protein domains. A polypeptide described herein may include an extracellular ActRIIa variant (e.g., an extracellular ActRIIa variant having a sequence of any one of SEQ ID NOs: 1-72 (e.g., SEQ ID NOs: 6-72)) fused to a moiety. The moiety may increase stability or improve pharmacokinetic properties of the polypeptide. The moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin) may be fused to the polypeptide by way of a linker. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 1-200 amino acid sequence) occurring between two elements, e.g., peptides or protein domains, to provide space and/or flexibility between the two elements. An amino acid spacer is part of the primary sequence of a polypeptide (e.g., fused to the spaced peptides via the polypeptide backbone). The formation of disulfide bonds, e.g., between two hinge regions that form an Fc domain, is not considered a linker.

As used herein, the term "Fc domain" refers to a dimer of two Fc domain monomers. An Fc domain has at least 80% sequence identity (e.g., at least 85%, 90%, 95%, 97%, or 100% sequence identity) to a human Fc domain that includes at least a $C_H2$ domain and a $C_H3$ domain. An Fc domain monomer includes second and third antibody constant domains ($C_H2$ and $C_H3$). In some embodiments, the Fc domain monomer also includes a hinge domain. An Fc domain does not include any portion of an immunoglobulin that is capable of acting as an antigen-recognition region, e.g., a variable domain or a complementarity determining region (CDR). In the wild-type Fc domain, the two Fc domain monomers dimerize by the interaction between the two $C_H3$ antibody constant domains, as well as one or more disulfide bonds that form between the hinge domains of the two dimerizing Fc domain monomers. In some embodiments, an Fc domain may be mutated to lack effector functions, typical of a "dead Fc domain." In certain embodiments, each of the Fc domain monomers in an Fc domain includes amino acid substitutions in the $C_H2$ antibody constant domain to reduce the interaction or binding between the Fc domain and an Fcγ receptor. In some embodiments, the Fc domain contains one or more amino acid substitutions that reduce or inhibit Fc domain dimerization. An Fc domain can be any immunoglobulin antibody isotype, including IgG, IgE, IgM, IgA, or IgD. Additionally, an Fc domain can be an IgG subtype (e.g., IgG1, IgG2a, IgG2b, IgG3, or IgG4). The Fc domain can also be a non-naturally occurring Fc domain, e.g., a recombinant Fc domain.

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments, an albumin-binding peptide has the sequence DICLPRWGCLW (SEQ ID NO: 152).

As used herein, the term "fibronectin domain" refers to a high molecular weight glycoprotein of the extracellular matrix, or a fragment thereof, that binds to, e.g., membrane-spanning receptor proteins such as integrins and extracellular matrix components such as collagens and fibrins. In some embodiments, a fibronectin domain is a fibronectin type III domain (SEQ ID NO: 153) having amino acids 610-702 of the sequence of UniProt ID NO: P02751. In other embodiments, a fibronectin domain is an adnectin protein.

As used herein, the term "human serum albumin" refers to the albumin protein present in human blood plasma. Human serum albumin is the most abundant protein in the blood. It constitutes about half of the blood serum protein. In some embodiments, a human serum albumin has the sequence of UniProt ID NO: P02768 (SEQ ID NO: 154).

As used herein, the term "fused" is used to describe the combination or attachment of two or more elements, components, or protein domains, e.g., peptides or polypeptides, by means including chemical conjugation, recombinant means, and chemical bonds, e.g., amide bonds. For example, two single peptides in tandem series can be fused to form one contiguous protein structure, e.g., a polypeptide, through chemical conjugation, a chemical bond, a peptide linker, or any other means of covalent linkage. In some embodiments of a polypeptide described herein, an extracellular ActRIIa variant (e.g., an extracellular ActRIIa variant having the sequence of any one of SEQ ID NOs: 1-72 (e.g., SEQ ID NOs: 6-72)) may be fused in tandem series to the N- or C-terminus of a moiety (e.g., Fc domain monomer (e.g., the sequence of SEQ ID NO: 97) a wild-type Fc domain (e.g., the sequence of SEQ ID NO: 151), an Fc domain with amino acid substitutions (e.g., one or more substitutions that reduce dimerization), an albumin-binding peptide (e.g., the sequence of SEQ ID NO: 152), a fibronectin domain (e.g., the sequence of SEQ ID NO: 153), or a human serum albumin (e.g., the sequence of SEQ ID NO: 154)) by way of a linker. For example, an extracellular ActRIIa variant is fused to a moiety (e.g., an Fc domain monomer, a wild-type Fc domain, an Fc domain with amino acid substitutions (e.g., one or more substitutions that reduce dimerization), an albumin-binding peptide, a fibronectin domain, or a human serum albumin) by way of a peptide linker, in which the N-terminus of the peptide linker is fused to the C-terminus of the extracellular ActRIIa variant through a chemical bond, e.g., a peptide bond, and the C-terminus of the peptide linker is fused to the N-terminus of the moiety (e.g., Fc domain monomer, wild-type Fc domain, Fc domain with amino acid substitutions (e.g., one or more substitutions that reduce dimerization), albumin-binding peptide, fibronectin domain, or human serum albumin) through a chemical bond, e.g., a peptide bond.

As used herein, the term "C-terminal extension" refers to the addition of one or more amino acids to the C-terminus of a polypeptide including an extracellular ActRIIa variant (e.g., an extracellular ActRIIa variant having the sequence of any one of SEQ ID NOs: 1-70 (e.g., SEQ ID NOs: 6-70)). The C-terminal extension can be 1-6 amino acids (e.g., 1, 2, 3, 4, 5, 6 or more amino acids). Exemplary C-terminal extensions are the amino acid sequence NP (a two amino acid C-terminal extension) and the amino acid sequence NPVTPK (SEQ ID NO: 155) (a six amino acid C-terminal extension). Any amino acid sequence that does not disrupt the activity of the polypeptide can be used. SEQ ID NO: 71, which is the sequence of SEQ ID NO: 69 with a C-terminal extension of NP, and SEQ ID NO: 72, which is the sequence of SEQ ID NO: 69 with a C-terminal extension of NPVTPK (SEQ ID NO: 155), represent two of the possible ways that a polypeptide of the invention can be modified to include a C-terminal extension.

As used herein, the term "percent (%) identity" refers to the percentage of amino acid (or nucleic acid) residues of a candidate sequence, e.g., an extracellular ActRIIa variant, that are identical to the amino acid (or nucleic acid) residues of a reference sequence, e.g., a wild-type extracellular ActRIIa (e.g., SEQ ID NO: 73), after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100\times(\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

As used herein, the term "serum half-life" refers to, in the context of administering a therapeutic protein to a subject, the time required for plasma concentration of the protein in the subject to be reduced by half. The protein can be redistributed or cleared from the bloodstream, or degraded, e.g., by proteolysis. As described herein, a polypeptide including an extracellular ActRIIa variant (e.g., an extracellular ActRIIa variant having a sequence of any one of SEQ ID NOs: 1-72 (e.g., SEQ ID NOs: 6-72)) displays a serum half-life of 7 days in humans.

As used herein, the term "metabolic disease" refers to a disease, disorder, or syndrome that is related to a subject's metabolism, such as breaking down carbohydrates, proteins, and fats in food to release energy, and converting chemicals into other substances and transporting them inside cells for energy utilization and/or storage. Some symptoms of a metabolic disease include high serum triglycerides, high low-density cholesterol (LDL), low high-density cholesterol (HDL), and/or high fasting insulin levels, elevated fasting plasma glucose, abdominal (central) obesity, and elevated blood pressure. Metabolic diseases increase the risk of developing other diseases, such as cardiovascular disease. In the present invention, metabolic diseases include, but are not limited to, obesity, Type-1 diabetes, and Type-2 diabetes.

As used herein, the term "percentage of body weight gain" refers to the percentage of gained body weight compared to a prior body weight of a subject at a prior time. The percentage of body weight gain can be calculated as follows:

$$100\times[(\text{body weight at a later time}-\text{body weight at a prior time})/(\text{body weight at a prior time})]$$

In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72)), or vector containing such a nucleic acid molecule to a subject reduces the percentage of body weight gain of the subject.

As used herein, the term "appetite for food intake" refers to a subject's natural desire or need for food. The appetite for food intake of a subject can be monitored by measuring the amount of food consumed after the polypeptide including an extracellular ActRIIa variant (e.g., an extracellular ActRIIa variant having the sequence of any one of SEQ ID NOs: 1-72 (e.g., SEQ ID NOs: 6-72)) is administered. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72)), or vector containing such a nucleic acid molecule to a subject does not affect the subject's appetite for food intake.

As used herein, the term "adiposity" refers to the fat stored in the adipose tissue of a subject. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72)), or vector containing such a nucleic acid molecule to a subject reduces the subject's adiposity without affecting lean mass.

As used herein, the term "lean mass" refers to a component of body composition which includes, e.g., lean mass, body fat, and body fluid. Normally lean mass is calculated by subtracting the weights of body fat and body fluid from total body weight. Typically, a subject's lean mass is between 60% and 90% of totally body weight. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72)), or vector containing such a nucleic acid molecule to a subject reduces the subject's adiposity (i.e., fat) without affecting lean mass.

As used herein, the term "epididymal and perirenal fat pads" refers to the tightly packed fat cells in the epididymis and around the kidney. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72)), or vector containing such a nucleic acid molecule to a subject reduces the weights of epididymal and perirenal fat pads of the subject.

As used herein, the term "fasting insulin" refers to a subject's level of insulin while the subject has not had any food intake for a length of time (i.e., 12-24 hours). Fasting insulin level is used in diagnosing metabolic diseases. Fasting insulin level is also used as an indication of whether a subject is at the risk of developing a metabolic disease. Normally, in a subject suffering from Type-1 diabetes, the subject's fasting insulin level is low compared to that of a healthy subject. In a subject suffering from insulin resistance (i.e., Type-2 diabetes), the subject's fasting insulin level is high compared to that of a healthy subject. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72)), or vector containing such a nucleic acid molecule to a subject lowers the subject's fasting insulin level.

As used herein, the term "rate of glucose clearance" refers to the rate at which glucose is being cleared from the blood. The rate of glucose clearance can be measured in a glucose tolerance test (GTT). In a GTT, a subject is given a certain amount of glucose and blood samples are taken afterward to determine how quickly it is cleared from the blood. The rate of glucose clearance can be used as a parameter in diagnosing and/or determining the risk of developing metabolic diseases such as obesity, diabetes, and insulin resistance.

As used herein, the term "serum lipid profile" refers to the measurement of the distribution of different types of lipids and lipoproteins in a subject's serum. Such measurement can be accomplished by a panel of blood tests. The types of lipids and lipoproteins in a subject's serum include, but are not limited to, cholesterol (e.g., high-density lipoprotein (HDL) and low-density lipoprotein (LDL)), triglyceride, and free fatty acid (FFA). The distribution of the different types of lipids and lipoproteins can be used as a parameter in diagnosing and/or determining the risk of developing metabolic diseases such as obesity, diabetes, and insulin resistance. High levels of cholesterol, especially low-density lipoprotein, is generally regarded as an indication or risk factor for developing certain metabolic diseases, or in some severe medical cases, cardiovascular diseases. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72)), or vector containing such a nucleic acid molecule to a subject improves the subject's serum lipid profile such that the levels of cholesterol (especially low-density lipoprotein) and triglyceride are lowered.

As used herein, the term "affinity" or "binding affinity" refers to the strength of the binding interaction between two molecules. Generally, binding affinity refers to the strength of the sum total of non-covalent interactions between a molecule and its binding partner, such as an extracellular ActRIIa variant and BMP9 or activin A. Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. The $K_D$ of two interacting molecules may be determined using methods and techniques well known in the art, e.g., surface plasmon resonance. $K_D$ is calculated as the ratio of $k_{on}/k_{on}$.

As used herein, the term "muscle mass" refers to a component of body composition. Normally muscle mass is calculated by subtracting the weights of body fat and body fluid from total body weight.

The percentage of muscle mass may vary greatly among individuals depending on a subject's genetic makeup, age, race, and health status, etc. Typically, a subject's muscle mass may be between 20% and 50% of totally body weight.

As used herein, the phrase "affecting myostatin, activin, and/or BMP9 signaling" means changing the binding of myostatin, activin, and/or BMP9 to their receptors, e.g., ActRIIa, ActRIIb, and BMPRII (e.g., ActRIIa). In some embodiments, a polypeptide including an extracellular ActRIIa variant described herein reduces or inhibits the binding of myostatin, activin, and/or BMP9 to their receptors, e.g., ActRIIa, ActRIIb, and BMPRII (e.g., ActRIIa). As described herein, a polypeptide of the invention including an extracellular ActRIIa variant (e.g., an extracellular ActRIIa variant having the sequence of any one of SEQ ID NOs: 1-72 (e.g., SEQ ID NOs: 6-72)) may have weak binding affinity to BMP9 (e.g., $K_D$ of 200 pM or higher).

As used herein, the term "vascular complication" refers to a vascular disorder or any damage to the blood vessels, such as damage to the blood vessel walls. Damage to the blood vessel walls may cause an increase in vascular permeability or leakage. The term "vascular permeability or leakage" refers to the capacity of the blood vessel walls to allow the flow of small molecules, proteins, and cells in and out of blood vessels. An increase in vascular permeability or leakage may be caused by an increase in the gaps (e.g., an increase in the size and/or number of the gaps) between endothelial cells that line the blood vessel walls and/or thinning of the blood vessel walls.

As used herein, the term "polypeptide" describes a single polymer in which the monomers are amino acid residues which are covalently conjugated together through amide bonds. A polypeptide is intended to encompass any amino acid sequence, either naturally occurring, recombinant, or synthetically produced.

As used herein, the term "homodimer" refers to a molecular construct formed by two identical macromolecules, such as proteins or nucleic acids. The two identical monomers may form a homodimer by covalent bonds or non-covalent bonds. For example, an Fc domain may be a homodimer of two Fc domain monomers if the two Fc domain monomers contain the same sequence. In another example, a polypeptide described herein including an extracellular ActRIIa variant fused to an Fc domain monomer may form a homodimer through the interaction of two Fc domain monomers, which form an Fc domain in the homodimer.

As used herein, the term "heterodimer" refers to a molecular construct formed by two different macromolecules, such as proteins or nucleic acids. The two monomers may form a heterodimer by covalent bonds or non-covalent bonds. For example, a polypeptide described herein including an extracellular ActRIIa variant fused to an Fc domain monomer may form a heterodimer through the interaction of two Fc domain monomers, each fused to a different ActRIIa variant, which form an Fc domain in the heterodimer.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell or a HEK293 cell).

As used herein, the term "therapeutically effective amount" refers an amount of a polypeptide, nucleic acid, or vector of the invention or a pharmaceutical composition containing a polypeptide, nucleic acid, or vector of the invention effective in achieving the desired therapeutic effect in treating a patient having a disease, such as a muscle disease, or a condition involving weakness and atrophy of muscles, e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia. The term "therapeutically effective amount" also refers an amount of a polypeptide, nucleic acid, or vector of the invention or a pharmaceutical composition containing a polypeptide, nucleic acid, or vector of the invention effective in achieving the desired therapeutic effect in treating a patient having a disease, such as a metabolic disease, or a condition involving excess body weight, excess body fat, high blood glucose, high fasting insulin levels, or insulin resistance, e.g., obesity, Type-1 diabetes, or Type-2 diabetes. In particular, the therapeutically effective amount of the polypeptide, nucleic acid, or vector avoids adverse side effects.

As used herein, the term "pharmaceutical composition" refers to a medicinal or pharmaceutical formulation that includes an active ingredient as well as excipients and diluents to enable the active ingredient suitable for the method of administration. The pharmaceutical composition of the present invention includes pharmaceutically acceptable components that are compatible with the polypeptide, nucleic acid, or vector. The pharmaceutical composition may be in tablet or capsule form for oral administration or in aqueous form for intravenous or subcutaneous administration.

As used herein, the term "pharmaceutically acceptable carrier or excipient" refers to an excipient or diluent in a pharmaceutical composition. The pharmaceutically acceptable carrier must be compatible with the other ingredients of the formulation and not deleterious to the recipient. In the present invention, the pharmaceutically acceptable carrier or excipient must provide adequate pharmaceutical stability to the polypeptide including an extracellular ActRIIa variant, the nucleic acid molecule(s) encoding the polypeptide, or a vector containing such nucleic acid molecule(s). The nature of the carrier or excipient differs with the mode of administration. For example, for intravenous administration, an aqueous solution carrier is generally used; for oral administration, a solid carrier is preferred.

As used herein, the term "treating and/or preventing" refers to the treatment and/or prevention of a disease, e.g., a metabolic disease (e.g., obesity, Type1 and Type-2 diabetes) or a muscle disease (e.g., DMD, FSHD, IBM, and ALS), using methods and compositions of the invention. Generally, treating a metabolic or muscle disease occurs after a subject has developed the metabolic or muscle disease and/or is already diagnosed with the metabolic or muscle disease. Preventing a metabolic or muscle disease refers to steps or procedures taken when a subject is at risk of developing the metabolic or muscle disease. The subject may show signs or mild symptoms that are judged by a physician to be indications or risk factors for developing the metabolic or muscle disease or have a family history or genetic predisposition of developing the metabolic or muscle disease, but has not yet developed the disease.

As used herein, the term "subject" refers to a mammal, e.g., preferably a human. Mammals include, but are not limited to, humans and domestic and farm animals, such as monkeys (e.g., a cynomolgus monkey), mice, dogs, cats, horses, and cows, etc.

DESCRIPTION OF THE DRAWINGS

FIG. 1 is a sequence alignment showing the wild-type sequences of extracellular ActRIIa and ActRIIb and the amino acid substitutions in ActRIIa variants.

DETAILED DESCRIPTION OF THE INVENTION

Figure 2B:
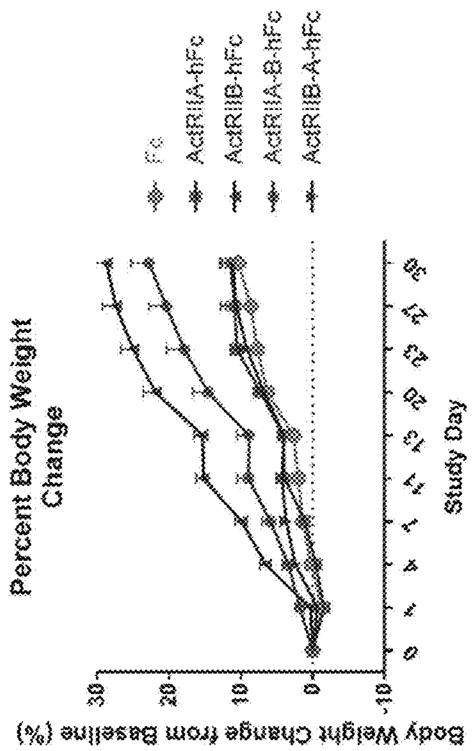
FIGS. 2A and 2B are scatter plots showing the effects of extracellular ActRIIa variants on body weight. Mice received a single hydrodynamic injection of a plasmid construct encoding the indicated ActRIIa variant or a control plasmid.

The invention features polypeptides that include an extracellular activin receptor type IIa (ActRIIa) variant. In some embodiments, a polypeptide of the invention includes an extracellular ActRIIa variant fused to a moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin). A polypeptide including an extracellular ActRIIa variant fused to an Fc domain monomer may also form a dimer (e.g., homodimer or heterodimer) through the interaction between two Fc domain monomers. The ActRIIa variants described herein have weak binding affinity or no binding affinity to bone morphogenetic protein 9 (BMP9) compared to activins and myostatin. The invention also includes methods of treating diseases and conditions involving weakness and atrophy of muscles by increasing muscle mass and strength, methods of treating or preventing metabolic diseases, or methods of affecting myostatin, activin, and/or BMP9 signaling in a subject by administering to the subject a polypeptide including an extracellular ActRIIa variant described herein. 1. Extracellular activin receptor type IIa (ActRIIa) variants Activin type II receptors are single transmembrane domain receptors that modulate signals for ligands in the transforming growth factor β (TGF-β) superfamily. Ligands in the TGF-β superfamily are involved in a host of physiological processes, such as muscle growth, vascular growth, cell differentiation, homeostasis, and osteogenesis. Examples of ligands in the TGF-β superfamily include, e.g., activin, inhibin, growth differentiation factors (GDFs) (e.g., GDF8, also known as myostatin), and bone morphogenetic proteins (BMPs) (e.g., BMP9). Myostatin and activins are known to play a role in the regulation of skeletal muscle growth. For example, mice without myostatin show a large increase in skeletal muscle mass.

Activins are also highly expressed in adipose tissue, and increased myostatin levels and activin receptor levels have been observed in subcutaneous and visceral fat of obese mice. Additionally, myostatin has been shown to be elevated in skeletal muscle and plasma of obese and insulin resistant women, and both type I and type II activin receptors have been linked to pancreatic function and diabetes. These data suggest that increased signaling through activin receptors, either due to increased expression of activin ligands (e.g., activin, myostatin) or increased expression of activin receptors themselves, could lead to obesity and metabolic disorders, such as Type-1 and Type-2 diabetes. Methods that reduce or inhibit this signaling could, therefore, be used in the treatment of obesity and metabolic disorders.

There exist two types of activin type II receptors: ActRIIa and ActRIIb. Studies have shown that BMP9 binds ActRIIb with about 300-fold higher binding affinity than ActRIIa (see, e.g., Townson et al., J. Biol. Chem. 287:27313, 2012). ActRIIa is known to have a longer half-life compared to ActRIIb. The present invention describes extracellular ActRIIa variants that are constructed by introducing amino acid residues of ActRIIb to ActRIIa, with the goal of imparting physiological properties conferred by ActRIIb, while also maintaining beneficial physiological and pharmacokinetic properties of ActRIIa. The optimum peptides confer significant increases in muscle mass, while retaining longer serum half-life and low binding-affinity to BMP9, for example. The preferred ActRIIa variants also exhibit improved binding to activins and/or myostatin compared to wild-type ActRIIa, which allows them to compete with endogenous activin receptors for ligand binding and reduce or inhibit endogenous activin receptor signaling. These variants can be used to treat disorders in which activin receptor signaling is elevated, such as metabolic disorders, leading to a reduction in body fat, body weight, or insulin resistance (e.g., an increase in insulin sensitivity). In some embodiments, amino acid substitutions may be introduced to an extracellular ActRIIa variant to reduce or remove the binding affinity of the variant to BMP9. The wild-type amino acid sequences of the extracellular portions of human ActRIIa and ActRIIb are shown below.

```
Human ActRIIa, extracellular portion (SEQ ID
NO: 73):
GAILGRSETQECLFFNANWEKDRTNQTGVEPCYGDKDKRRHCFATWKNI
SGSIEIVKQGCWLDDINCYDRTDCVEKKDSPEVYFCCCEGNMCNEKFSY
FPEMEVTQPTS

Human ActRIIb, extracellular portion (SEQ ID
NO: 74):
GRGEAETRECIYYNANWELERTNQSGLERCEGEQDKRLHCYASWRNSSG
TIELVKKGCWLDDFNCYDRQECVATEENPQVYFCCCEGNFCNERFTHLP
EAGGPEVTYEPPPTAPT
```

Polypeptides described herein include an extracellular ActRIIa variant having at least one amino acid substitution relative to the wild-type extracellular ActRIIa having the sequence of SEQ ID NO: 73 or the extracellular ActRIIa having any one of the sequences of SEQ ID NOs: 76-96. Possible amino acid substitutions at 27 different positions may be introduced to an extracellular ActRIIa variant (Table 1). In some embodiments, an extracellular ActRIIa variant may have at least 85% (e.g., at least 85%, 87%, 90%, 92%, 95%, 97%, or greater) amino acid sequence identity to the sequence of a wild-type extracellular ActRIIa (SEQ ID NO: 73). An extracellular ActRIIa variant may have one or more (e.g., 1-27, 1-25, 1-23, 1-21, 1-19, 1-17, 1-15, 1-13, 1-11, 1-9, 1-7, 1-5, 1-3, or 1-2; e.g., 1, 2, 3, 4, 5, 6, 7, 8, 9, 10, 11, 12, 13, 14, 15, 16, 17, 18, 19, 20, 21, 22, 23, 24, 25, 26, or 27) amino acid substitutions relative the sequence of a wild-type extracellular ActRIIa (SEQ ID NO: 73). In some embodiments, an extracellular ActRIIa variant (e.g., an extracellular ActRIIa variant having a sequence of SEQ ID NO: 1) may include amino acid substitutions at all of the 27 positions as listed in Table 1. In some embodiments, an extracellular ActRIIa variant may include amino acid substitutions at a number of positions, e.g., at 2, 4, 6, 8, 10, 12, 14, 16, 18, 20, 22, 24, or 26 out of the 27 positions, as listed in Table 1.

Amino acid substitutions can worsen or improve the activity and/or binding affinity of the ActRIIa variants of the invention. To maintain polypeptide function, it is important that the lysine (K) at position $X_{17}$ in the sequences shown in Tables 1 and 2 (SEQ ID NOs: 1-72 (e.g., SEQ ID NOs: 6-72)) be retained. Substitutions at that position can lead to a loss of activity. For example, an ActRIIa variant having the sequence GAILGRSETQECLFYNANWEL-ERTNQTGVERCEGEKDKRLHCYATWRNISGSIEI-VAKGCWLDDFNCYD RTDCVETEENPQVYFCC-CEGNMCNEKFSYFPEMEVTQPTS (SEQ ID NO: 150) has reduced activity in vivo, indicating that the substitution of alanine (A) for lysine (K) at $X_{17}$ is not tolerated. ActRIIa variants of the invention, including variants in Tables 1 and 2 (e.g., SEQ ID NOs: 1-72 (e.g., SEQ ID NOs: 6-72), therefore, retain amino acid K at position $X_{17}$.

The ActRIIa variants of the invention preferably have reduced, weak, or no substantial binding to BMP9. BMP9 binding is reduced in ActRIIa variants containing the amino acid sequence TEEN at positions $X_{23}$, $X_{24}$, $X_{25}$, and $X_{26}$, as well as in variants that maintain the amino acid K at position $X_{24}$ and have the amino acid sequence TKEN at positions $X_{23}$, $X_{24}$, $X_{25}$, and $X_{26}$. The sequences TEEN and TKEN can be employed interchangeably in the ActRIIa variants (e.g., the variants in Tables 1 and 2, e.g., SEQ ID NOs: 1-72 (e.g., SEQ ID NOs: 6-72)) of the invention to provide reduced BMP9 binding.

The ActRIIa variants of the invention may further include a C-terminal extension (e.g., additional amino acids at the C-terminus). The C-terminal extension can add one to six additional amino acids at the C-terminus (e.g., 1, 2, 3, 4, 5, 6 or more additional amino acids) to any of the variants shown in Tables 1 and 2 (e.g., SEQ ID NOs: 1-70 (e.g., SEQ ID NOs: 6-70)). One potential C-terminal extension that can be included in the ActRIIa variants of the invention is amino acid sequence NP. For example, the sequence including the C-terminal extension is SEQ ID NO: 71 (e.g., SEQ ID NO: 69 with a C-terminal extension of NP). Another exemplary C-terminal extension that can be included in the ActRIIa variants of the invention is amino acid sequence NPVTPK (SEQ ID NO: 155). For example, the sequence including the C-terminal extension is SEQ ID NO: 72 (e.g., SEQ ID NO: 69 with a C-terminal extension of NPVTPK (SEQ ID NO: 155)).

TABLE 1

| Amino acid substitutions in an extracellular ActRIIa variant having a sequence of any one of SEQ ID NOs: 1-5 |
| --- |
| GAILGRSETQECL$X_{1}X_{2}$NANW$X_{3}X_{4}X_{5}X_{6}$TNQTGVE$X_{7}$C$X_{8}$G$X_{9}X_{10}X_{11}X_{12}X_{13}X_{14}$HC$X_{15}$ATW$X_{16}$NISGSIEIV $X_{17}X_{18}$GC$X_{19}X_{20}X_{21}$D$X_{22}$NCYDRTDCVE$X_{23}X_{24}X_{25}X_{26}$P$X_{27}$VYFCCCEGNMCNEKFSYFPEMEVTQPTS (SEQ ID NO: 1) |
| GAILGRSETQECLF$X_{2}$NANW$X_{3}X_{4}X_{5}X_{6}$TNQTGVE$X_{7}$C$X_{8}$G$X_{9}$K$X_{11}X_{12}X_{13}X_{14}$HC$X_{15}$ATW$X_{16}$NISGSIEIV $X_{17}X_{18}$GC$X_{19}X_{20}X_{21}$D$X_{22}$NCYDRTDCVE$X_{23}X_{24}X_{25}X_{26}$P$X_{27}$VYFCCCEGNMCNEKFSYFPEMEVTQPTS (SEQ ID NO: 2) |

TABLE 1-continued

| Amino acid substitutions in an extracellular ActRIIa variant having a sequence of any one of SEQ ID NOs: 1-5 | | | |
|---|---|---|---|
| GAILGRSETQECLFX$_2$NANWEX$_4$X$_5$RTNQTGVEX$_7$CX$_8$GX$_9$KDKRX$_{14}$HCX$_{15}$ATWX$_{16}$NISGSIEIVKX$_{18}$GC WLDDX$_{22}$NCYDRTDCVEX$_{23}$X$_{24}$X$_{25}$X$_{26}$PX$_{27}$VYFCCCEGNMCNEKFSYFPEMEVTQPTS (SEQ ID NO: 3) | | | |
| GAILGRSETQECLFX$_2$NANWEX$_4$DRTNQTGVEX$_7$CX$_8$GX$_9$KDKRX$_{14}$HCX$_{15}$ATWX$_{16}$NISGSIEIVKX$_{18}$GC WLDDX$_{22}$NCYDRTDCVEX$_{23}$KX$_{25}$X$_{26}$PX$_{27}$VYFCCCEGNMCNEKFSYFPEMEVTQPTS (SEQ ID NO: 4) | | | |
| GAILGRSETQECLFX$_2$NANWEX$_4$DRTNQTGVEPCX$_8$GX$_9$KDKRX$_{14}$HCFATWKNISGSIEIVKX$_{18}$GCWLD DINCYDRTDCVEX$_{23}$KX$_{25}$X$_{26}$PX$_{27}$VYFCCCEGNMCNEKFSYFPEMEVTQPTS (SEQ ID NO: 5) | | | |
| $X_1$ | F or Y | $X_{15}$ | F or Y |
| $x_2$ | F or Y | $X_{16}$ | K, R, or A |
| $x_3$ | E or A | $X_{17}$ | K, A, Y, F, or I |
| $x_4$ | K or L | $X_{18}$ | Q or K |
| $X_5$ | D or E | $X_{19}$ | W or A |
| $X_6$ | R or A | $X_{20}$ | L or A |
| $x_7$ | P or R | $X_{21}$ | D, K, R, A, F, G, M, N, or I |
| GAILGRSETQECLX$_1$X$_2$NANWX$_3$X$_4$X$_5$X$_6$TNQTGVEX$_7$CX$_8$GX$_9$X$_{10}$X$_{11}$X$_{12}$X$_{13}$X$_{14}$HCX$_{15}$ATWX$_{16}$NISGSIEIV X$_{17}$X$_{18}$GCX$_{19}$X$_{20}$X$_{21}$DX$_{22}$NCYDRTDCVEX$_{23}$X$_{24}$X$_{25}$X$_{26}$PX$_{27}$VYFCCCEGNMCNEKFSYFPEMEVTQPTS (SEQ ID NO: 1) | | | |
| GAILGRSETQECLFX$_2$NANWX$_3$X$_4$X$_5$X$_6$TNQTGVEX$_7$CX$_8$GX$_9$KX$_{11}$X$_{12}$X$_{13}$X$_{14}$HCX$_{15}$ATWXINISGSIEIVX$_{17}$ X$_{18}$GCX$_{19}$X$_{20}$X$_{21}$DX$_{22}$NCYDRTDCVEX$_{23}$X$_{24}$X$_{25}$X$_{26}$PX$_{27}$VYFCCCEGNMCNEKFSYFPEMEVTQPTS (SEQ ID NO: 2) | | | |
| GAILGRSETQECLFX$_2$NANWEX$_4$X$_5$RTNQTGVEX$_7$CX$_8$GX$_9$KDKRX$_{14}$HCX$_{15}$ATWX$_{16}$NISGSIEIVKX$_{18}$GC WLDDX$_{22}$NCYDRTDCVEX$_{23}$X$_{24}$X$_{25}$X$_{26}$PX$_{27}$VYFCCCEGNMCNEKFSYFPEMEVTQPTS (SEQ ID NO: 3) | | | |
| GAILGRSETQECLFX$_2$NANWEX$_4$DRTNQTGVEX$_7$CX$_8$GX$_9$KDKRX$_{14}$HCX$_{15}$ATWX$_{16}$NISGSIEIVKX$_{18}$GC WLDDX$_{22}$NCYDRTDCVEX$_{23}$KX$_{25}$X$_{26}$PX$_{27}$VYFCCCEGNMCNEKFSYFPEMEVTQPTS (SEQ ID NO: 4) | | | |
| GAILGRSETQECLFX$_2$NANWEX$_4$DRTNQTGVEPCX$_8$GX$_9$KDKRX$_{14}$HCFATWKNISGSIEIVKX$_{18}$GCWLD DINCYDRTDCVEX$_{23}$KX$_{25}$X$_{26}$PX$_{27}$VYFCCCEGNMCNEKFSYFPEMEVTQPTS (SEQ ID NO: 5) | | | |
| $X_8$ | Y or E | $X_{22}$ | I, F, or A |
| $X_9$ | D or E | $X_{23}$ | K or T |
| $X_{10}$ | K or Q | $X_{24}$ | K or E |
| $X_{11}$ | D or A | $X_{25}$ | D or E |
| $X_{12}$ | K or A | $X_{26}$ | S or N |
| $X_{13}$ | R or A | $X_{27}$ | E or Q |
| $X_{14}$ | R or L | | |

In some embodiments of the extracellular ActRIIa variant having the sequence of SEQ ID NO: 2, $X_3$ is E, $X_6$ is R, $X_{11}$ is D, $X_{12}$ is K, $X_{13}$ is R, $X_{16}$ is K or R, $X_{17}$ is K, $X_{19}$ is W, $X_{20}$ is L, $X_{21}$ is D, and $X_{22}$ is I or F. In some embodiments of the extracellular ActRIIa variant having the sequence of SEQ ID NO: 1 or 2, $X_{17}$ is K. In some embodiments of the extracellular ActRIIa variant having the sequence of SEQ ID NOs: 1-3, $X_{17}$ is K, $X_{23}$ is T, $X_{24}$ is E, $X_{25}$ is E, and $X_{26}$ is N. In some embodiments of the extracellular ActRIIa variant having the sequence of any one of SEQ ID NOs: 1-5, $X_{17}$ is K, $X_{23}$ is T, $X_{24}$ is K, $X_{25}$ is E, and $X_{26}$ is N.

In some embodiments, a polypeptide described herein includes an extracellular ActRIIa variant having a sequence of any one of SEQ ID NOs: 6-72 (Table 2).

TABLE 2

| Extracellular ActRIIa variants having the sequences of SEQ ID NOs: 6-72 | |
|---|---|
| SEQ ID NO | Amino Acid Sequence |
| 6 | GAILGRSETQECLFYNANWELDRTNQTGVEPCEGEKDKRLHCFATWKNISGSIEIV KKGCWLDDINCYDRTDCVETKENPQVYFCCCEGNMCNEKFSYFPEMEVTQPTS |

TABLE 2-continued

Extracellular ActRIIa variants having the sequences of SEQ ID NOs: 6-72

| SEQ ID NO | Amino Acid Sequence |
|---|---|
| 7 | GAILGRSETQECLFYNANWELERTNQTGVEPCEGEKDKRLHCFATWKNISGSIEIV<br>KKGCWLDDINCYDRTDCVETKENPQVYFCCCEGNMCNEKFSYFPEMEVTQPTS |
| 8 | GAILGRSETQECLFYNANWELDRTNQTGVERCEGEKDKRLHCFATWKNISGSIEIV<br>KKGCWLDDINCYDRTDCVETKENPQVYFCCCEGNMCNEKFSYFPEMEVTQPTS |
| 9 | GAILGRSETQECLFYNANWELDRTNQTGVEPCEGEKDKRLHCYATWKNISGSIEIV<br>KKGCWLDDINCYDRTDCVETKENPQVYFCCCEGNMCNEKFSYFPEMEVTQPTS |
| 10 | GAILGRSETQECLFYNANWELDRTNQTGVEPCEGEKDKRLHCFATWRNISGSIEIV<br>KKGCWLDDINCYDRTDCVETKENPQVYFCCCEGNMCNEKFSYFPEMEVTQPTS |
| 11 | GAILGRSETQECLFYNANWELDRTNQTGVEPCEGEKDKRLHCFATWKNISGSIEIV<br>KKGCWLDDFNCYDRTDCVETKENPQVYFCCCEGNMCNEKFSYFPEMEVTQPTS |
| 12 | GAILGRSETQECLFYNANWELDRTNQTGVEPCEGEKDKRLHCFATWKNISGSIEIV<br>KKGCWLDDINCYDRTDCVETEENPQVYFCCCEGNMCNEKFSYFPEMEVTQPTS |
| 13 | GAILGRSETQECLFYNANWELERTNQTGVERCEGEKDKRLHCFATWKNISGSIEIV<br>KKGCWLDDINCYDRTDCVETKENPQVYFCCCEGNMCNEKFSYFPEMEVTQPTS |
| 14 | GAILGRSETQECLFYNANWELERTNQTGVEPCEGEKDKRLHCYATWKNISGSIEIV<br>KKGCWLDDINCYDRTDCVETKENPQVYFCCCEGNMCNEKFSYFPEMEVTQPTS |
| 15 | GAILGRSETQECLFYNANWELERTNQTGVEPCEGEKDKRLHCFATWRNISGSIEIV<br>KKGCWLDDINCYDRTDCVETKENPQVYFCCCEGNMCNEKFSYFPEMEVTQPTS |
| 16 | GAILGRSETQECLFYNANWELERTNQTGVEPCEGEKDKRLHCFATWKNISGSIEIV<br>KKGCWLDDFNCYDRTDCVETKENPQVYFCCCEGNMCNEKFSYFPEMEVTQPTS |
| 17 | GAILGRSETQECLFYNANWELERTNQTGVEPCEGEKDKRLHCFATWKNISGSIEIV<br>KKGCWLDDINCYDRTDCVETEENPQVYFCCCEGNMCNEKFSYFPEMEVTQPTS |
| 18 | GAILGRSETQECLFYNANWELDRTNQTGVERCEGEKDKRLHCYATWKNISGSIEIV<br>KKGCWLDDINCYDRTDCVETKENPQVYFCCCEGNMCNEKFSYFPEMEVTQPTS |
| 19 | GAILGRSETQECLFYNANWELDRTNQTGVERCEGEKDKRLHCFATWRNISGSIEIV<br>KKGCWLDDINCYDRTDCVETKENPQVYFCCCEGNMCNEKFSYFPEMEVTQPTS |
| 20 | GAILGRSETQECLFYNANWELDRTNQTGVERCEGEKDKRLHCFATWKNISGSIEIV<br>KKGCWLDDFNCYDRTDCVETKENPQVYFCCCEGNMCNEKFSYFPEMEVTQPTS |
| 21 | GAILGRSETQECLFYNANWELDRTNQTGVERCEGEKDKRLHCFATWKNISGSIEIV<br>KKGCWLDDINCYDRTDCVETEENPQVYFCCCEGNMCNEKFSYFPEMEVTQPTS |
| 22 | GAILGRSETQECLFYNANWELDRTNQTGVEPCEGEKDKRLHCYATWRNISGSIEIV<br>KKGCWLDDINCYDRTDCVETKENPQVYFCCCEGNMCNEKFSYFPEMEVTQPTS |
| 23 | GAILGRSETQECLFYNANWELDRTNQTGVEPCEGEKDKRLHCYATWKNISGSIEIV<br>KKGCWLDDFNCYDRTDCVETKENPQVYFCCCEGNMCNEKFSYFPEMEVTQPTS |
| 24 | GAILGRSETQECLFYNANWELDRTNQTGVEPCEGEKDKRLHCYATWKNISGSIEIV<br>KKGCWLDDINCYDRTDCVETEENPQVYFCCCEGNMCNEKFSYFPEMEVTQPTS |
| 25 | GAILGRSETQECLFYNANWELDRTNQTGVEPCEGEKDKRLHCFATWRNISGSIEIV<br>KKGCWLDDFNCYDRTDCVETKENPQVYFCCCEGNMCNEKFSYFPEMEVTQPTS |
| 26 | GAILGRSETQECLFYNANWELDRTNQTGVEPCEGEKDKRLHCFATWRNISGSIEIV<br>KKGCWLDDINCYDRTDCVETEENPQVYFCCCEGNMCNEKFSYFPEMEVTQPTS |
| 27 | GAILGRSETQECLFYNANWELDRTNQTGVEPCEGEKDKRLHCFATWKNISGSIEIV<br>KKGCWLDDFNCYDRTDCVETEENPQVYFCCCEGNMCNEKFSYFPEMEVTQPTS |
| 28 | GAILGRSETQECLFYNANWELERTNQTGVERCEGEKDKRLHCYATWKNISGSIEIV<br>KKGCWLDDINCYDRTDCVETKENPQVYFCCCEGNMCNEKFSYFPEMEVTQPTS |
| 29 | GAILGRSETQECLFYNANWELERTNQTGVERCEGEKDKRLHCFATWRNISGSIEIV<br>KKGCWLDDINCYDRTDCVETKENPQVYFCCCEGNMCNEKFSYFPEMEVTQPTS |
| 30 | GAILGRSETQECLFYNANWELERTNQTGVERCEGEKDKRLHCFATWKNISGSIEIV<br>KKGCWLDDFNCYDRTDCVETKENPQVYFCCCEGNMCNEKFSYFPEMEVTQPTS |
| 31 | GAILGRSETQECLFYNANWELERTNQTGVERCEGEKDKRLHCFATWKNISGSIEIV<br>KKGCWLDDINCYDRTDCVETEENPQVYFCCCEGNMCNEKFSYFPEMEVTQPTS |

TABLE 2-continued

Extracellular ActRIIa variants having the sequences of SEQ ID NOs: 6-72

| SEQ ID NO | Amino Acid Sequence |
| --- | --- |
| 32 | GAILGRSETQECLFYNANWELERTNQTGVEPCEGEKDKRLHCYATWRNISGSIEIV KKGCWLDDINCYDRTDCVETKENPQVYFCCCEGNMCNEKFSYFPEMEVTQPTS |
| 33 | GAILGRSETQECLFYNANWELERTNQTGVEPCEGEKDKRLHCYATWKNISGSIEIV KKGCWLDDFNCYDRTDCVETKENPQVYFCCCEGNMCNEKFSYFPEMEVTQPTS |
| 34 | GAILGRSETQECLFYNANWELERTNQTGVEPCEGEKDKRLHCYATWKNISGSIEIV KKGCWLDDINCYDRTDCVETEENPQVYFCCCEGNMCNEKFSYFPEMEVTQPTS |
| 35 | GAILGRSETQECLFYNANWELERTNQTGVEPCEGEKDKRLHCFATWRNISGSIEIV KKGCWLDDFNCYDRTDCVETKENPQVYFCCCEGNMCNEKFSYFPEMEVTQPTS |
| 36 | GAILGRSETQECLFYNANWELERTNQTGVEPCEGEKDKRLHCFATWRNISGSIEIV KKGCWLDDINCYDRTDCVETEENPQVYFCCCEGNMCNEKFSYFPEMEVTQPTS |
| 37 | GAILGRSETQECLFYNANWELERTNQTGVEPCEGEKDKRLHCFATWKNISGSIEIV KKGCWLDDFNCYDRTDCVETEENPQVYFCCCEGNMCNEKFSYFPEMEVTQPTS |
| 38 | GAILGRSETQECLFYNANWELDRTNQTGVERCEGEKDKRLHCYATWRNISGSIEIV KKGCWLDDINCYDRTDCVETKENPQVYFCCCEGNMCNEKFSYFPEMEVTQPTS |
| 39 | GAILGRSETQECLFYNANWELDRTNQTGVERCEGEKDKRLHCYATWKNISGSIEIV KKGCWLDDFNCYDRTDCVETKENPQVYFCCCEGNMCNEKFSYFPEMEVTQPTS |
| 40 | GAILGRSETQECLFYNANWELDRTNQTGVERCEGEKDKRLHCYATWKNISGSIEIV KKGCWLDDINCYDRTDCVETEENPQVYFCCCEGNMCNEKFSYFPEMEVTQPTS |
| 41 | GAILGRSETQECLFYNANWELDRTNQTGVERCEGEKDKRLHCFATWRNISGSIEIV KKGCWLDDFNCYDRTDCVETKENPQVYFCCCEGNMCNEKFSYFPEMEVTQPTS |
| 42 | GAILGRSETQECLFYNANWELDRTNQTGVERCEGEKDKRLHCFATWRNISGSIEIV KKGCWLDDINCYDRTDCVETEENPQVYFCCCEGNMCNEKFSYFPEMEVTQPTS |
| 43 | GAILGRSETQECLFYNANWELDRTNQTGVERCEGEKDKRLHCFATWKNISGSIEIV<br>KKGC<br>WLDDFNCYDRTDCVETEENPQVYFCCCEGNMCNEKFSYFPEMEVTQPTS |
| 44 | GAILGRSETQECLFYNANWELDRTNQTGVEPCEGEKDKRLHCYATWRNISGSIEIV KKGCWLDDFNCYDRTDCVETKENPQVYFCCCEGNMCNEKFSYFPEMEVTQPTS |
| 45 | GAILGRSETQECLFYNANWELDRTNQTGVEPCEGEKDKRLHCYATWRNISGSIEIV KKGCWLDDINCYDRTDCVETEENPQVYFCCCEGNMCNEKFSYFPEMEVTQPTS |
| 46 | GAILGRSETQECLFYNANWELDRTNQTGVEPCEGEKDKRLHCYATWKNISGSIEIV KKGCWLDDFNCYDRTDCVETEENPQVYFCCCEGNMCNEKFSYFPEMEVTQPTS |
| 47 | GAILGRSETQECLFYNANWELDRTNQTGVEPCEGEKDKRLHCFATWRNISGSIEIV KKGCWLDDFNCYDRTDCVETEENPQVYFCCCEGNMCNEKFSYFPEMEVTQPTS |
| 48 | GAILGRSETQECLFYNANWELERTNQTGVERCEGEKDKRLHCYATWRNISGSIEIV KKGCWLDDINCYDRTDCVETKENPQVYFCCCEGNMCNEKFSYFPEMEVTQPTS |
| 49 | GAILGRSETQECLFYNANWELERTNQTGVERCEGEKDKRLHCYATWKNISGSIEIV KKGCWLDDFNCYDRTDCVETKENPQVYFCCCEGNMCNEKFSYFPEMEVTQPTS |
| 50 | GAILGRSETQECLFYNANWELERTNQTGVERCEGEKDKRLHCYATWKNISGSIEIV KKGCWLDDINCYDRTDCVETEENPQVYFCCCEGNMCNEKFSYFPEMEVTQPTS |
| 51 | GAILGRSETQECLFYNANWELERTNQTGVERCEGEKDKRLHCFATWRNISGSIEIV KKGCWLDDFNCYDRTDCVETKENPQVYFCCCEGNMCNEKFSYFPEMEVTQPTS |
| 52 | GAILGRSETQECLFYNANWELERTNQTGVERCEGEKDKRLHCFATWRNISGSIEIV KKGCWLDDINCYDRTDCVETEENPQVYFCCCEGNMCNEKFSYFPEMEVTQPTS |
| 53 | GAILGRSETQECLFYNANWELERTNQTGVERCEGEKDKRLHCFATWKNISGSIEIV KKGCWLDDFNCYDRTDCVETEENPQVYFCCCEGNMCNEKFSYFPEMEVTQPTS |
| 54 | GAILGRSETQECLFYNANWELERTNQTGVEPCEGEKDKRLHCYATWRNISGSIEIV KKGCWLDDFNCYDRTDCVETKENPQVYFCCCEGNMCNEKFSYFPEMEVTQPTS |
| 55 | GAILGRSETQECLFYNANWELERTNQTGVEPCEGEKDKRLHCYATWRNISGSIEIV KKGCWLDDINCYDRTDCVETEENPQVYFCCCEGNMCNEKFSYFPEMEVTQPTS |
| 56 | GAILGRSETQECLFYNANWELERTNQTGVEPCEGEKDKRLHCYATWKNISGSIEIV KKGCWLDDFNCYDRTDCVETEENPQVYFCCCEGNMCNEKFSYFPEMEVTQPTS |

TABLE 2-continued

Extracellular ActRIIa variants having the sequences of SEQ ID NOs: 6-72

| SEQ ID NO | Amino Acid Sequence |
|---|---|
| 57 | GAILGRSETQECLFYNANWELERTNQTGVEPCEGEKDKRLHCFATWRNISGSIEIV KKGCWLDDFNCYDRTDCVETEENPQVYFCCCEGNMCNEKFSYFPEMEVTQPTS |
| 58 | GAILGRSETQECLFYNANWELDRTNQTGVERCEGEKDKRLHCYATWRNISGSIEIV KKGCWLDDFNCYDRTDCVETKENPQVYFCCCEGNMCNEKFSYFPEMEVTQPTS |
| 59 | GAILGRSETQECLFYNANWELDRTNQTGVERCEGEKDKRLHCYATWRNISGSIEIV KKGCWLDDINCYDRTDCVETEENPQVYFCCCEGNMCNEKFSYFPEMEVTQPTS |
| 60 | GAILGRSETQECLFYNANWELDRTNQTGVERCEGEKDKRLHCYATWKNISGSIEIV KKGCWLDDFNCYDRTDCVETEENPQVYFCCCEGNMCNEKFSYFPEMEVTQPTS |
| 61 | GAILGRSETQECLFYNANWELDRTNQTGVERCEGEKDKRLHCFATWRNISGSIEIV KKGCWLDDFNCYDRTDCVETEENPQVYFCCCEGNMCNEKFSYFPEMEVTQPTS |
| 62 | GAILGRSETQECLFYNANWELDRTNQTGVEPCEGEKDKRLHCYATWRNISGSIEIV KKGCWLDDFNCYDRTDCVETEENPQVYFCCCEGNMCNEKFSYFPEMEVTQPTS |
| 63 | GAILGRSETQECLFYNANWELERTNQTGVERCEGEKDKRLHCYATWRNISGSIEIV KKGCWLDDFNCYDRTDCVETKENPQVYFCCCEGNMCNEKFSYFPEMEVTQPTS |
| 64 | GAILGRSETQECLFYNANWELERTNQTGVERCEGEKDKRLHCYATWRNISGSIEIV KKGCWLDDINCYDRTDCVETEENPQVYFCCCEGNMCNEKFSYFPEMEVTQPTS |
| 65 | GAILGRSETQECLFYNANWELERTNQTGVERCEGEKDKRLHCYATWKNISGSIEIV KKGCWLDDFNCYDRTDCVETEENPQVYFCCCEGNMCNEKFSYFPEMEVTQPTS |
| 66 | GAILGRSETQECLFYNANWELERTNQTGVERCEGEKDKRLHCFATWRNISGSIEIV KKGCWLDDFNCYDRTDCVETEENPQVYFCCCEGNMCNEKFSYFPEMEVTQPTS |
| 67 | GAILGRSETQECLFYNANWELDRTNQTGVERCEGEKDKRLHCYATWRNISGSIEIV KKGCWLDDFNCYDRTDCVETEENPQVYFCCCEGNMCNEKFSYFPEMEVTQPTS |
| 68 | GAILGRSETQECLFYNANWELERTNQTGVEPCEGEKDKRLHCYATWRNISGSIEIV KKGCWLDDFNCYDRTDCVETEENPQVYFCCCEGNMCNEKFSYFPEMEVTQPTS |
| 69 | GAILGRSETQECLFYNANWELERTNQTGVERCEGEKDKRLHCYATWRNISGSIEIV KKGCWLDDFNCYDRTDCVETEENPQVYFCCCEGNMCNEKFSYFPEMEVTQPTS |
| 70 | GAILGRSETQECLYYNANWELERTNQTGVERCEGEQDKRLHCYATWRNISGSIEIV KKGCWLDDFNCYDRTDCVETEENPQVYFCCCEGNMCNEKFSYFPEMEVTQPTS |
| 71 | GAILGRSETQECLFYNANWELERTNQTGVERCEGEKDKRLHCYATWRNISGSIEIV KKGCWLDDFNCYDRTDCVETEENPQVYFCCCEGNMCNEKFSYFPEMEVTQPTSN P |
| 72 | GAILGRSETQECLFYNANWELERTNQTGVERCEGEKDKRLHCYATWRNISGSIEIV KKGCWLDDFNCYDRTDCVETEENPQVYFCCCEGNMCNEKFSYFPEMEVTQPTSN PVTPK |

In some embodiments, a polypeptide of the invention including an extracellular ActRIIa variant (e.g., any one of SEQ ID NOs: 1-72 (e.g., SEQ ID NOs: 6-72)) has amino acid K at position $X_{17}$. Altering the amino acid at position $X_{17}$ can result in reduced activity. For example, an ActRIIa variant having the sequence GAILGRSETQECLFYNANWELERTNQTGVERCEGEKDKRLHCYATWRNISGSIEIVAKGCWLDDFNCYD RTDCVETEENPQVYFCCCEGNMCNEKFSYFPEMEVTQPTS (SEQ ID NO: 150) has reduced activity in vivo, indicating that the substitution of A for K at $X_{17}$ is not tolerated.

In some embodiments, a polypeptide of the invention including an extracellular ActRIIa variant (e.g., any one of SEQ ID NOs: 1-72 (e.g., SEQ ID NOs: 6-72)) with the sequence TEEN at positions $X_{23}$, $X_{24}$, $X_{25}$, and $X_{26}$ can have a substitution of the amino acid K for the amino acid E at position $X_{24}$. In some embodiments, a polypeptide of the invention including an extracellular ActRIIa variant (e.g., any one of SEQ ID NOs: 1-72 (e.g., SEQ ID NOs: 6-72)) with the sequence TKEN at positions $X_{23}$, $X_{24}$, $X_{25}$, and $X_{26}$ can have a substitution of the amino acid E for the amino acid K at position $X_{24}$. Polypeptides having the sequence TEEN or TKEN at positions $X_{23}$, $X_{24}$, $X_{25}$, and $X_{26}$ have reduced or weak binding to BMP9.

In some embodiments, a polypeptide of the invention including an extracellular ActRIIa variant (e.g., any one of SEQ ID NOs: 1-70 (e.g., SEQ ID NOs: 6-70)) may further include a C-terminal extension (e.g., additional amino acids at the C-terminus). In some embodiments, the C-terminal extension is amino acid sequence NP. For example, the sequence including the C-terminal extension is SEQ ID NO: 71 (e.g., SEQ ID NO: 69 with a C-terminal extension of NP). In some embodiments, the C-terminal extension is amino acid sequence NPVTPK (SEQ ID NO: 155). For example, the sequence including the C-terminal extension is SEQ ID NO: 72 (e.g., SEQ ID NO: 69 with a C-terminal extension of NPVTPK (SEQ ID NO: 155)). The C-terminal extension can add one to six additional amino acids at the C-terminus (e.g., 1, 2, 3, 4, 5, 6 or more additional amino acids).

In some embodiments, a polypeptide of the invention including an extracellular ActRIIa variant may further include a moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin), which may be fused to the N- or C-terminus (e.g., C-terminus) of the extracellular ActRIIa variant by way of a linker or other covalent bonds. A polypeptide including an extracellular ActRIIa variant fused to an Fc domain monomer may form a dimer (e.g., homodimer or heterodimer) through the interaction between two Fc domain monomers, which combine to form an Fc domain in the dimer.

In some embodiments, an extracellular ActRIIa variant described herein does not have the sequence of any one of SEQ ID NOs: 76-96 shown in Table 3 below.

TABLE 3

Excluded Extracellular ActRIIa Variants.

| SEQ ID NO | Amino Acid Sequence |
|---|---|
| 76 | GAILGRSETQECLFFNANWEKDRTNQTGVEPCYGDKDKRRHCFATWANISGSIEIV KQGCWLDDINCYDRTDCVEKKDSPEVYFCCCEGNMCNEKFSYFPEMEVTQPTS |
| 77 | GAILGRSETQECLFFNANWAKDRTNQTGVEPCYGDKDKRRHCFATWKNISGSIEIV KQGCWLDDINCYDRTDCVEKKDSPEVYFCCCEGNMCNEKFSYFPEMEVTQPTS |
| 78 | GAILGRSETQECLFFNANWEKDATNQTGVEPCYGDKDKRRHCFATWKNISGSIEIV KQGCWLDDINCYDRTDCVEKKDSPEVYFCCCEGNMCNEKFSYFPEMEVTQPTS |
| 79 | GAILGRSETQECLFFNANWEKDRTNQTGVEPCYGDKAKRRHCFATWKNISGSIEIV KQGCWLDDINCYDRTDCVEKKDSPEVYFCCCEGNMCNEKFSYFPEMEVTQPTS |
| 80 | GAILGRSETQECLFFNANWEKDRTNQTGVEPCYGDKDARRHCFATWKNISGSIEIV KQGCWLDDINCYDRTDCVEKKDSPEVYFCCCEGNMCNEKFSYFPEMEVTQPTS |
| 81 | GAILGRSETQECLFFNANWEKDRTNQTGVEPCYGDKDKARHCFATWKNISGSIEIV KQGCWLDDINCYDRTDCVEKKDSPEVYFCCCEGNMCNEKFSYFPEMEVTQPTS |
| 82 | GAILGRSETQECLFFNANWEKDRTNQTGVEPCYGDKDKRRHCFATWKNISGSIEIV AQGCWLDDINCYDRTDCVEKKDSPEVYFCCCEGNMCNEKFSYFPEMEVTQPTS |
| 83 | GAILGRSETQECLFFNANWEKDRTNQTGVEPCYGDKDKRRHCFATWKNISGSIEIV YQGCWLDDINCYDRTDCVEKKDSPEVYFCCCEGNMCNEKFSYFPEMEVTQPTS |
| 84 | GAILGRSETQECLFFNANWEKDRTNQTGVEPCYGDKDKRRHCFATWKNISGSIEIV FQGCWLDDINCYDRTDCVEKKDSPEVYFCCCEGNMCNEKFSYFPEMEVTQPTS |
| 85 | GAILGRSETQECLFFNANWEKDRTNQTGVEPCYGDKDKRRHCFATWKNISGSIEIVI QGCWLDDINCYDRTDCVEKKDSPEVYFCCCEGNMCNEKFSYFPEMEVTQPTS |
| 86 | GAILGRSETQECLFFNANWEKDRTNQTGVEPCYGDKDKRRHCFATWKNISGSIEIV KQGCALDDINCYDRTDCVEKKDSPEVYFCCCEGNMCNEKFSYFPEMEVTQPTS |
| 87 | GAILGRSETQECLFFNANWEKDRTNQTGVEPCYGDKDKRRHCFATWKNISGSIEIV KQGCWADDINCYDRTDCVEKKDSPEVYFCCCEGNMCNEKFSYFPEMEVTQPTS |
| 88 | GAILGRSETQECLFFNANWEKDRTNQTGVEPCYGDKDKRRHCFATWKNISGSIEIV KQGCWLKDINCYDRTDCVEKKDSPEVYFCCCEGNMCNEKFSYFPEMEVTQPTS |
| 89 | GAILGRSETQECLFFNANWEKDRTNQTGVEPCYGDKDKRRHCFATWKNISGSIEIV KQGCWLRDINCYDRTDCVEKKDSPEVYFCCCEGNMCNEKFSYFPEMEVTQPTS |
| 90 | GAILGRSETQECLFFNANWEKDRTNQTGVEPCYGDKDKRRHCFATWKNISGSIEIV KQGCWLADINCYDRTDCVEKKDSPEVYFCCCEGNMCNEKFSYFPEMEVTQPTS |
| 91 | GAILGRSETQECLFFNANWEKDRTNQTGVEPCYGDKDKRRHCFATWKNISGSIEIV KQGCWLFDINCYDRTDCVEKKDSPEVYFCCCEGNMCNEKFSYFPEMEVTQPTS |
| 92 | GAILGRSETQECLFFNANWEKDRTNQTGVEPCYGDKDKRRHCFATWKNISGSIEIV KQGCWLGDINCYDRTDCVEKKDSPEVYFCCCEGNMCNEKFSYFPEMEVTQPTS |
| 93 | GAILGRSETQECLFFNANWEKDRTNQTGVEPCYGDKDKRRHCFATWKNISGSIEIV KQGCWLMDINCYDRTDCVEKKDSPEVYFCCCEGNMCNEKFSYFPEMEVTQPTS |
| 94 | GAILGRSETQECLFFNANWEKDRTNQTGVEPCYGDKDKRRHCFATWKNISGSIEIV KQGCWLNDINCYDRTDCVEKKDSPEVYFCCCEGNMCNEKFSYFPEMEVTQPTS |
| 95 | GAILGRSETQECLFFNANWEKDRTNQTGVEPCYGDKDKRRHCFATWKNISGSIEIV KQGCWLIDINCYDRTDCVEKKDSPEVYFCCCEGNMCNEKFSYFPEMEVTQPTS |
| 96 | GAILGRSETQECLFFNANWEKDRTNQTGVEPCYGDKDKRRHCFATWKNISGSIEIV KQGCWLDDANCYDRTDCVEKKDSPEVYFCCCEGNMCNEKFSYFPEMEVTQPTS |

Furthermore, in some embodiments, a polypeptide described herein has a serum half-life of at least 7 days in humans. The polypeptide may bind to bone morphogenetic protein 9 (BMP9) with a $K_D$ of 200 pM or higher. The polypeptide may bind to activin A with a $K_D$ of 10 pM or higher. In some embodiments, the polypeptide does not bind to BMP9 or activin A. In some embodiments, the polypeptide binds to activin and/or myostatin and exhibits reduced (e.g., weak) binding to BMP9. In some embodiments, the polypeptide that has reduced or weak binding to BMP9 has the sequence TEEN or TKEN at positions $X_{23}$, $X_{24}$, $X_{25}$, and $X_{26}$.

Additionally, in some embodiments, the polypeptide may bind to human BMP9 with a $K_D$ of about 200 pM or higher (e.g., a $K_D$ of about 200, 300, 400, 500, 600, 700, 800, or 900 pM or higher, e.g., a $K_D$ of about 1, 2, 3, 4, 5, 6, 7, 8, 9, 10, 20, 30, 40, or 50 nM or higher, e.g., a $K_D$ of between about 200 pM and about 50 nM). In some embodiments, the polypeptide does not substantially bind to human BMP9. In some embodiments, the polypeptide may bind to human activin A with a $K_D$ of about 800 pM or less (e.g., a $K_D$ of about 800, 700, 600, 500, 400, 300, 200, 100, 90, 80, 70, 60, 50, 40, 30, 20, 10, 9, 8, 7, 6, 5, 4, 3, 2, or 1 pM or less, e.g., a $K_D$ of between about 800 pM and about 200 pM). In some embodiments, the polypeptide may bind to human activin B with a $K_D$ of 800 pM or less (e.g., a $K_D$ of about 800, 700, 600, 500, 400, 300, 200, 100, 90, 80, 70, 60, 50, 40, 30, 20, 10, 9, 8, 7, 6, 5, 4, 3, 2, or 1 pM or less, e.g., a $K_D$ of between about 800 pM and about 200 pM) The polypeptide may also bind to growth and differentiation factor 11 (GDF-11) with a $K_D$ of approximately 5 pM or higher (e.g., a $K_D$ of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 pM or higher).

II. Fc Domains

In some embodiments, a polypeptide described herein may include an extracellular ActRIIa variant fused to an Fc domain monomer of an immunoglobulin or a fragment of an Fc domain to increase the serum half-life of the polypeptide. A polypeptide including an extracellular ActRIIa variant fused to an Fc domain monomer may form a dimer (e.g., homodimer or heterodimer) through the interaction between two Fc domain monomers, which form an Fc domain in the dimer. As conventionally known in the art, an Fc domain is the protein structure that is found at the C-terminus of an immunoglobulin. An Fc domain includes two Fc domain monomers that are dimerized by the interaction between the $C_H3$ antibody constant domains. A wild-type Fc domain forms the minimum structure that binds to an Fc receptor, e.g., FcγRI, FcγRIIa, FcγRIIb, FcγRIIIa, FcγRIIIb, FcγRIV. In some embodiments, an Fc domain may be mutated to lack effector functions, typical of a "dead" Fc domain. For example, an Fc domain may include specific amino acid substitutions that are known to minimize the interaction between the Fc domain and an Fcγ receptor. In some embodiments, an Fc domain is from an IgG1 antibody and includes amino acid substitutions L234A, L235A, and G237A. In some embodiments, an Fc domain is from an IgG1 antibody and includes amino acid substitutions D265A, K322A, and N434A. The aforementioned amino acid positions are defined according to Kabat (Sequences of Proteins of Immunological Interest, 5th Ed. Public Health Service, National Institutes of Health, Bethesda, Md. (1991)). The Kabat numbering of amino acid residues may be determined for a given antibody by alignment at regions of homology of the sequence of the antibody with a "standard" Kabat numbered sequence. Furthermore, in some embodiments, an Fc domain does not induce any immune system-related response. For example, the Fc domain in a dimer of a polypeptide including an extracellular ActRIIa variant fused to an Fc domain monomer may be modified to reduce the interaction or binding between the Fc domain and an Fcγ receptor. The sequence of an Fc domain monomer that may be fused to an extracellular ActRIIa variant is shown below (SEQ ID NO: 97):

```
THTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYK

CKVSNKALPVPIEKTISKAKGQPREPQVYTLPPSREEMTKNQVSLTCLV

KGFYPSDIAVEWESNGQPENNYKTTPPVLDSDGPFFLYSKLTVDKSRWQ

QGNVFSCSVMHEALHNHYTQKSLSLSPGK
```

In some embodiments, an Fc domain is from an IgG1 antibody and includes amino acid substitutions L12A, L13A, and G15A, relative to the sequence of SEQ ID NO: 97. In some embodiments, an Fc domain is from an IgG1 antibody and includes amino acid substitutions D43A, K100A, and N212A, relative to the sequence of SEQ ID NO: 97. In some embodiments, an extracellular ActRIIa variant described herein (e.g., an extracellular ActRIIa variant having the sequence of any one of SEQ ID NOs: 1-72 (e.g., SEQ ID NOs: 6-72)) may be fused to the N- or C-terminus of an Fc domain monomer (e.g., SEQ ID NO: 97) through conventional genetic or chemical means, e.g., chemical conjugation. If desired, a linker (e.g., a spacer) can be inserted between the extracellular ActRIIa variant and the Fc domain monomer. The Fc domain monomer can be fused to the N- or C-terminus (e.g., C-terminus) of the extracellular ActRIIa variant.

In some embodiments, a polypeptide described herein may include an extracellular ActRIIa variant fused to an Fc domain. In some embodiments, the Fc domain contains one or more amino acid substitutions that reduce or inhibit Fc domain dimerization. In some embodiments, the Fc domain contains a hinge domain. The Fc domain can be of immunoglobulin antibody isotype IgG, IgE, IgM, IgA, or IgD. Additionally, the Fc domain can be an IgG subtype (e.g., IgG1, IgG2a, IgG2b, IgG3, or IgG4). The Fc domain can also be a non-naturally occurring Fc domain, e.g., a recombinant Fc domain.

Methods of engineering Fc domains that have reduced dimerization are known in the art. In some embodiments, one or more amino acids with large side-chains (e.g., tyrosine or tryptophan) may be introduced to the $C_H3$-$C_H3$ dimer interface to hinder dimer formation due to steric clash. In other embodiments, one or more amino acids with small side-chains (e.g., alanine, valine, or threonine) may be introduced to the $C_H3$-$C_H3$ dimer interface to remove favorable interactions. Methods of introducing amino acids with large or small side-chains in the $C_H3$ domain are described in, e.g., Ying et al. (*J Biol Chem.* 287:19399-19408, 2012), U.S. Patent Publication No. 2006/0074225, U.S. Pat. Nos. 8,216,805 and 5,731,168, Ridgway et al. (*Protein Eng.* 9:617-612, 1996), Atwell et al. (*J Mol Biol.* 270:26-35, 1997), and Merchant et al. (*Nat Biotechnol.* 16:677-681, 1998), all of which are incorporated herein by reference in their entireties.

In yet other embodiments, one or more amino acid residues in the $C_H3$ domain that make up the $C_H3$-$C_H3$ interface between two Fc domains are replaced with positively-charged amino acid residues (e.g., lysine, arginine, or histidine) or negatively-charged amino acid residues (e.g., aspartic acid or glutamic acid) such that the interaction becomes electrostatically unfavorable depending on the specific charged amino acids introduced. Methods of introducing charged amino acids in the $C_H3$ domain to disfavor or prevent dimer formation are described in, e.g., Ying et al. (J Biol Chem. 287:19399-19408, 2012), U.S. Patent Publication Nos. 2006/0074225, 2012/0244578, and 2014/0024111, all of which are incorporated herein by reference in their entireties.

In some embodiments of the invention, an Fc domain includes one or more of the following amino acid substitutions: T366W, T366Y, T394W, F405W, Y349T, Y349E, Y349V, L351T, L351H, L351N, L352K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1. In one particular embodiment, an Fc domain includes the amino acid substitution T366W, relative to the sequence of human IgG1. The sequence of wild-type Fc domain is shown in SEQ ID NO: 151.

III. Albumin-Binding Peptide

In some embodiments, a polypeptide described herein may include an extracellular ActRIIa variant fused to a serum protein-binding peptide. Binding to serum protein peptides can improve the pharmacokinetics of protein pharmaceuticals.

As one example, albumin-binding peptides that can be used in the methods and compositions described here are generally known in the art. In one embodiment, the albumin binding peptide includes the sequence DICLPRWGCLW (SEQ ID NO: 152).

In the present invention, albumin-binding peptides may be joined to the N- or C-terminus (e.g., C-terminus) of an extracellular ActRIIa variant described herein (e.g., an extracellular ActRIIa variant having the sequence of any one of SEQ ID NOs: 1-72 (e.g., SEQ ID NOs: 6-72)) to increase the serum half-life of the extracellular ActRIIa variant. In some embodiments, an albumin-binding peptide is joined, either directly or through a linker, to the N- or C-terminus of an extracellular ActRIIa variant.

In some embodiments, an extracellular ActRIIa variant described herein (e.g., an extracellular ActRIIa variant having the sequence of any one of SEQ ID NOs: 1-72 (e.g., SEQ ID NOs: 6-72)) may be fused to the N- or C-terminus of albumin-binding peptide (e.g., SEQ ID NO: 152) through conventional genetic or chemical means, e.g., chemical conjugation. If desired, a linker (e.g., a spacer) can be inserted between the extracellular ActRIIa variant and the albumin-binding peptide. Without being bound to a theory, it is expected that inclusion of an albumin-binding peptide in an extracellular ActRIIa variant described herein may lead to prolonged retention of the therapeutic protein through its binding to serum albumin.

IV. Fibronectin Domain

In some embodiments, a polypeptide described herein may include an extracellular ActRIIa variant fused to fibronectin domains. Binding to fibronectin domains can improve the pharmacokinetics of protein pharmaceuticals.

Fibronectin domain is a high molecular weight glycoprotein of the extracellular matrix, or a fragment thereof, that binds to, e.g., membrane-spanning receptor proteins such as integrins and extracellular matrix components such as collagens and fibrins. In some embodiments of the present invention, a fibronectin domain is joined to the N- or C-terminus (e.g., C-terminus) of an extracellular ActRIIa variant described herein (e.g., an extracellular ActRIIa variant having the sequence of any one of SEQ ID NOs: 1-72 (e.g., SEQ ID NOs: 6-72)) to increase the serum half-life of the extracellular ActRIIa variant. A fibronectin domain can be joined, either directly or through a linker, to the N- or C-terminus of an extracellular ActRIIa variant.

As one example, fibronectin domains that can be used in the methods and compositions described here are generally known in the art. In one embodiment, the fibronectin domain is a fibronectin type III domain (SEQ ID NO: 153) having amino acids 610-702 of the sequence of UniProt ID NO: P02751. In another embodiment, the fibronectin domain is an adnectin protein.

In some embodiments, an extracellular ActRIIa variant described herein (e.g., an extracellular ActRIIa variant having the sequence of any one of SEQ ID NOs: 1-72 (e.g., SEQ ID NOs: 6-72)) may be fused to the N- or C-terminus of a fibronectin domain (e.g., SEQ ID NO: 153) through conventional genetic or chemical means, e.g., chemical conjugation. If desired, a linker (e.g., a spacer) can be inserted between the extracellular ActRIIa variant and the fibronectin domain. Without being bound to a theory, it is expected that inclusion of a fibronectin domain in an extracellular ActRIIa variant described herein may lead to prolonged retention of the therapeutic protein through its binding to integrins and extracellular matrix components such as collagens and fibrins.

V. Serum Albumin

In some embodiments, a polypeptide described herein may include an extracellular ActRIIa variant fused to serum albumin. Binding to serum albumins can improve the pharmacokinetics of protein pharmaceuticals.

Serum albumin is a globular protein that is the most abundant blood protein in mammals. Serum albumin is produced in the liver and constitutes about half of the blood serum proteins. It is monomeric and soluble in the blood. Some of the most crucial functions of serum albumin include transporting hormones, fatty acids, and other proteins in the body, buffering pH, and maintaining osmotic pressure needed for proper distribution of bodily fluids between blood vessels and body tissues. In preferred embodiments, serum albumin is human serum albumin. In some embodiments of the present invention, a human serum albumin is joined to the N- or C-terminus (e.g., C-terminus) of an extracellular ActRIIa variant described herein (e.g., an extracellular ActRIIa variant having the sequence of any one of SEQ ID NOs: 1-72 (e.g., SEQ ID NOs: 6-72)) to increase the serum half-life of the extracellular ActRIIa variant. A human serum albumin can be joined, either directly or through a linker, to the N- or C-terminus of an extracellular ActRIIa variant.

As one example, serum albumins that can be used in the methods and compositions described herein are generally known in the art. In one embodiment, the serum albumin includes the sequence of UniProt ID NO: P02768 (SEQ ID NO: 154).

In some embodiments, an extracellular ActRIIa variant described herein (e.g., an extracellular ActRIIa variant having the sequence of any one of SEQ ID NOs: 1-72 (e.g., SEQ ID NOs: 6-72)) may be fused to the N- or C-terminus of a human serum albumin (e.g., SEQ ID NO: 154) through conventional genetic or chemical means, e.g., chemical conjugation. If desired, a linker (e.g., a spacer) can be inserted between the extracellular ActRIIa variant and the human serum albumin. Without being bound to a theory, it is expected that inclusion of a human serum albumin in an extracellular ActRIIa variant described herein may lead to prolonged retention of the therapeutic protein.

VI. Linkers

A polypeptide described herein may include an extracellular ActRIIa variant (e.g., an extracellular ActRIIa variant having a sequence of any one of SEQ ID NOs: 1-72 (e.g., SEQ ID NOs: 6-72)) fused to a moiety by way of a linker. In some embodiments, the moiety increases stability of the polypeptide. Exemplary moieties include an Fc domain monomer, a wild-type Fc domain, an Fc domain with amino acid substitutions (e.g., one or more substitutions that reduce dimerization), an albumin-binding peptide, a fibronectin domain, or a human serum albumin. In the present invention, a linker between a moiety (e.g., an Fc domain monomer (e.g., the sequence of SEQ ID NO: 97), a wild-type Fc domain (e.g., SEQ ID NO: 151), an Fc domain with amino acid substitutions (e.g., one or more substitutions that reduce dimerization), an albumin-binding peptide (e.g., SEQ ID NO: 152), a fibronectin domain (e.g., SEQ ID NO: 153), or a human serum albumin (e.g., SEQ ID NO: 154)) and an extracellular ActRIIa variant (e.g., an extracellular ActRIIa variant having the sequence of any one of SEQ ID NOs: 1-72 (e.g., SEQ ID NOs: 6-72)), can be an amino acid spacer including 1-200 amino acids. Suitable peptide spacers are known in the art, and include, for example, peptide linkers containing flexible amino acid residues such as glycine, alanine, and serine. In some embodiments, a spacer can contain motifs, e.g., multiple or repeating motifs, of GA, GS, GG, GGA, GGS, GGG, GGGA (SEQ ID NO: 98), GGGS (SEQ ID NO: 99), GGGG (SEQ ID NO: 100), GGGGA (SEQ ID NO: 101), GGGGS (SEQ ID NO: 102), GGGGG (SEQ ID NO: 103), GGAG (SEQ ID NO: 104), GGSG (SEQ ID NO: 105), AGGG (SEQ ID NO: 106), or SGGG (SEQ ID NO: 107). In some embodiments, a spacer can contain 2 to 12 amino acids including motifs of GA or GS, e.g., GA, GS, GAGA (SEQ ID NO: 108), GSGS (SEQ ID NO: 109), GAGAGA (SEQ ID NO: 110), GSGSGS (SEQ ID NO: 111), GAGAGAGA (SEQ ID NO: 112), GSGSGSGS (SEQ ID NO: 113), GAGAGAGAGA (SEQ ID NO: 114), GSGSGSGSGS (SEQ ID NO: 115), GAGAGAGAGAGA (SEQ ID NO: 116), and GSGSGSGSGSGS (SEQ ID NO: 117). In some embodiments, a spacer can contain 3 to 12 amino acids including motifs of GGA or GGS, e.g., GGA, GGS, GGAGGA (SEQ ID NO: 118), GGSGGS (SEQ ID NO: 119), GGAGGAGGA (SEQ ID NO: 120), GGSGGSGGS (SEQ ID NO: 121), GGAGGAGGAGGA (SEQ ID NO: 122), and GGSGGSGGSGGS (SEQ ID NO: 123). In yet some embodiments, a spacer can contain 4 to 12 amino acids including motifs of GGAG (SEQ ID NO: 104), GGSG (SEQ ID NO: 105), e.g., GGAG (SEQ ID NO: 104), GGSG (SEQ ID NO: 105), GGAGGGAG (SEQ ID NO: 124), GGSGGGSG (SEQ ID NO: 125), GGAGGGAGGGAG (SEQ ID NO: 126), and GGSGGGSGGGSG (SEQ ID NO: 127). In some embodiments, a spacer can contain motifs of GGGGA (SEQ ID NO: 101) or GGGGS (SEQ ID NO: 102), e.g., GGGGAGGGGAGGGGA (SEQ ID NO: 128) and GGGGSGGGGSGGGGS (SEQ ID NO: 129). In some embodiments of the invention, an amino acid spacer between a moiety (e.g., an Fc domain monomer, a wild-type Fc domain, an Fc domain with amino acid substitutions (e.g., one or more substitutions that reduce dimerization), an albumin-binding peptide, a fibronectin domain, or a human serum albumin) and an extracellular ActRIIa variant (e.g., an extracellular ActRIIa variant having the sequence of any one of SEQ ID NOs: 1-72 (e.g., SEQ ID NOs: 6-72)) may be GGG, GGGA (SEQ ID NO: 98), GGGG (SEQ ID NO: 100), GGGAG (SEQ ID NO: 130), GGGAGG (SEQ ID NO: 131), or GGGAGGG (SEQ ID NO: 132).

In some embodiments, a spacer can also contain amino acids other than glycine, alanine, and serine, e.g., AAAL (SEQ ID NO: 133), AAAK (SEQ ID NO: 134), AAAR (SEQ ID NO: 135), EGKSSGSGSESKST (SEQ ID NO: 136), GSAGSAAGSGEF (SEQ ID NO: 137), AEAAAKEAAAKA (SEQ ID NO: 138), KESGSVSSEQLAQFRSLD (SEQ ID NO: 139), GENLYFQSGG (SEQ ID NO: 140), SACYCELS (SEQ ID NO: 141), RSIAT (SEQ ID NO: 142), RPACKIPNDLKQKVMNH (SEQ ID NO: 143), GGSAGGSGSGSSGGSSGASGTGTAGGTGSGSGTGSG (SEQ ID NO: 144), AAANSSIDLISVPVDSR (SEQ ID NO: 145), or GGSGGGSEGGGSEGGGSEGGGSEGGGSEGGGSGGGS (SEQ ID NO: 146). In some embodiments, a spacer can contain motifs, e.g., multiple or repeating motifs, of EAAAK (SEQ ID NO: 147). In some embodiments, a spacer can contain motifs, e.g., multiple or repeating motifs, of proline-rich sequences such as $(XP)_n$, in which X may be any amino acid (e.g., A, K, or E) and n is from 1-5, and PAPAP (SEQ ID NO: 148).

The length of the peptide spacer and the amino acids used can be adjusted depending on the two protein involved and the degree of flexibility desired in the final protein fusion polypeptide. The length of the spacer can be adjusted to ensure proper protein folding and avoid aggregate formation.

VII. Vectors, Host Cells, and Protein Production

The polypeptides of the invention can be produced from a host cell. A host cell refers to a vehicle that includes the necessary cellular components, e.g., organelles, needed to express the polypeptides and fusion polypeptides described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, or the like). The choice of nucleic acid vectors depends in part on the host cells to be used. Generally, preferred host cells are of either eukaryotic (e.g., mammalian) or prokaryotic (e.g., bacterial) origin.

Nucleic Acid Vector Construction and Host Cells

A nucleic acid sequence encoding the amino acid sequence of a polypeptide of the invention may be prepared by a variety of methods known in the art. These methods include, but are not limited to, oligonucleotide-mediated (or site-directed) mutagenesis and PCR mutagenesis. A nucleic acid molecule encoding a polypeptide of the invention may be obtained using standard techniques, e.g., gene synthesis. Alternatively, a nucleic acid molecule encoding a wild-type extracellular ActRIIa may be mutated to include specific amino acid substitutions using standard techniques in the art, e.g., QuikChange™ mutagenesis. Nucleic acid molecules can be synthesized using a nucleotide synthesizer or PCR techniques.

A nucleic acid sequence encoding a polypeptide of the invention may be inserted into a vector capable of replicating and expressing the nucleic acid molecule in prokaryotic or eukaryotic host cells. Many vectors are available in the art and can be used for the purpose of the invention. Each vector may include various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells may be used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NSO, Sp2/0, VERY, BHK, MDCK, W138, BT483, Hs578T, HTB2, BT20, T47D, NSO (a murine myeloma cell line that does not endogenously produce any immunoglobulin chains), CRL7030, and HsS78Bst cells. In some embodiments, *E. coli* cells may also be used as host cells for the invention. Examples of *E. coli* strains include, but are not limited to, *E. coli* 294 (ATCC®31,446), *E. coli* A 1776 (ATCC®31,537, *E. coli* BL21 (DE3) (ATCC® BAA-1025), and *E. coli* RV308 (ATCC®31,608). Different host cells have characteristic and specific mechanisms for the posttranslational processing and modification of protein products (e.g., glycosylation). Appropriate cell lines or host systems may be chosen to ensure the correct modification and processing of the polypeptide expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols* (*Methods in Molecular Biology*), Humana Press; 2nd ed. 2004 and Vladimir Voynov and Justin A. Caravella (eds.) *Therapeutic Proteins: Methods and Protocols* (*Methods in Molecular Biology*) Humana Press; 2nd ed. 2012.

Protein Production, Recovery, and Purification

Host cells used to produce the polypeptides of the invention may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10%. The pH of the medium is generally from about 6.8 to 7.4, e.g., 7.0, depending mainly on the host organism. If an inducible promoter is used in the expression vector of the invention, protein expression is induced under conditions suitable for the activation of the promoter.

In some embodiments, depending on the expression vector and the host cells used, the expressed protein may be secreted from the host cells (e.g., mammalian host cells) into the cell culture media. Protein recovery may involve filtering the cell culture media to remove cell debris. The proteins may be further purified. A polypeptide of the invention may be purified by any method known in the art of protein purification, for example, by chromatography (e.g., ion exchange, affinity, and size-exclusion column chromatography), centrifugation, differential solubility, or by any other standard technique for the purification of proteins. For example, the protein can be isolated and purified by appropriately selecting and combining affinity columns such as Protein A column (e.g., POROS Protein A chromatography) with chromatography columns (e.g., POROS HS-50 cation exchange chromatography), filtration, ultra filtration, salting-out and dialysis procedures.

In other embodiments, host cells may be disrupted, e.g., by osmotic shock, sonication, or lysis, to recover the expressed protein. Once the cells are disrupted, cell debris may be removed by centrifugation or filtration. In some instances, a polypeptide can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from influenza hemagglutinin protein (Wilson et al., Cell 37:767, 1984).

Alternatively, the polypeptides of the invention can be produced by the cells of a subject (e.g., a human), e.g., in the context of gene therapy, by administrating a vector (such as a viral vector (e.g., a retroviral vector, adenoviral vector, poxviral vector (e.g., vaccinia viral vector, such as Modified Vaccinia Ankara (MVA)), adeno-associated viral vector, and alphaviral vector)) containing a nucleic acid molecule encoding the polypeptide of the invention. The vector, once inside a cell of the subject (e.g., by transformation, transfection, electroporation, calcium phosphate precipitation, direct microinjection, infection, etc.) will promote expression of the polypeptide, which is then secreted from the cell. If treatment of a disease or disorder is the desired outcome, no further action may be required. If collection of the protein is desired, blood may be collected from the subject and the protein purified from the blood by methods known in the art.

VIII. Pharmaceutical Compositions and Preparations

The invention features pharmaceutical compositions that include the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)). In some embodiments, a pharmaceutical composition of the invention includes a polypeptide including an extracellular ActRIIa variant (e.g., an extracellular ActRIIa variant having the sequence of any one of SEQ ID NOs: 1-70 (e.g., SEQ ID NOs: 6-70)) with a C-terminal extension (e.g., 1, 2, 3, 4, 5, 6 or more additional amino acids) as the therapeutic protein. In some embodiments, a pharmaceutical composition of the invention includes a polypeptide including an extracellular ActRIIa variant (e.g., an extracellular ActRIIa variant having the sequence of any one of SEQ ID NOs: 1-72 (e.g., SEQ ID NOs: 6-72)) fused to a moiety (e.g., Fc domain monomer, or a dimer thereof, a wild-type Fc domain, an Fc domain with amino acid substitutions (e.g., one or more substitutions that reduce dimerization), an albumin-binding peptide, a fibronectin domain, or a human serum albumin) as the therapeutic protein. In some embodiments, a pharmaceutical composition of the invention including a polypeptide of the invention may be used in combination with other agents (e.g., therapeutic biologics and/or small molecules) or compositions in a therapy. In addition to a therapeutically effective amount of the polypeptide, the pharmaceutical composition may include one or more pharmaceutically acceptable carriers or excipients, which can be formulated by methods known to those skilled in the art. In some embodiments, a pharmaceutical composition of the invention includes a nucleic acid molecule (DNA or RNA, e.g., mRNA) encoding a polypeptide of the invention, or a vector containing such a nucleic acid molecule.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (3rd ed.) Taylor & Francis Group, CRC Press (2015).

The pharmaceutical compositions of the invention may be prepared in microcapsules, such as hydroxylmethylcellulose or gelatin-microcapsule and poly-(methylmethacrylate) microcapsule. The pharmaceutical compositions of the invention may also be prepared in other drug delivery systems such as liposomes, albumin microspheres, microemulsions, nano-particles, and nanocapsules. Such techniques are described in Remington: The Science and Practice of Pharmacy 22$^{th}$ edition (2012). The pharmaceutical compositions to be used for in vivo administration must be sterile. This is readily accomplished by filtration through sterile filtration membranes.

The pharmaceutical compositions of the invention may also be prepared as a sustained-release formulation. Suitable examples of sustained-release preparations include semipermeable matrices of solid hydrophobic polymers containing the polypeptides of the invention. Examples of sustained release matrices include polyesters, hydrogels, polyactides, copolymers of L-glutamic acid and γ ethyl-L-glutamate, non-degradable ethylene-vinyl acetate, degradable lactic acid-glycolic acid copolymers such as LUPRON DEPOT™, and poly-D-(−)-3-hydroxybutyric acid. Some sustained-release formulations enable release of molecules over a few months, e.g., one to six months, while other formulations release pharmaceutical compositions of the invention for shorter time periods, e.g., days to weeks.

The pharmaceutical composition may be formed in a unit dose form as needed. The amount of active component, e.g., a polypeptide of the invention, included in the pharmaceutical preparations is such that a suitable dose within the designated range is provided (e.g., a dose within the range of 0.01-100 mg/kg of body weight).

The pharmaceutical composition for gene therapy can be in an acceptable diluent, or can include a slow release matrix in which the gene delivery vehicle is imbedded. If hydrodynamic injection is used as the delivery method, the pharmaceutical composition containing a nucleic acid molecule encoding a polypeptide described herein or a vector (e.g., a viral vector) containing the nucleic acid molecule is delivered rapidly in a large fluid volume intravenously. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

IX. Routes, Dosage, and Administration

Pharmaceutical compositions that include the polypeptides of the invention as the therapeutic proteins may be formulated for, e.g., intravenous administration, parenteral administration, subcutaneous administration, intramuscular administration, intra-arterial administration, intrathecal administration, or intraperitoneal administration. The pharmaceutical composition may also be formulated for, or administered via, oral, nasal, spray, aerosol, rectal, or vaginal administration. For injectable formulations, various effective pharmaceutical carriers are known in the art. See, e.g., ASHP Handbook on Injectable Drugs, Toissel, 18th ed. (2014).

In some embodiments, a pharmaceutical composition that includes a nucleic acid molecule encoding a polypeptide of the invention or a vector containing such nucleic acid molecule may be administered by way of gene delivery. Methods of gene delivery are well-known to one of skill in the art. Vectors that may be used for in vivo gene delivery and expression include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors. In some embodiments, mRNA molecules encoding polypeptides of the invention may be administered directly to a subject.

In some embodiments of the present invention, nucleic acid molecules encoding a polypeptide described herein or vectors containing such nucleic acid molecules may be administered using a hydrodynamic injection platform. In the hydrodynamic injection method, a nucleic acid molecule encoding a polypeptide described herein is put under the control of a strong promoter in an engineered plasmid (e.g., a viral plasmid). The plasmid is often delivered rapidly in a large fluid volume intravenously. Hydrodynamic injection uses controlled hydrodynamic pressure in veins to enhance cell permeability such that the elevated pressure from the rapid injection of the large fluid volume results in fluid and plasmid extravasation from the vein. The expression of the nucleic acid molecule is driven primarily by the liver. In mice, hydrodynamic injection is often performed by injection of the plasmid into the tail vein. In certain embodiments, mRNA molecules encoding a polypeptide described herein may be administered using hydrodynamic injection.

The dosage of the pharmaceutical compositions of the invention depends on factors including the route of administration, the disease to be treated, and physical characteristics, e.g., age, weight, general health, of the subject. A pharmaceutical composition of the invention may include a dosage of a polypeptide of the invention ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 30 mg/kg and, in a more specific embodiment, about 0.3 to about 30 mg/kg. The dosage may be adapted by the physician in accordance with conventional factors such as the extent of the disease and different parameters of the subject.

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, and oral dosage forms (e.g., ingestible solutions, drug release capsules). Generally, therapeutic proteins are dosed at 0.1-100 mg/kg, e.g., 1-50 mg/kg. Pharmaceutical compositions that include a polypeptide of the invention may be administered to a subject in need thereof, for example, one or more times (e.g., 1-10 times or more) daily, weekly, biweekly, monthly, bimonthly, quarterly, biannually, annually, or as medically necessary. In some embodiments, pharmaceutical compositions that include a polypeptide of the invention may be administered to a subject in need thereof weekly, biweekly, monthly, bimonthly, or quarterly. Dosages may be provided in either a single or multiple dosage regimens. The timing between administrations may decrease as the medical condition improves or increase as the health of the patient declines.

X. Methods of Treatment

The invention is based on the discovery that substituting amino acids from the extracellular portion of ActRIIb into the extracellular portion ActRIIa yields ActRIIa variants with improved properties. The ActRIIa variants generated by introducing residues from ActRIIb into ActRIIa retain the beneficial properties of ActRIIa, such as longer serum half-life and low binding affinity to BMP9, and gain some of the beneficial properties of ActRIIb, such as increased binding to activins A and B (see Table 4) and an ability to increase muscle mass (see Examples 1-3 and 5-6). These ActRIIa variant properties make for a useful therapeutic that can compete with endogenous activin receptors for ligand binding. As the ActRIIa variants contain the extracellular portion of the receptor, they will be soluble and able to bind to and sequester ligands (e.g., activins A and B, myostatin, GDF11) without activating intracellular signaling pathways. Therefore, the extracellular ActRIIa variants can be used to treat diseases or conditions in which elevated activin signaling has been implicated (e.g., associated with increased expression of activin receptors or activin receptor ligands). For example, loss of myostatin has been shown to increase skeletal muscle mass, suggesting that myostatin inhibits skeletal muscle growth. It follows that treatment with a therapeutic agent that binds to myostatin and reduces its interaction with endogenous receptors could be a viable approach for increasing muscle mass. Indeed, extracellular ActRIIa variants of the invention increase muscle mass in mice (see Examples 1-3 and 5-6). These data indicate that the extracellular ActRIIa variants described herein can be used to increase muscle mass and treat subjects with diseases or conditions that result in muscle weakness or atrophy.

Moreover, these data provide a compelling reason to use the extracellular ActRIIa variants of the invention to treat other diseases or conditions associated with elevated expression of activin receptors or activin receptor ligands, such as metabolic diseases (e.g., obesity, Type-1 diabetes, and Type-2 diabetes). Many studies have shown that increasing muscle mass is one way to reduce body fat and/or body weight, indicating that the extracellular ActRIIa variants described herein can be used to treat metabolic diseases (e.g., obesity, Type-1 diabetes, and Type-2 diabetes) indirectly by increasing muscle mass. However, as activin receptors and activin receptor ligands have been shown to be increased in in obese mice and humans, the extracellular ActRIIa variants described herein can be used to treat obesity by reducing elevated activin receptor signaling (e.g., by binding to and sequestering endogenous activin receptor ligands, e.g., activins and myostatin).

The invention provides compositions and methods of treatment that may be used to increase muscle mass and strength in a subject in need thereof. In some embodiments, the subject may have a disease that results in muscle weakness or atrophy (e.g., skeletal muscle weakness or atrophy). In some embodiments, the methods described herein are directed to affecting myostatin, activin, and/or BMP9 signaling in a subject having a disease or condition involving weakness and atrophy of muscles. In some embodiments, a polypeptide including an extracellular ActRIIa variant described herein reduces or inhibits the binding of myostatin, activin, and/or BMP9 to their receptors, e.g., ActRIIa, ActRIIb, and BMPRII (e.g., ActRIIa). In some embodiments, affecting myostatin, activin, and/or BMP9 signaling (e.g., reducing or inhibiting the binding of myostatin, activin, and/or BMP9 to their receptors, e.g., ActRIIa, ActRIIb, and BMPRII (e.g., ActRIIa)) results in an increase in the subject's muscle mass.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be administered to a subject to increase muscle mass, or to affect myostatin, activin, and/or BMP9 signaling in the subject. In some embodiments, the methods described herein increase bone mineral density of the subject. In some embodiments, the methods described herein do not cause any vascular complications in the subject, such as increased vascular permeability or leakage. In some embodiments of the methods described herein, the subject has a disease or condition involving weakness and atrophy of muscles (e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia).

The invention also includes methods of treating a subject having Duchenne muscular dystrophy (DMD), facioscapulohumeral muscular dystrophy (FSHD), inclusion body myositis (IBM), amyotrophic lateral sclerosis (ALS), sarcopenia, or cancer cachexia by administering to the subject a polypeptide described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)).

The compositions and methods described herein can also be used to treat and/or prevent medical conditions, such as metabolic diseases, e.g., obesity and diabetes (Type-1 and Type-2 diabetes). In some embodiments, the subject may have a disease that results in obesity. In some embodiments, the methods described herein are directed to affecting myostatin, activin, and/or BMP9 signaling in a subject having obesity, diabetes (Type-1 and Type-2 diabetes), or a disease or condition that results in obesity. In some embodiments, a polypeptide including an extracellular ActRIIa variant described herein reduces or inhibits the binding of myostatin, activin, and/or BMP9 to their receptors, e.g., ActRIIa, ActRIIb, and BMPRII (e.g., ActRIIa). In some embodiments, affecting myostatin, activin, and/or BMP9 signaling (e.g., reducing or inhibiting the binding of myostatin, activin, and/or BMP9 to their receptors, e.g., ActRIIa, ActRIIb, and BMPRII (e.g., ActRIIa)) results in a reduction in the subject's body fat (e.g., amount of body fat or body fat percentage), a reduction in the subject's body weight or body weight gain, a reduction in fasting insulin levels, an increase in glucose clearance, or an increase in insulin sensitivity (e.g., a reduction in insulin resistance).

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be administered to a subject to prevent the development of obesity (e.g., in patients at risk of developing obesity, e.g., patients who are overweight, who have a family history of obesity, or who have other medical conditions or genetic risk factors linked to increased risk of obesity) and/or to treat patients already diagnosed with obesity. For example, administration of the extracellular ActRIIa variant (e.g., an extracellular ActRIIa variant having the sequence of any one of SEQ ID NOs: 1-72 (e.g., SEQ ID NOs: 6-72)) to a subject may help to reduce the body weight of the subject by decreasing the amount of fat. In some embodiments, the extracellular ActRIIa variant decreases the amount of fat while maintaining or increasing the amount of lean mass.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be used to prevent the development of diabetes (e.g., Type-1 and Type-2 diabetes) and/or to treat patients already diagnosed with diabetes. Patients who are likely to develop diabetes, e.g., individuals with genetic predisposition, family history of diabetes, prediabetes, association with other autoimmune diseases, or other metabolic diseases, may be administered the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) prophylactically, such that the extracellular ActRIIa polypeptides may maintain the normal function and health of p-cells and prevent or delay the autoimmune inflammatory damage to p-cells. In other embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be administered to individuals before they would be diagnosed with diabetes (e.g., Type-1 and Type-2 diabetes) or develop clinical symptoms of diabetes, e.g., high blood glucose level, high fasting insulin level, insulin resistance, polyuria, polydipsia, and polyphagia. In some embodiments, the extracellular ActRIIa polypeptides may be administered to patients prior to the patients needing insulin. In yet other embodiments, the administration of extracellular ActRIIa polypeptides may delay or postpone the need for insulin treatment in diabetic patients. For example, administration of the extracellular ActRIIa polypeptides of the invention to a subject may help to increase the rate of glucose clearance from the blood.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be administered to a subject to prevent the development of and/or treat patients with obesity or diabetes (e.g., Type-1 and Type-2 diabetes), or to affect myostatin, activin, and/or BMP9 signaling in the subject (e.g., to reduce or inhibit the binding of activin, myostatin, and/or BMP9 to their receptors). In some embodiments, the methods described herein reduce body fat (e.g., reduce the amount of subcutaneous and/or visceral fat, reduce adiposity, reduce the weights of epididymal and perirenal fat pads, or reduce body fat percentage). In some embodiments, the methods described herein reduce body weight or reduce body weight gain (e.g., reduce the percentage of body weight gain). In some embodiments, the methods described herein reduce the proliferation of adipose cells. In some embodiments, the methods described herein reduce LDL. In some embodiments, the methods described herein reduce triglycerides. In some embodiments, the methods described herein improve the serum lipid profile of the subject. In some embodiments, the methods described herein reduce body fat without reducing lean mass (e.g., do not affect lean mass or increase lean mass). In some embodiments, the methods described herein reduce body fat and increase muscle mass. In some embodiments, the methods described herein reduce blood glucose levels (e.g., fasting glucose levels) or and/or increase glucose clearance. In some embodiments, the methods described herein reduce fasting insulin levels and/or improve insulin sensitivity (e.g., reduce insulin resistance). In some embodiments, the methods described herein regulate insulin biosynthesis and/or secretion from p-cells. In some embodiments, the methods described herein do not affect the appetite for food intake. In some embodiments, the methods described herein do not cause any vascular complications in the subject, such as increased vascular permeability or leakage.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) decrease body fat, decrease body weight, or increase insulin sensitivity and/or glucose clearance by increasing muscle mass.

In any of the methods described herein, a polypeptide including an extracellular ActRIIa variant (e.g., an extracellular ActRIIa variant having the sequence of any one of SEQ ID NOs: 1-71 (e.g., SEQ ID NOs: 6-71)) that further includes a C-terminal extension of one to six amino acids (e.g., 1, 2, 3, 4, 5, 6 or more amino acids) may be used as the therapeutic protein. In any of the methods described herein, a dimer (e.g., homodimer or heterodimer) of a polypeptide including an extracellular ActRIIa variant (e.g., an extracellular ActRIIa variant having the sequence of any one of SEQ ID NOs: 1-72 (e.g., SEQ ID NOs: 6-72)) fused to a moiety (e.g., an Fc domain monomer, a wild-type Fc domain, an Fc domain with amino acid substitutions (e.g., one more substitutions that reduce dimerization), an albumin-binding peptide, a fibronectin domain, or a human serum albumin) may be used as the therapeutic protein. Nucleic acids encoding the polypeptides described herein, or vectors containing said nucleic acids can also be administered according to any of the methods described herein. In any of the methods described herein, the polypeptide, nucleic acid, or vector can be administered as part of a pharmaceutical composition.

EXAMPLES

Example 1—Effect of Extracellular ActRIIa Variants on Body Weight

C57Bl/6 mice received a single hydrodynamic injection of a plasmid construct encoding one of the following six polypeptides (n=10/group):

(1) human Fc (hFc), (2) extracellular ActRIIa (SEQ ID NO: 73) fused to the N-terminus of hFc through a GGG linker;

(3) extracellular ActRIIb (SEQ ID NO: 74) fused to the N-terminus of hFc through a GGG linker;

(4) extracellular ActRIIa variant (SEQ ID NO: 69) fused to the N-terminus of hFc through a GGG linker; and (5) extracellular ActRIIb variant (SEQ ID NO: 149) fused to the N-terminus of hFc through a GGG linker.

Figure 2A:
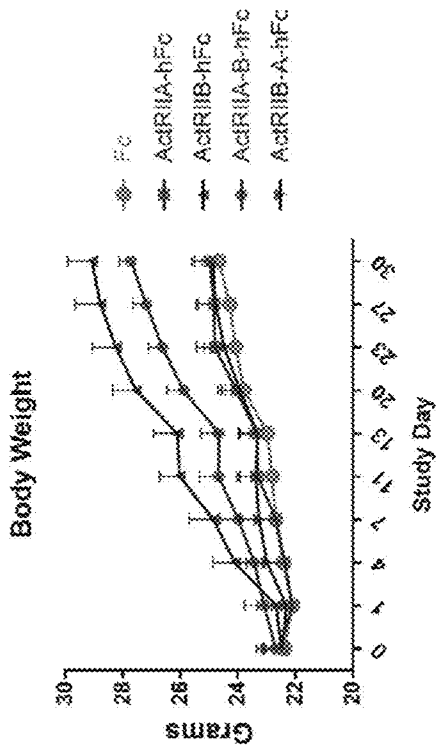

100 μg of plasmid construct was delivered in a volume of 10% body weight over 5-8 seconds. The high volume and short period of injection provides the pressure needed to introduce the plasmid into the liver cells where the plasmid will be expressed, specifically the proteins of interest are expressed under a strong and ubiquitous promoter. The protein of interest is secreted under the endogenous machinery of the liver cells and circulates freely. Mice were weighted twice weekly for 30 days and measurements were recorded as absolute body weight (BW) in grams and as a percent of body weight change from baseline measurements (FIGS. 2A and 2B, respectively).

Example 2—Effect of Extracellular ActRIIa Variants on Muscle Mass

Mice received a single hydrodynamic injection of a plasmid construct encoding one of the following six polypeptides (n=10/group):

(1) human Fc (hFc), (2) extracellular ActRIIa (SEQ ID NO: 73) fused to the N-terminus of hFc through a GGG linker;

(3) extracellular ActRIIb (SEQ ID NO: 74) fused to the N-terminus of hFc through a GGG linker;

(4) extracellular ActRIIa variant (SEQ ID NO: 69) fused to the N-terminus of hFc through a GGG linker; and (5) extracellular ActRIIb variant (SEQ ID NO: 149) fused to the N-terminus of hFc through a GGG linker.

Figure 3B:
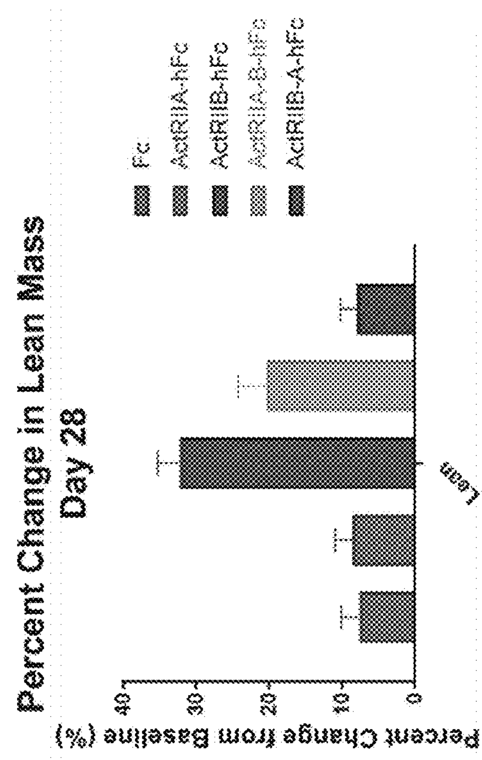
FIGS. 3A and 3B are bar graphs showing the effects of extracellular ActRIIa variants on muscle mass.
Figure 3A:
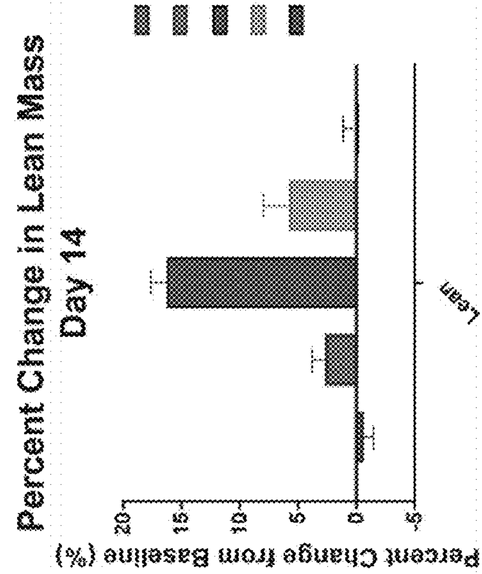

100 μg of plasmid construct was delivered in a volume of 10% body weight over 5-8 seconds. The high volume and short period of injection provides the pressure needed to introduce the plasmid into the liver cells where the plasmid will be expressed, specifically the proteins of interest are expressed under a strong and ubiquitous promoter. The protein of interest is secreted under the endogenous machinery of the liver cells and circulates freely. On study days 0 (baseline), 14, and 28, mice underwent NMR analysis for determination of lean mass using a MiniSpec LF90 NMR analyzer (Bruker, Woodlands, Tex.). The percent lean mass changes from baseline were recorded on days 14 and 28 (FIGS. 3A and 3B).

Example 3—Effect of Extracellular ActRIIa Variants on Body Weight when Administered as Purified Recombinant Protein Female C57Bl/6 mice (Taconic Biosciences, Hudson N.Y.) received an intraperitoneal injection of tris-buffered saline vehicle or one of the following five purified recombinant polypeptides at a dosage of 10 mg/kg twice weekly for four weeks (n=10/group):

(1) tris-buffered saline vehicle, (2) extracellular ActRIIa (SEQ ID NO: 73) fused to the N-terminus of hFc through a GGG linker;

(3) extracellular ActRIIb (SEQ ID NO: 74) fused to the N-terminus of hFc through a GGG linker;

(4) extracellular ActRIIa/b variant (SEQ ID NO: 69) fused to the N-terminus of hFc through a GGG linker;

(5) extracellular ActRIIa/bΔ9 variant (SEQ ID NO: 58) fused to the N-terminus of hFc through a GGG linker; and (6) extracellular ActRII a/bΔ9 min variant (SEQ ID NO: 6) fused to the N-terminus of hFc through a GGG linker.

Purified recombinant protein was made by transient expression in HEK293 cell and purified from the conditioned media using Protein-A Sepharose chromatography.

Figure 4A:
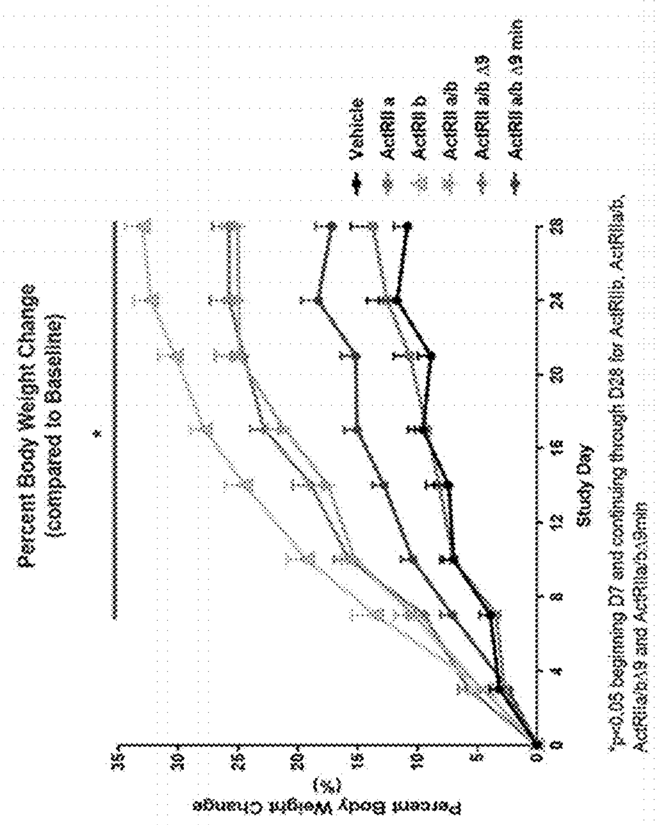
FIG. 4A is a scatter plot showing the effects of extracellular ActRIIa variants on body weight. Mice received an intraperitoneal injection of the indicated purified recombinant ActRIIa variant or a vehicle control twice weekly for four weeks.
Figure 4B:
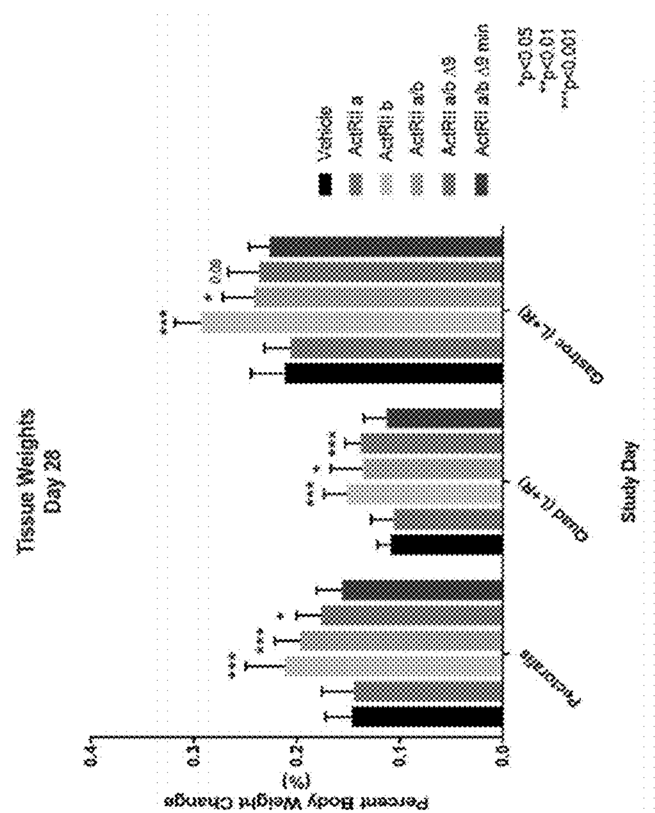
FIG. 4B is a bar graph showing the effects of extracellular ActRIIa variants on individual muscle weights by tissue analysis.

Following four weeks of dosing the mice were humanely sacrificed and necropsy was performed. Necropsy included collection of weights for total body, and the gastrocnemius, pectoralis, and quadriceps muscles. Statistical analysis of muscle/body weight data was performed in GraphPad Prism 7 (GraphPad Software, La Jolla Calif.) (FIGS. 4A and 4B, respectively).

Example 4—Evaluation of ActRIIa Variants Binding Affinity by Surface Plasmon Resonance (SPR)

The Biacore 3000 was used to measure the kinetics of the interactions between the ActRIIa variants and the ligands Activin A, Activin B, growth differentiation factor 11 (GDF11), and BMP-9. ActRIIa variants were expressed and purified according to the methodology described in Example 3. The ActRIIa variants were immobilized on the chip (CM4 or CM5) with capture antibodies (anti-mouse from GEGE) in flow cells 2-4 to ensure proper orientation. Flow cell 1 was used as a reference cell to subtract any nonspecific binding and bulk effects. HBS-EP+ buffer from GE Healthcare™ was used as a running buffer. Each ligand was run in a concentration series at 40 μl/min to avoid mass transport effects. The data was analyzed using Scrubber2 by BioLogic™ Software to calculate the $K_D$ of each interaction (Table 4).

TABLE 4

Comparison of ActRIIa variant binding affinity ($K_D$) to various ligands

| Vehicle | Activin A ($K_D$) N/A | Activin B ($K_D$) N/A | GDF-11 ($K_D$) N/A | BMP-9 ($K_D$) N/A |
|---|---|---|---|---|
| ActRIIa (SEQ ID NO: 73) | 1 nM | 373 pM | 81 pM | 25 nM |
| ActRIIb (SEQ ID NO: 74) | 63 pM | 23 pM | 115 pM | 278 pM |
| ActRIIa/b variant (SEQ ID NO: 69) | 542 pM | 103 pM | 186 pM | 4 nM |
| ActRIIb/a variant (SEQ ID NO: 149) | No Binding | No Binding | No Binding | No Binding |

TABLE 4-continued

Comparison of ActRIIa variant binding affinity ($K_D$) to various ligands

| Vehicle | Activin A ($K_D$) N/A | Activin B ($K_D$) N/A | GDF-11 ($K_D$) N/A | BMP-9 ($K_D$) N/A |
|---|---|---|---|---|
| ActRIIa/bΔ9 variant (SEQ ID NO: 58) | 213 pM | 12.3 pM | 115 pM | 10 nM |
| ActRIIa/bΔ9 min variant (SEQ ID NO: 6) | 310 pM | 88 pM | 114 pM | 17 nM |
| ActRIIa/b+ variant (SEQ ID NO: 150) | 242 pM | 282 pM | No dissociation | 26 nM |
| ActRIIa/bΔ9m2 variant (SEQ ID NO: 38) | 170 pM | 104 pM | 222 pM | 13-18 nM |
| ActRIIa/bΔ9m3 variant (SEQ ID NO: 41) | 71 pM | 72.5 pM | 117 pM | 1.2 nM |
| ActRIIa/bΔ9m4 variant (SEQ ID NO: 44) | 375 pM | 254 pM | 394 pM | 14-20 nM |
| ActRIIa/bmax1 variant (SEQ ID NO: 70) | 232 pM | 97 pM | 236 pM | 5.6 nM |
| ActRIIa/bmax2 variant (SEQ ID NO: 71) | 135 pM | 39 pM | 113 pM | 5 nM |
| ActRIIa/bmax3 variant (SEQ ID NO: 72) | 89 pM | 43 pM | 214 pM | 3.3 nM |

*Not done in HDI, but recombinant protein demonstrates the BW result is similar to ActRIIa/b

Example 5—Effect of Extracellular ActRIIa Variants on Body and Muscle Weight C57Bl/6 mice received a single hydrodynamic injection of a plasmid construct encoding one of the following twelve polypeptides (n=10/group):

(1) vehicle;

(2) pLEV113-ActRIIa (19-127) (SEQ ID NO: 73) fused to the N-terminus of hFc through a GGG linker;

(3) pLEV113-ActRIIb (41-155) (SEQ ID NO: 74) fused to the N-terminus of hFc through a GGG linker;

(4) pLEV113-ActRIIa/b (SEQ ID NO: 69) fused to the N-terminus of hFc through a GGG linker;

(5) pLEV113-ActRIIb/a (SEQ ID NO: 149) fused to the N-terminus of hFc through a GGG linker;

(6) pLEV113-ActRIIa/b+ (SEQ ID NO: 150) fused to the N-terminus of hFc through a GGG linker;

(7) pLEV113-ActRIIa/b-delta 9m2 (SEQ ID NO: 38) fused to the N-terminus of hFc through a GGG linker;

(8) pLEV113-ActRIIa/b-delta 9m3 (SEQ ID NO: 41) fused to the N-terminus of hFc through a GGG linker;

(9) pLEV113-ActRIIa/b-delta 9m4 (SEQ ID NO: 44) fused to the N-terminus of hFc through a GGG linker;

(10) pLEV113-ActRIIa/bmax1 (SEQ ID NO: 70) fused to the N-terminus of hFc through a GGG linker;

(11) pLEV113-ActRIIa/bmax2 (SEQ ID NO: 71) fused to the N-terminus of hFc through a GGG linker; and

(12) pLEV113-ActRIIa/bmax1 (SEQ ID NO: 72) fused to the N-terminus of hFc through a GGG linker.

Figure 5A:
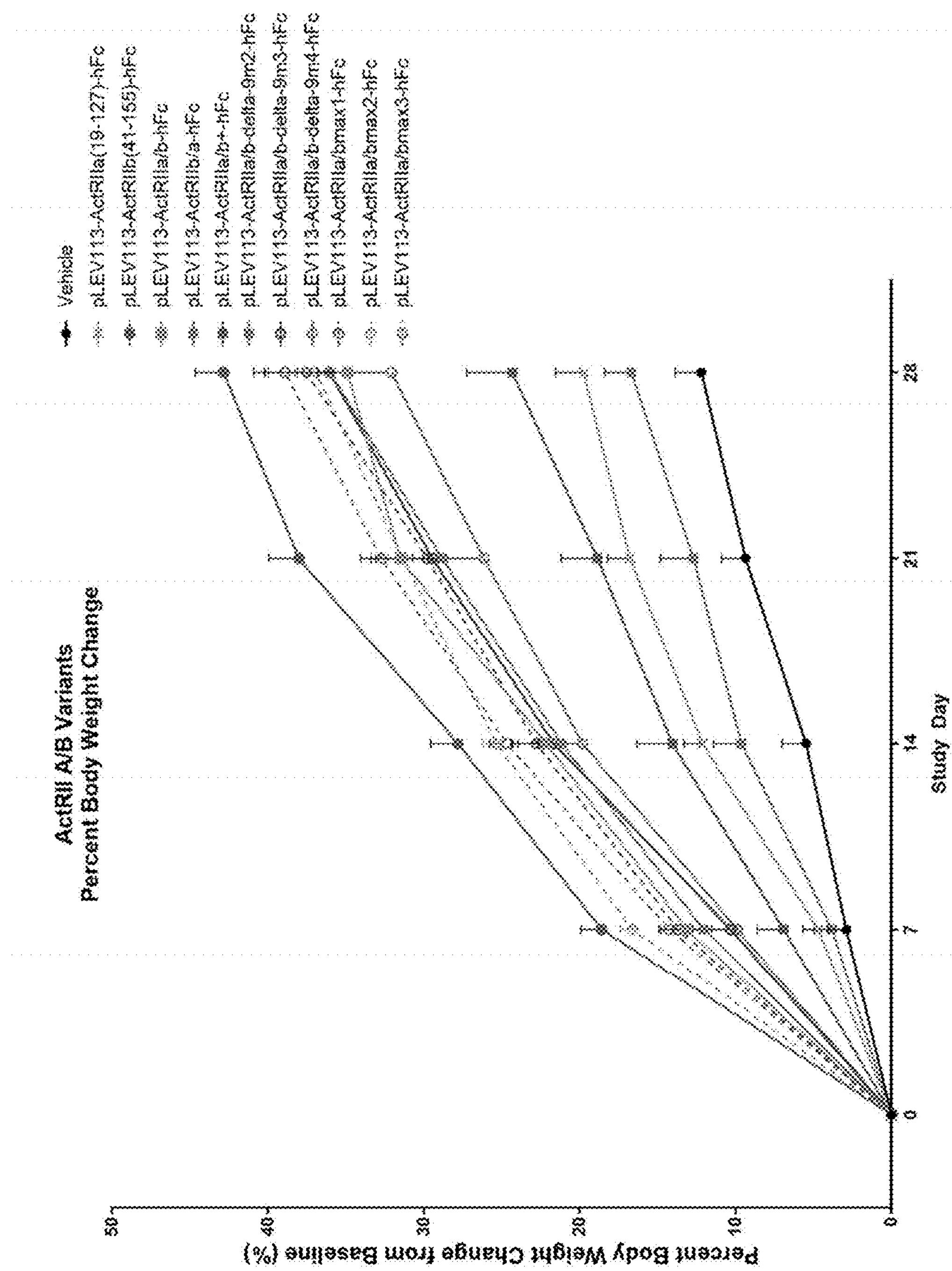
FIG. 5A is a scatter plot showing the effects of extracellular ActRIIa variants on body weight during the course of the study. Mice received a single hydrodynamic injection of a plasmid construct encoding the indicated ActRIIa variant or a control plasmid.
Figure 5B:
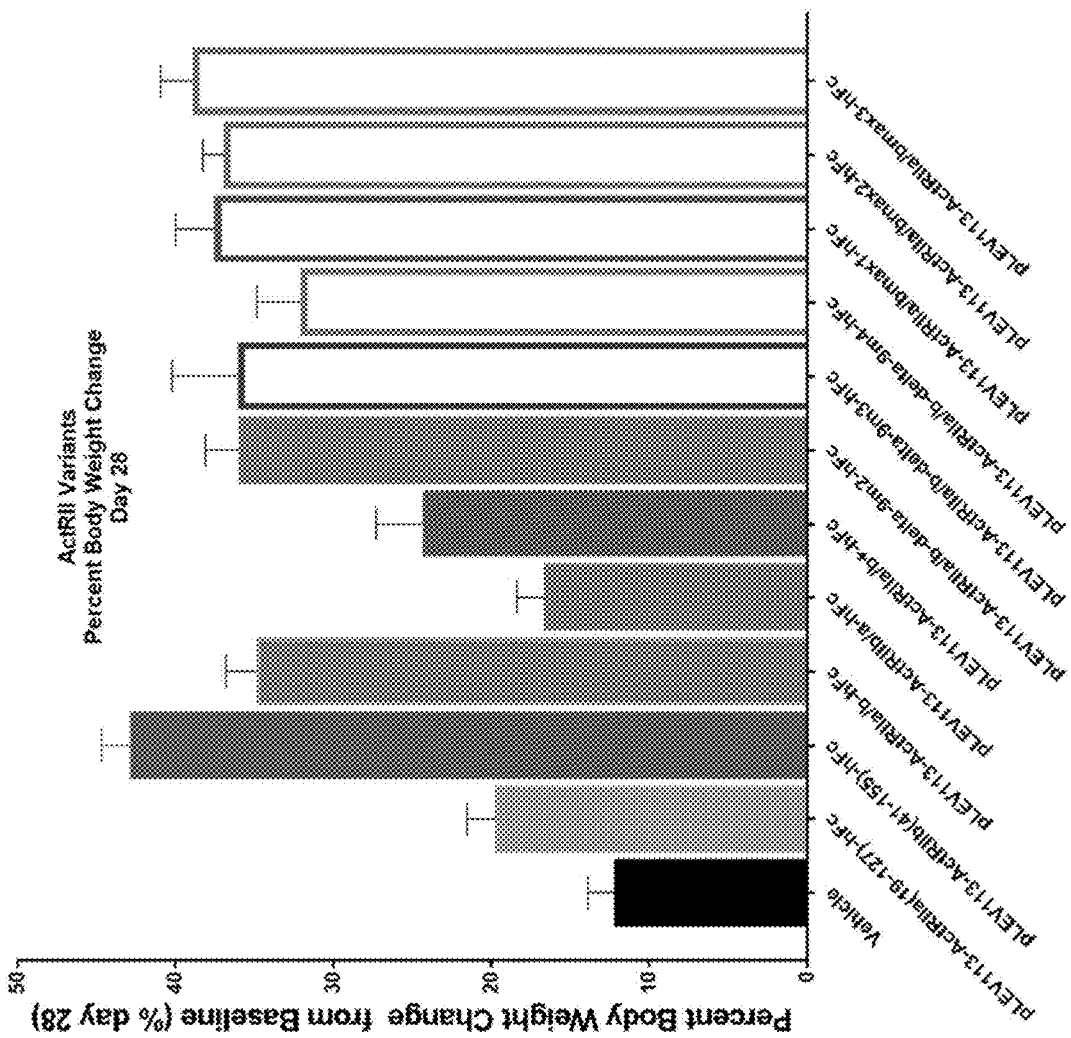
FIG. 5B is a bar graph showing the effects of extracellular ActRIIa variants on body weight at the end of 28 days.
Figure 6B:
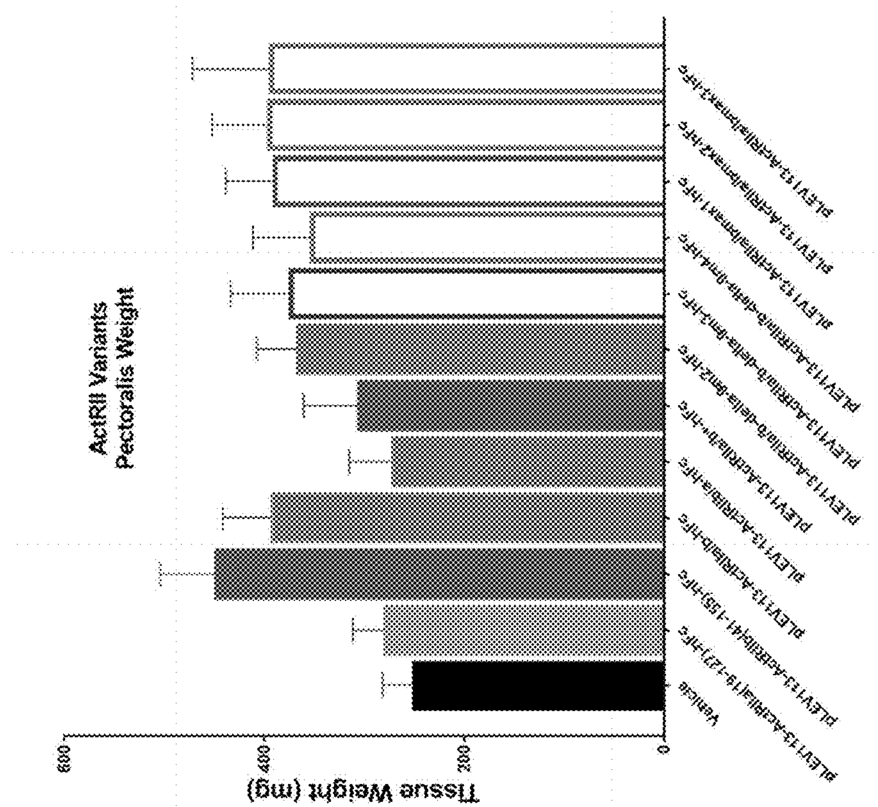
FIGS. 6A and 6B are bar graphs showing the effects of extracellular ActRIIa variants on body weight by tissue analysis.
Figure 6A:
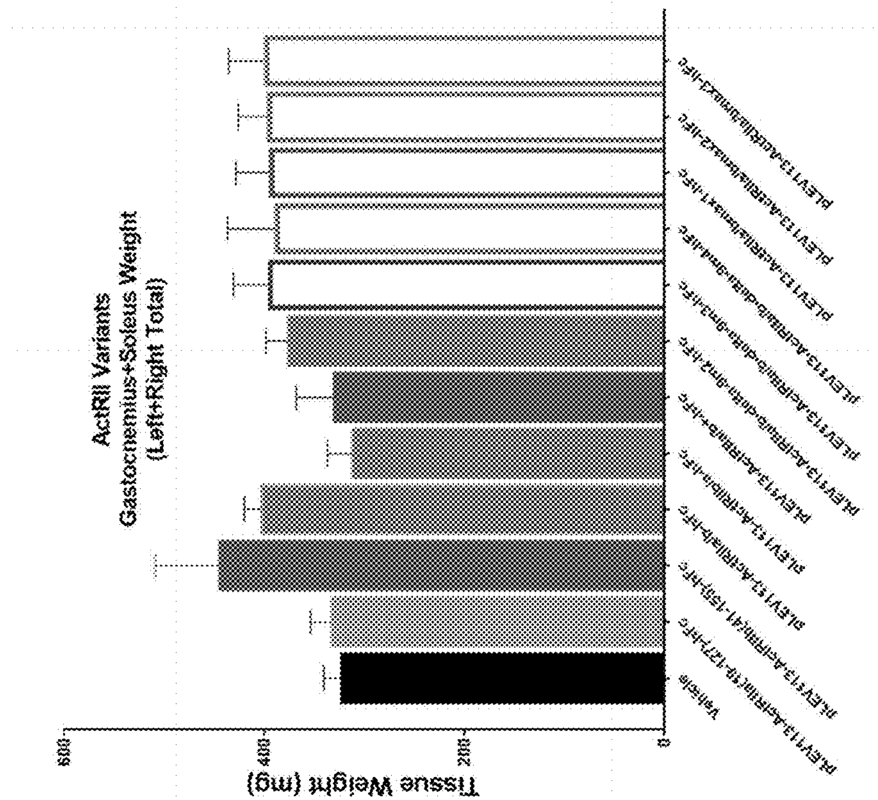

100 μg of plasmid construct was delivered in a volume of 10% body weight over 5-8 seconds. The high volume and short period of injection provides the pressure needed to introduce the plasmid into the liver cells where the plasmid will be expressed, specifically the proteins of interest are expressed under a strong and ubiquitous promoter. The protein of interest is secreted under the endogenous machinery of the liver cells and circulates freely. Mice were weighted twice weekly for 30 days and measurements were recorded as absolute body weight (BW) in grams and as a percent of body weight change from baseline measurements (FIGS. 5A and 5B, respectively). Muscles were also weighed at the end of the study and measurements were recorded in grams (FIGS. 6A and 6B).

Figure 7A:
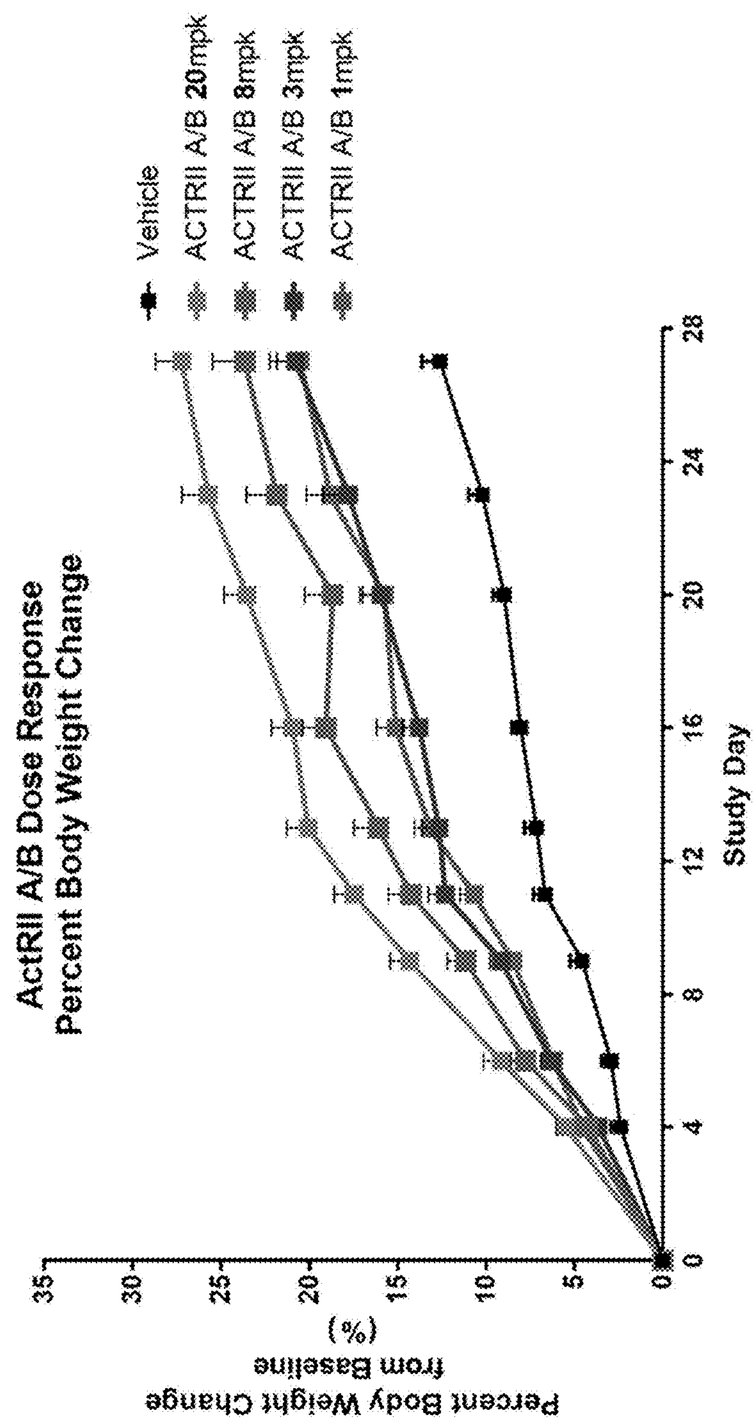
FIGS. 7A and 7B are scatter plots showing the effects of different doses of extracellular ActRIIa variants on body weight. Mice received an intraperitoneal injection of the indicated purified recombinant ActRIIa variant or a vehicle control twice weekly for four weeks.
Figure 7B:
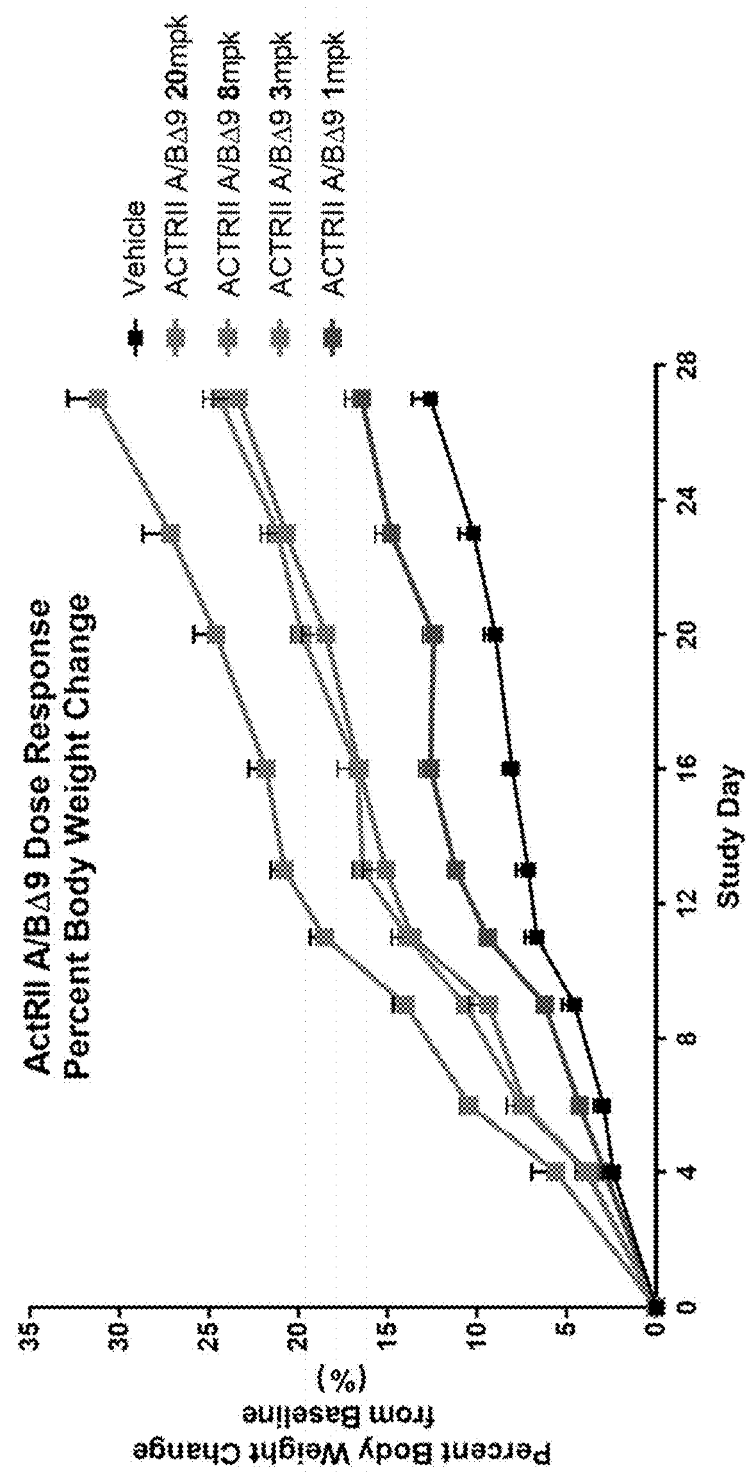
Figure 8A:
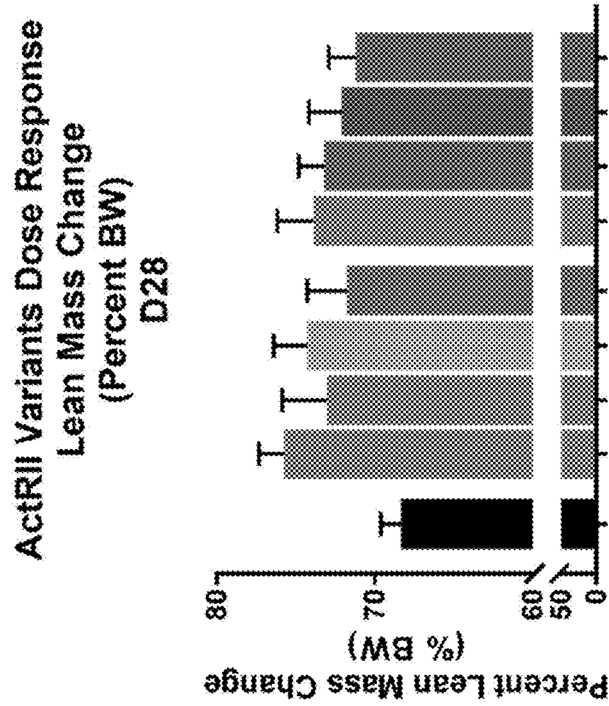
FIGS. 8A and 8B are bar graphs showing the effects of different doses of extracellular ActRIIa variants on muscle mass (FIG. 8A) and fat mass (FIG. 8B).
Figure 8B:
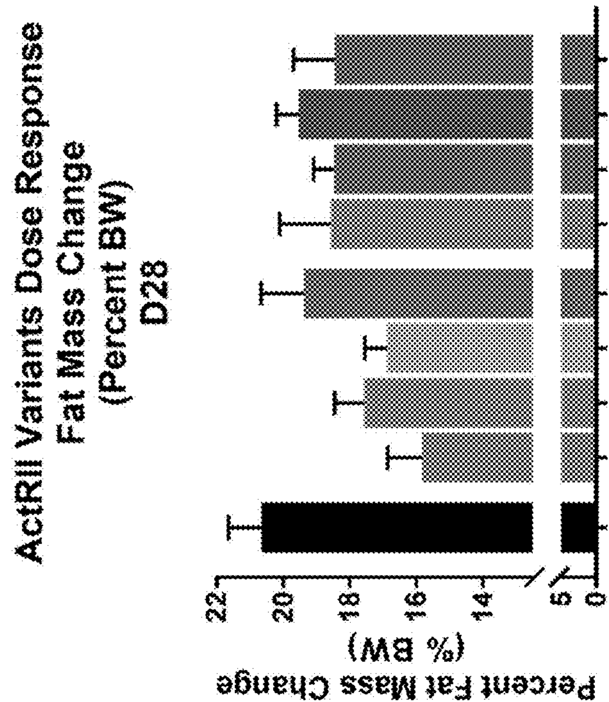
Figure 9A:
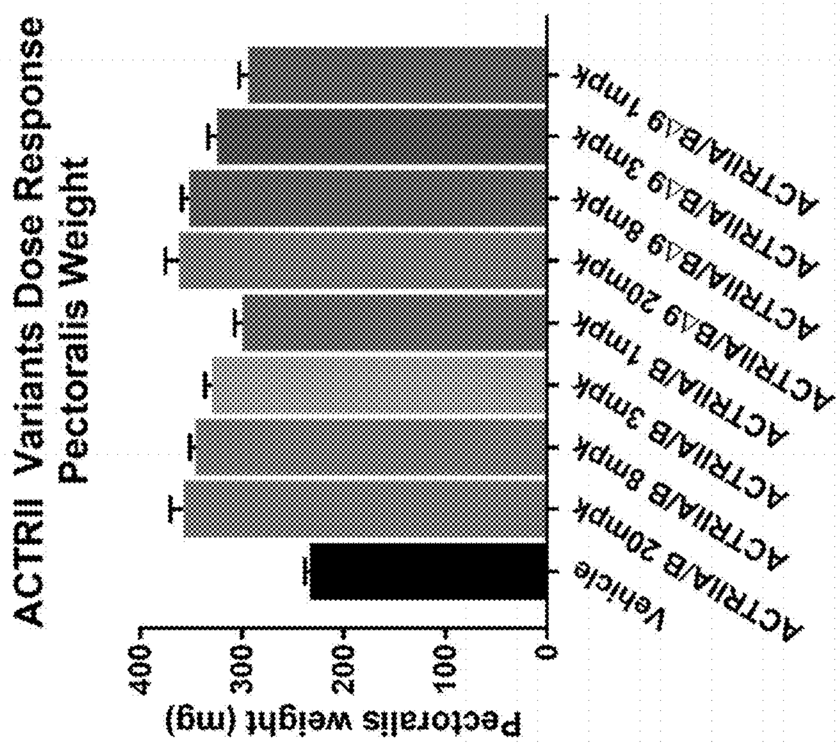
FIGS. 9A and 9B are bar graphs showing the effects of different doses of extracellular ActRIIa variants on muscle weights by tissue analysis.
Figure 9B:
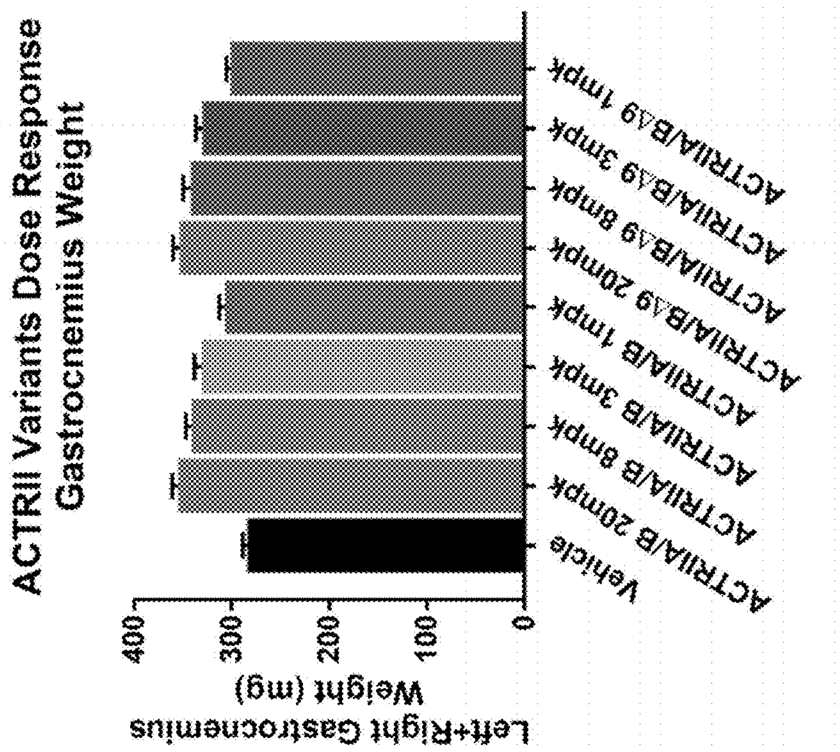

Example 6—Dose Effect of Extracellular ActRIIa Variants on Body Weight, Muscle Weight, and Muscle Mass 8-week old, male C57BL/6 mice were weight-matched into 9 groups (n=10/group). Groups were dosed with 5 mL/kg of either vehicle (Tris-Buffered Saline, pH 7.4) or one of 4 concentrations of ActRIIA/B-Fc (SEQ ID NO: 69 fused to the N-terminus of hFc through a GGG linker) or ActRIIA/BA9-Fc (SEQ ID NO: 58 fused to the N-terminus of hFc through a GGG linker). The doses evaluated were 20 mg/kg, 8 mg/kg, 3 mg/kg and 1 mg/kg. Treatments were administered intraperitoneally (IP) twice a week for 4 weeks (8 doses), and the study was terminated on study day 28. Body weights were recorded on dosing days throughout the study (FIGS. 7A and 7B), and at study termination, groups underwent NMR imaging for lean and fat mass analysis (FIGS. 8A and 8B) and had pectoralis and gastrocnemius muscles weights collected and weighed (FIGS. 9A and 9B).

Example 7—Effect of Extracellular ActRIIa Variants on Obesity

Adult male C57BL/6 mice are assigned to weight-matched treatment groups (n=10/group). All animals are maintained on either regular chow diet (Chow; Purina LabDiet 5001; St. Louis, Mo.) or high fat diet (HFD; Research Diets D12331; New Brunswick, N.J.). Chow- and HFD-fed groups are further divided into groups that are dosed twice weekly with either ActRII variant or vehicle for a period of 60 d. Body weights are measured twice per week at the time of treatment. Body composition is measured using the MiniSpec LF50 at baseline (before administration of treatments and transfer to HFD) and then every other week until the end of the study. At the study termination date, tissues of interest (serum, plasma, muscles and fat depots) are surgically removed and weighed. Serum samples are subsequently evaluated for biomarkers of adiposity and plasma was evaluated for Hba1c levels.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety. Other embodiments are within the following claims.

The invention claimed is:

1. A nucleic acid molecule encoding a polypeptide comprising an extracellular activin receptor type IIa (ActRIIa) variant and an Fc domain, the variant having a sequence of (SEQ ID NO: 1)
$GAILGRSETQECLX_1X_2NANWX_3X_4X_5X_6TNQTGVEX_7CX_8GX_9X_{10}X_{11}X_{12}X_{13}X_{14}HCX_{15}ATWX_{16}NISGSIEIVX_{17}X_{18}GCX_{19}X_{20}X_{21}DX_{22}NCYDRTDCVEX_{23}X_{24}X_{25}X_{26}PX_{27}VYFCCCEGNMCNEKFSYFPEMEVTQPTS$, wherein $X_1$ is F or Y; $X_2$ is Y; $X_3$ is E; $X_4$ is L; $X_5$ is D or E; $X_6$ is R; $X_7$ is P or R; $X_8$ is E; $X_9$ is E; $X_{10}$ is K or Q; $X_{11}$ is D; $X_{12}$ is K; $X_{13}$ is R; $X_{14}$ is L; $X_{15}$ is F or Y; $X_{16}$ is K or R; $X_{17}$ is K; $X_{18}$ is K; $X_{19}$ is W; $X_{20}$ is L; $X_{21}$ is D; $X_{22}$ is I or F; $X_{23}$ is T; $X_{24}$ is K or E; $X_{25}$ is E; $X_{26}$ is N; and $X_{27}$ is Q.

2. The nucleic acid molecule of claim 1, wherein $X_1$ is F and $X_{10}$ is K.

3. The nucleic acid molecule of claim 1, wherein the variant has the sequence of any one of SEQ ID NOs: 6-72.

4. The nucleic acid molecule of claim 1, wherein the polypeptide further comprises a C-terminal extension of one or more amino acids at the C-terminus of the ActRIIa variant.

5. The nucleic acid molecule of claim 4, wherein the C-terminal extension is NP or NPVTPK (SEQ ID NO: 155).

6. The nucleic acid molecule of claim 1, wherein the Fc domain is fused to the C-terminus of the ActRIIa variant by way of a linker.

7. The nucleic acid molecule of claim 1, wherein the variant has the sequence of any one of SEQ ID NOs: 6, 38, 41, 44, 58, 69, 70, 71, and 72.

8. The nucleic acid molecule of claim 1, wherein the variant has the sequence of SEQ ID NO: 69.

9. The nucleic acid molecule of claim 8, wherein the Fc domain is fused to the C-terminus of the ActRIIa variant by way of a linker.

10. A vector comprising the nucleic acid molecule of claim 1.

11. The vector of claim 10, wherein the vector is a viral vector.

12. The vector of claim 11, wherein the viral vector is a retroviral vector, an adenoviral vector, a poxviral vector, an adeno-associated viral vector, or an alphaviral vector.

* * * * *

SEQUENCE LISTING

```
<160> NUMBER OF SEQ ID NOS: 155

<210> SEQ ID NO 1
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Phe or Tyr
<220> FEATURE:
<221> NAME/KEY: MISC_FEATURE
<222> LOCATION: (15)..(15)
<223> OTHER INFORMATION: Xaa is Phe or Tyr
<220> FEATURE:
<221> NAME/KEY: MISC_FEATURE
<222> LOCATION: (20)..(20)
<223> OTHER INFORMATION: Xaa is Glu or Ala
<220> FEATURE:
<221> NAME/KEY: MISC_FEATURE
<222> LOCATION: (21)..(21)
<223> OTHER INFORMATION: Xaa is Lys or Leu
<220> FEATURE:
<221> NAME/KEY: MISC_FEATURE
<222> LOCATION: (22)..(22)
<223> OTHER INFORMATION: Xaa is Asp or Glu
<220> FEATURE:
<221> NAME/KEY: MISC_FEATURE
<222> LOCATION: (23)..(23)
<223> OTHER INFORMATION: Xaa is Arg or Ala
<220> FEATURE:
<221> NAME/KEY: MISC_FEATURE
<222> LOCATION: (31)..(31)
<223> OTHER INFORMATION: Xaa is Pro or Arg
<220> FEATURE:
<221> NAME/KEY: MISC_FEATURE
<222> LOCATION: (33)..(33)
<223> OTHER INFORMATION: Xaa is Tyr or Glu
<220> FEATURE:
<221> NAME/KEY: MISC_FEATURE
<222> LOCATION: (35)..(35)
<223> OTHER INFORMATION: Xaa is Asp or Glu
<220> FEATURE:
<221> NAME/KEY: MISC_FEATURE
<222> LOCATION: (36)..(36)
<223> OTHER INFORMATION: Xaa is Lys or Gln
<220> FEATURE:
<221> NAME/KEY: MISC_FEATURE
<222> LOCATION: (37)..(37)
<223> OTHER INFORMATION: Xaa is Asp or Ala
<220> FEATURE:
<221> NAME/KEY: MISC_FEATURE
<222> LOCATION: (38)..(38)
<223> OTHER INFORMATION: Xaa is Lys or Ala
<220> FEATURE:
<221> NAME/KEY: MISC_FEATURE
<222> LOCATION: (39)..(39)
<223> OTHER INFORMATION: Xaa is Arg or Ala
<220> FEATURE:
<221> NAME/KEY: MISC_FEATURE
<222> LOCATION: (40)..(40)
<223> OTHER INFORMATION: Xaa is Arg or Leu
<220> FEATURE:
<221> NAME/KEY: MISC_FEATURE
<222> LOCATION: (43)..(43)
<223> OTHER INFORMATION: Xaa is Phe or Tyr
<220> FEATURE:
```

```
<221> NAME/KEY: MISC_FEATURE
<222> LOCATION: (47)..(47)
<223> OTHER INFORMATION: Xaa is Lys, Arg, or Ala
<220> FEATURE:
<221> NAME/KEY: MISC_FEATURE
<222> LOCATION: (57)..(57)
<223> OTHER INFORMATION: Xaa is Lys, Ala, Tyr, Phe, or Ile
<220> FEATURE:
<221> NAME/KEY: MISC_FEATURE
<222> LOCATION: (58)..(58)
<223> OTHER INFORMATION: Xaa is Gln or Lys
<220> FEATURE:
<221> NAME/KEY: MISC_FEATURE
<222> LOCATION: (61)..(61)
<223> OTHER INFORMATION: Xaa is Trp or Ala
<220> FEATURE:
<221> NAME/KEY: MISC_FEATURE
<222> LOCATION: (62)..(62)
<223> OTHER INFORMATION: Xaa is Leu or Ala
<220> FEATURE:
<221> NAME/KEY: MISC_FEATURE
<222> LOCATION: (63)..(63)
<223> OTHER INFORMATION: Xaa is Asp, Lys, Arg, Ala, Phe, Gly, Met, Asn,
      or Ile
<220> FEATURE:
<221> NAME/KEY: MISC_FEATURE
<222> LOCATION: (65)..(65)
<223> OTHER INFORMATION: Xaa is Ile, Phe, or Ala
<220> FEATURE:
<221> NAME/KEY: MISC_FEATURE
<222> LOCATION: (76)..(76)
<223> OTHER INFORMATION: Xaa is Lys or Thr
<220> FEATURE:
<221> NAME/KEY: MISC_FEATURE
<222> LOCATION: (77)..(77)
<223> OTHER INFORMATION: Xaa is Lys or Glu
<220> FEATURE:
<221> NAME/KEY: MISC_FEATURE
<222> LOCATION: (78)..(78)
<223> OTHER INFORMATION: Xaa is Asp or Glu
<220> FEATURE:
<221> NAME/KEY: MISC_FEATURE
<222> LOCATION: (79)..(79)
<223> OTHER INFORMATION: Xaa is Ser or Asn
<220> FEATURE:
<221> NAME/KEY: MISC_FEATURE
<222> LOCATION: (81)..(81)
<223> OTHER INFORMATION: Xaa is Glu or Gln

<400> SEQUENCE: 1

Gly Ala Ile Leu Gly Arg Ser Glu Thr Gln Glu Cys Leu Xaa Xaa Asn
1               5                   10                  15

Ala Asn Trp Xaa Xaa Xaa Xaa Thr Asn Gln Thr Gly Val Glu Xaa Cys
            20                  25                  30

Xaa Gly Xaa Xaa Xaa Xaa Xaa Xaa His Cys Xaa Ala Thr Trp Xaa Asn
        35                  40                  45

Ile Ser Gly Ser Ile Glu Ile Val Xaa Xaa Gly Cys Xaa Xaa Xaa Asp
    50                  55                  60

Xaa Asn Cys Tyr Asp Arg Thr Asp Cys Val Glu Xaa Xaa Xaa Xaa Pro
65                  70                  75                  80

Xaa Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 2
<211> LENGTH: 109
<212> TYPE: PRT
<213> ORGANISM: Artificial Sequence
<220> FEATURE:
<223> OTHER INFORMATION: Synthetic Construct
```

<220> FEATURE:
<221> NAME/KEY: MISC_FEATURE
<222> LOCATION: (15)..(15)
<223> OTHER INFORMATION: Xaa is Phe or Tyr
<220> FEATURE:
<221> NAME/KEY: MISC_FEATURE
<222> LOCATION: (20)..(20)
<223> OTHER INFORMATION: Xaa is Glu or Ala
<220> FEATURE:
<221> NAME/KEY: MISC_FEATURE
<222> LOCATION: (21)..(21)
<223> OTHER INFORMATION: Xaa is Lys or Leu
<220> FEATURE:
<221> NAME/KEY: MISC_FEATURE
<222> LOCATION: (22)..(22)
<223> OTHER INFORMATION: Xaa is Asp or Glu
<220> FEATURE:
<221> NAME/KEY: MISC_FEATURE
<222> LOCATION: (23)..(23)
<223> OTHER INFORMATION: Xaa is Arg or Ala
<220> FEATURE:
<221> NAME/KEY: MISC_FEATURE
<222> LOCATION: (31)..(31)
<223> OTHER INFORMATION: Xaa is Pro or Arg
<220> FEATURE:
<221> NAME/KEY: MISC_FEATURE
<222> LOCATION: (33)..(33)
<223> OTHER INFORMATION: Xaa is Tyr or Glu
<220> FEATURE:
<221> NAME/KEY: MISC_FEATURE
<222> LOCATION: (35)..(35)
<223> OTHER INFORMATION: Xaa is Asp or Glu
<220> FEATURE:
<221> NAME/KEY: MISC_FEATURE
<222> LOCATION: (37)..(37)
<223> OTHER INFORMATION: Xaa is Asp or Ala
<220> FEATURE:
<221> NAME/KEY: MISC_FEATURE
<222> LOCATION: (38)..(38)
<223> OTHER INFORMATION: Xaa is Lys or Ala
<220> FEATURE:
<221> NAME/KEY: MISC_FEATURE
<222> LOCATION: (39)..(39)
<223> OTHER INFORMATION: Xaa is Arg or Ala
<220> FEATURE:
<221> NAME/KEY: MISC_FEATURE
<222> LOCATION: (40)..(40)
<223> OTHER INFORMATION: Xaa is Arg or Leu
<220> FEATURE:
<221> NAME/KEY: MISC_FEATURE
<222> LOCATION: (43)..(43)
<223> OTHER INFORMATION: Xaa is Phe or Tyr
<220> FEATURE:
<221> NAME/KEY: MISC_FEATURE
<222> LOCATION: (47)..(47)
<223> OTHER INFORMATION: Xaa is Lys, Arg, or Ala
<220> FEATURE:
<221> NAME/KEY: MISC_FEATURE
<222> LOCATION: (57)..(57)
<223> OTHER INFORMATION: Xaa is Lys, Ala, Tyr, Phe, or Ile
<220> FEATURE:
<221> NAME/KEY: MISC_FEATURE
<222> LOCATION: (58)..(58)
<223> OTHER INFORMATION: Xaa is Gln or Lys
<220> FEATURE:
<221> NAME/KEY: MISC_FEATURE
<222> LOCATION: (61)..(61)
<223> OTHER INFORMATION: Xaa is Trp or Ala
<220> FEATURE:
<221> NAME/KEY: MISC_FEATURE
<222> LOCATION: (62)..(62)
<223> OTHER INFORMATION: Xaa is Leu or Ala
<220> FEATURE:
<221> NAME/KEY: MISC_FEATURE
<222> LOCATION: (63)..(63)
<223> OTHER INFORMATION: Xaa is Asp, Lys, Arg, Ala, Phe, Gly, Met, Asn,
or Ile
<220> FEATURE:
<221> NAME/KEY: MISC_FEATURE

```
<222> LOCATION: (65)..(65)
<223> OTHER INFORMATION: Xaa is Ile, Phe, or Ala
<220> FEATURE:
<221> NAME/KEY: MISC_FEATURE
<222> LOCATION: (76)..(76)
<223> OTHER INFORMATION: Xaa is Lys or Thr
<220> FEATURE:
<221> NAME/KEY: MISC_FEATURE
<222> LOCATION: (77)..(77)
<223> OTHER INFORMATION: Xaa is Lys or Glu
<220> FEATURE:
<221> NAME/KEY: MISC_FEATURE
<222> LOCATION: (78)..(78)
<223> OTHER INFORMATION: Xaa is Asp or Glu
<220> FEATURE:
<221> NAME/KEY: MISC_FEATURE
<222> LOCATION: (79)..(79)
<223> OTHER INFORMATION: Xaa is Ser or Asn
<220> FEATURE:
<221> NAME/KEY: MISC_FEATURE
<222> LOCATION: (81)..(81)
<223> OTHER INFORMATION: Xaa is Glu or Gln

<400> SEQUENCE: 2

Gly Ala Ile Leu Gly Arg Ser Glu Thr Gln Glu Cys Leu Phe Xaa Asn
1               5                   10                  15

Ala Asn Trp Xaa Xaa Xaa Xaa Thr Asn Gln Thr Gly Val Glu Xaa Cys
            20                  25                  30

Xaa Gly Xaa Lys Xaa Xaa Xaa Xaa His Cys Xaa Ala Thr Trp Xaa Asn
        35                  40                  45

Ile Ser Gly Ser Ile Glu Ile Val Xaa Xaa Gly Cys Xaa Xaa Xaa Asp
    50                  55                  60

Xaa Asn Cys Tyr Asp Arg Thr Asp Cys Val Glu Xaa Xaa Xaa Xaa Pro
65                  70                  75                  80

Xaa Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 3
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (15)..(15)
<223> OTHER INFORMATION: Xaa is Phe or Tyr
<220> FEATURE:
<221> NAME/KEY: MISC_FEATURE
<222> LOCATION: (21)..(21)
<223> OTHER INFORMATION: Xaa is Lys or Leu
<220> FEATURE:
<221> NAME/KEY: MISC_FEATURE
<222> LOCATION: (22)..(22)
<223> OTHER INFORMATION: Xaa is Asp or Glu
<220> FEATURE:
<221> NAME/KEY: MISC_FEATURE
<222> LOCATION: (31)..(31)
<223> OTHER INFORMATION: Xaa is Pro or Arg
<220> FEATURE:
<221> NAME/KEY: MISC_FEATURE
<222> LOCATION: (33)..(33)
<223> OTHER INFORMATION: Xaa is Tyr or Glu
<220> FEATURE:
<221> NAME/KEY: MISC_FEATURE
<222> LOCATION: (35)..(35)
<223> OTHER INFORMATION: Xaa is Asp or Glu
<220> FEATURE:
<221> NAME/KEY: MISC_FEATURE
```

```
<222> LOCATION: (40)..(40)
<223> OTHER INFORMATION: Xaa is Arg or Leu
<220> FEATURE:
<221> NAME/KEY: MISC_FEATURE
<222> LOCATION: (43)..(43)
<223> OTHER INFORMATION: Xaa is Phe or Tyr
<220> FEATURE:
<221> NAME/KEY: MISC_FEATURE
<222> LOCATION: (47)..(47)
<223> OTHER INFORMATION: Xaa is Lys, Arg, or Ala
<220> FEATURE:
<221> NAME/KEY: MISC_FEATURE
<222> LOCATION: (58)..(58)
<223> OTHER INFORMATION: Xaa is Gln or Lys
<220> FEATURE:
<221> NAME/KEY: MISC_FEATURE
<222> LOCATION: (65)..(65)
<223> OTHER INFORMATION: Xaa is Ile, Phe, or Ala
<220> FEATURE:
<221> NAME/KEY: MISC_FEATURE
<222> LOCATION: (76)..(76)
<223> OTHER INFORMATION: Xaa is Lys or Thr
<220> FEATURE:
<221> NAME/KEY: MISC_FEATURE
<222> LOCATION: (77)..(77)
<223> OTHER INFORMATION: Xaa is Lys or Glu
<220> FEATURE:
<221> NAME/KEY: MISC_FEATURE
<222> LOCATION: (78)..(78)
<223> OTHER INFORMATION: Xaa is Asp or Glu
<220> FEATURE:
<221> NAME/KEY: MISC_FEATURE
<222> LOCATION: (79)..(79)
<223> OTHER INFORMATION: Xaa is Ser or Asn
<220> FEATURE:
<221> NAME/KEY: MISC_FEATURE
<222> LOCATION: (81)..(81)
<223> OTHER INFORMATION: Xaa is Glu or Gln

<400> SEQUENCE: 3

Gly Ala Ile Leu Gly Arg Ser Glu Thr Gln Glu Cys Leu Phe Xaa Asn
1               5                   10                  15

Ala Asn Trp Glu Xaa Xaa Arg Thr Asn Gln Thr Gly Val Glu Xaa Cys
            20                  25                  30

Xaa Gly Xaa Lys Asp Lys Arg Xaa His Cys Xaa Ala Thr Trp Xaa Asn
        35                  40                  45

Ile Ser Gly Ser Ile Glu Ile Val Lys Xaa Gly Cys Trp Leu Asp Asp
    50                  55                  60

Xaa Asn Cys Tyr Asp Arg Thr Asp Cys Val Glu Xaa Xaa Xaa Xaa Pro
65                  70                  75                  80

Xaa Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 4
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (15)..(15)
<223> OTHER INFORMATION: Xaa is Phe or Tyr
<220> FEATURE:
<221> NAME/KEY: MISC_FEATURE
<222> LOCATION: (21)..(21)
<223> OTHER INFORMATION: Xaa is Lys or Leu
<220> FEATURE:
<221> NAME/KEY: MISC_FEATURE
```

<222> LOCATION: (31)..(31)
<223> OTHER INFORMATION: Xaa is Pro or Arg
<220> FEATURE:
<221> NAME/KEY: MISC_FEATURE
<222> LOCATION: (33)..(33)
<223> OTHER INFORMATION: Xaa is Tyr or Glu
<220> FEATURE:
<221> NAME/KEY: MISC_FEATURE
<222> LOCATION: (35)..(35)
<223> OTHER INFORMATION: Xaa is Asp or Glu
<220> FEATURE:
<221> NAME/KEY: MISC_FEATURE
<222> LOCATION: (40)..(40)
<223> OTHER INFORMATION: Xaa is Arg or Leu
<220> FEATURE:
<221> NAME/KEY: MISC_FEATURE
<222> LOCATION: (43)..(43)
<223> OTHER INFORMATION: Xaa is Phe or Tyr
<220> FEATURE:
<221> NAME/KEY: MISC_FEATURE
<222> LOCATION: (47)..(47)
<223> OTHER INFORMATION: Xaa is Lys, Arg, or Ala
<220> FEATURE:
<221> NAME/KEY: MISC_FEATURE
<222> LOCATION: (58)..(58)
<223> OTHER INFORMATION: Xaa is Gln or Lys
<220> FEATURE:
<221> NAME/KEY: MISC_FEATURE
<222> LOCATION: (65)..(65)
<223> OTHER INFORMATION: Xaa is Ile, Phe, or Ala
<220> FEATURE:
<221> NAME/KEY: MISC_FEATURE
<222> LOCATION: (76)..(76)
<223> OTHER INFORMATION: Xaa is Lys or Thr
<220> FEATURE:
<221> NAME/KEY: MISC_FEATURE
<222> LOCATION: (78)..(78)
<223> OTHER INFORMATION: Xaa is Asp or Glu
<220> FEATURE:
<221> NAME/KEY: MISC_FEATURE
<222> LOCATION: (79)..(79)
<223> OTHER INFORMATION: Xaa is Ser or Asn
<220> FEATURE:
<221> NAME/KEY: MISC_FEATURE
<222> LOCATION: (81)..(81)
<223> OTHER INFORMATION: Xaa is Glu or Gln

<400> SEQUENCE: 4

```
Gly Ala Ile Leu Gly Arg Ser Glu Thr Gln Glu Cys Leu Phe Xaa Asn
1               5                   10                  15

Ala Asn Trp Glu Xaa Asp Arg Thr Asn Gln Thr Gly Val Glu Xaa Cys
            20                  25                  30

Xaa Gly Xaa Lys Asp Lys Arg Xaa His Cys Xaa Ala Thr Trp Xaa Asn
        35                  40                  45

Ile Ser Gly Ser Ile Glu Ile Val Lys Xaa Gly Cys Trp Leu Asp Asp
    50                  55                  60

Xaa Asn Cys Tyr Asp Arg Thr Asp Cys Val Glu Xaa Lys Xaa Xaa Pro
65                  70                  75                  80

Xaa Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 5
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE

```
<222> LOCATION: (15)..(15)
<223> OTHER INFORMATION: Xaa is Phe or Tyr
<220> FEATURE:
<221> NAME/KEY: MISC_FEATURE
<222> LOCATION: (21)..(21)
<223> OTHER INFORMATION: Xaa is Lys or Leu
<220> FEATURE:
<221> NAME/KEY: MISC_FEATURE
<222> LOCATION: (33)..(33)
<223> OTHER INFORMATION: Xaa is Tyr or Glu
<220> FEATURE:
<221> NAME/KEY: MISC_FEATURE
<222> LOCATION: (35)..(35)
<223> OTHER INFORMATION: Xaa is Asp or Glu
<220> FEATURE:
<221> NAME/KEY: MISC_FEATURE
<222> LOCATION: (40)..(40)
<223> OTHER INFORMATION: Xaa is Arg or Leu
<220> FEATURE:
<221> NAME/KEY: MISC_FEATURE
<222> LOCATION: (58)..(58)
<223> OTHER INFORMATION: Xaa is Gln or Lys
<220> FEATURE:
<221> NAME/KEY: MISC_FEATURE
<222> LOCATION: (76)..(76)
<223> OTHER INFORMATION: Xaa is Lys or Thr
<220> FEATURE:
<221> NAME/KEY: MISC_FEATURE
<222> LOCATION: (78)..(78)
<223> OTHER INFORMATION: Xaa is Asp or Glu
<220> FEATURE:
<221> NAME/KEY: MISC_FEATURE
<222> LOCATION: (79)..(79)
<223> OTHER INFORMATION: Xaa is Ser or Asn
<220> FEATURE:
<221> NAME/KEY: MISC_FEATURE
<222> LOCATION: (81)..(81)
<223> OTHER INFORMATION: Xaa is Glu or Gln

<400> SEQUENCE: 5

Gly Ala Ile Leu Gly Arg Ser Glu Thr Gln Glu Cys Leu Phe Xaa Asn
1               5                   10                  15

Ala Asn Trp Glu Xaa Asp Arg Thr Asn Gln Thr Gly Val Glu Pro Cys
            20                  25                  30

Xaa Gly Xaa Lys Asp Lys Arg Xaa His Cys Phe Ala Thr Trp Lys Asn
        35                  40                  45

Ile Ser Gly Ser Ile Glu Ile Val Lys Xaa Gly Cys Trp Leu Asp Asp
    50                  55                  60

Ile Asn Cys Tyr Asp Arg Thr Asp Cys Val Glu Xaa Lys Xaa Xaa Pro
65                  70                  75                  80

Xaa Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 6
<211> LENGTH: 109
<212> TYPE: PRT
<213> ORGANISM: Artificial Sequence
<220> FEATURE:
<223> OTHER INFORMATION: Synthetic Construct

<400> SEQUENCE: 6

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Lys Asn
```

```
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 7
<211> LENGTH: 109
<212> TYPE: PRT
<213> ORGANISM: Artificial Sequence
<220> FEATURE:
<223> OTHER INFORMATION: Synthetic Construct

<400> SEQUENCE: 7

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 8
<211> LENGTH: 109
<212> TYPE: PRT
<213> ORGANISM: Artificial Sequence
<220> FEATURE:
<223> OTHER INFORMATION: Synthetic Construct

<400> SEQUENCE: 8

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 9
<211> LENGTH: 109
```

```
<212> TYPE: PRT
<213> ORGANISM: Artificial Sequence
<220> FEATURE:
<223> OTHER INFORMATION: Synthetic Construct

<400> SEQUENCE: 9

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 10
<211> LENGTH: 109
<212> TYPE: PRT
<213> ORGANISM: Artificial Sequence
<220> FEATURE:
<223> OTHER INFORMATION: Synthetic Construct

<400> SEQUENCE: 10

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 11
<211> LENGTH: 109
<212> TYPE: PRT
<213> ORGANISM: Artificial Sequence
<220> FEATURE:
<223> OTHER INFORMATION: Synthetic Construct

<400> SEQUENCE: 11

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
```

```
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 12
<211> LENGTH: 109
<212> TYPE: PRT
<213> ORGANISM: Artificial Sequence
<220> FEATURE:
<223> OTHER INFORMATION: Synthetic Construct

<400> SEQUENCE: 12

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 13
<211> LENGTH: 109
<212> TYPE: PRT
<213> ORGANISM: Artificial Sequence
<220> FEATURE:
<223> OTHER INFORMATION: Synthetic Construct

<400> SEQUENCE: 13

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 14
<211> LENGTH: 109
<212> TYPE: PRT
<213> ORGANISM: Artificial Sequence
<220> FEATURE:
```

<223> OTHER INFORMATION: Synthetic Construct

<400> SEQUENCE: 14

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 15
<211> LENGTH: 109
<212> TYPE: PRT
<213> ORGANISM: Artificial Sequence
<220> FEATURE:
<223> OTHER INFORMATION: Synthetic Construct

<400> SEQUENCE: 15

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 16
<211> LENGTH: 109
<212> TYPE: PRT
<213> ORGANISM: Artificial Sequence
<220> FEATURE:
<223> OTHER INFORMATION: Synthetic Construct

<400> SEQUENCE: 16

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
```

```
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 17
<211> LENGTH: 109
<212> TYPE: PRT
<213> ORGANISM: Artificial Sequence
<220> FEATURE:
<223> OTHER INFORMATION: Synthetic Construct

<400> SEQUENCE: 17

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 18
<211> LENGTH: 109
<212> TYPE: PRT
<213> ORGANISM: Artificial Sequence
<220> FEATURE:
<223> OTHER INFORMATION: Synthetic Construct

<400> SEQUENCE: 18

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 19
<211> LENGTH: 109
<212> TYPE: PRT
<213> ORGANISM: Artificial Sequence
<220> FEATURE:
<223> OTHER INFORMATION: Synthetic Construct

<400> SEQUENCE: 19
```

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 20
<211> LENGTH: 109
<212> TYPE: PRT
<213> ORGANISM: Artificial Sequence
<220> FEATURE:
<223> OTHER INFORMATION: Synthetic Construct

<400> SEQUENCE: 20

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 21
<211> LENGTH: 109
<212> TYPE: PRT
<213> ORGANISM: Artificial Sequence
<220> FEATURE:
<223> OTHER INFORMATION: Synthetic Construct

<400> SEQUENCE: 21

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
```

```
                85                  90                  95

Ser Tyr Phe Pro Glu Met Glu Val Thr Gln Pro Thr Ser
            100                 105


<210> SEQ ID NO 22
<211> LENGTH: 109
<212> TYPE: PRT
<213> ORGANISM: Artificial Sequence
<220> FEATURE:
<223> OTHER INFORMATION: Synthetic Construct

<400> SEQUENCE: 22

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 23
<211> LENGTH: 109
<212> TYPE: PRT
<213> ORGANISM: Artificial Sequence
<220> FEATURE:
<223> OTHER INFORMATION: Synthetic Construct

<400> SEQUENCE: 23

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 24
<211> LENGTH: 109
<212> TYPE: PRT
<213> ORGANISM: Artificial Sequence
<220> FEATURE:
<223> OTHER INFORMATION: Synthetic Construct

<400> SEQUENCE: 24

Gly Ala Ile Leu Gly Arg Ser Glu Thr Gln Glu Cys Leu Phe Tyr Asn
1               5                   10                  15
```

```
Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 25
<211> LENGTH: 109
<212> TYPE: PRT
<213> ORGANISM: Artificial Sequence
<220> FEATURE:
<223> OTHER INFORMATION: Synthetic Construct

<400> SEQUENCE: 25

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 26
<211> LENGTH: 109
<212> TYPE: PRT
<213> ORGANISM: Artificial Sequence
<220> FEATURE:
<223> OTHER INFORMATION: Synthetic Construct

<400> SEQUENCE: 26

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
```

```
            100                 105


<210> SEQ ID NO 27
<211> LENGTH: 109
<212> TYPE: PRT
<213> ORGANISM: Artificial Sequence
<220> FEATURE:
<223> OTHER INFORMATION: Synthetic Construct

<400> SEQUENCE: 27

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 28
<211> LENGTH: 109
<212> TYPE: PRT
<213> ORGANISM: Artificial Sequence
<220> FEATURE:
<223> OTHER INFORMATION: Synthetic Construct

<400> SEQUENCE: 28

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 29
<211> LENGTH: 109
<212> TYPE: PRT
<213> ORGANISM: Artificial Sequence
<220> FEATURE:
<223> OTHER INFORMATION: Synthetic Construct

<400> SEQUENCE: 29

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30
```

```
Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 30
<211> LENGTH: 109
<212> TYPE: PRT
<213> ORGANISM: Artificial Sequence
<220> FEATURE:
<223> OTHER INFORMATION: Synthetic Construct

<400> SEQUENCE: 30

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 31
<211> LENGTH: 109
<212> TYPE: PRT
<213> ORGANISM: Artificial Sequence
<220> FEATURE:
<223> OTHER INFORMATION: Synthetic Construct

<400> SEQUENCE: 31

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 32
<211> LENGTH: 109
<212> TYPE: PRT
<213> ORGANISM: Artificial Sequence
<220> FEATURE:
<223> OTHER INFORMATION: Synthetic Construct

<400> SEQUENCE: 32

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 33
<211> LENGTH: 109
<212> TYPE: PRT
<213> ORGANISM: Artificial Sequence
<220> FEATURE:
<223> OTHER INFORMATION: Synthetic Construct

<400> SEQUENCE: 33

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 34
<211> LENGTH: 109
<212> TYPE: PRT
<213> ORGANISM: Artificial Sequence
<220> FEATURE:
<223> OTHER INFORMATION: Synthetic Construct

<400> SEQUENCE: 34

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45
```

```
Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 35
<211> LENGTH: 109
<212> TYPE: PRT
<213> ORGANISM: Artificial Sequence
<220> FEATURE:
<223> OTHER INFORMATION: Synthetic Construct

<400> SEQUENCE: 35

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 36
<211> LENGTH: 109
<212> TYPE: PRT
<213> ORGANISM: Artificial Sequence
<220> FEATURE:
<223> OTHER INFORMATION: Synthetic Construct

<400> SEQUENCE: 36

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 37
<211> LENGTH: 109
<212> TYPE: PRT
```

<213> ORGANISM: Artificial Sequence
<220> FEATURE:
<223> OTHER INFORMATION: Synthetic Construct

<400> SEQUENCE: 37

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 38
<211> LENGTH: 109
<212> TYPE: PRT
<213> ORGANISM: Artificial Sequence
<220> FEATURE:
<223> OTHER INFORMATION: Synthetic Construct

<400> SEQUENCE: 38

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 39
<211> LENGTH: 109
<212> TYPE: PRT
<213> ORGANISM: Artificial Sequence
<220> FEATURE:
<223> OTHER INFORMATION: Synthetic Construct

<400> SEQUENCE: 39

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60
```

Phe Asn Cys Tyr Asp Arg Thr Asp Cys Val Glu Thr Lys Glu Asn Pro
65 70 75 80

Gln Val Tyr Phe Cys Cys Cys Glu Gly Asn Met Cys Asn Glu Lys Phe
85 90 95

Ser Tyr Phe Pro Glu Met Glu Val Thr Gln Pro Thr Ser
100 105

<210> SEQ ID NO 40
<211> LENGTH: 109
<212> TYPE: PRT
<213> ORGANISM: Artificial Sequence
<220> FEATURE:
<223> OTHER INFORMATION: Synthetic Construct

<400> SEQUENCE: 40

Gly Ala Ile Leu Gly Arg Ser Glu Thr Gln Glu Cys Leu Phe Tyr Asn
1 5 10 15

Ala Asn Trp Glu Leu Asp Arg Thr Asn Gln Thr Gly Val Glu Arg Cys
20 25 30

Glu Gly Glu Lys Asp Lys Arg Leu His Cys Tyr Ala Thr Trp Lys Asn
35 40 45

Ile Ser Gly Ser Ile Glu Ile Val Lys Lys Gly Cys Trp Leu Asp Asp
50 55 60

Ile Asn Cys Tyr Asp Arg Thr Asp Cys Val Glu Thr Glu Glu Asn Pro
65 70 75 80

Gln Val Tyr Phe Cys Cys Cys Glu Gly Asn Met Cys Asn Glu Lys Phe
85 90 95

Ser Tyr Phe Pro Glu Met Glu Val Thr Gln Pro Thr Ser
100 105

<210> SEQ ID NO 41
<211> LENGTH: 109
<212> TYPE: PRT
<213> ORGANISM: Artificial Sequence
<220> FEATURE:
<223> OTHER INFORMATION: Synthetic Construct

<400> SEQUENCE: 41

Gly Ala Ile Leu Gly Arg Ser Glu Thr Gln Glu Cys Leu Phe Tyr Asn
1 5 10 15

Ala Asn Trp Glu Leu Asp Arg Thr Asn Gln Thr Gly Val Glu Arg Cys
20 25 30

Glu Gly Glu Lys Asp Lys Arg Leu His Cys Phe Ala Thr Trp Arg Asn
35 40 45

Ile Ser Gly Ser Ile Glu Ile Val Lys Lys Gly Cys Trp Leu Asp Asp
50 55 60

Phe Asn Cys Tyr Asp Arg Thr Asp Cys Val Glu Thr Lys Glu Asn Pro
65 70 75 80

Gln Val Tyr Phe Cys Cys Cys Glu Gly Asn Met Cys Asn Glu Lys Phe
85 90 95

Ser Tyr Phe Pro Glu Met Glu Val Thr Gln Pro Thr Ser
100 105

<210> SEQ ID NO 42
<211> LENGTH: 109
<212> TYPE: PRT
<213> ORGANISM: Artificial Sequence
<220> FEATURE:
<223> OTHER INFORMATION: Synthetic Construct

<400> SEQUENCE: 42

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 43
<211> LENGTH: 109
<212> TYPE: PRT
<213> ORGANISM: Artificial Sequence
<220> FEATURE:
<223> OTHER INFORMATION: Synthetic Construct

<400> SEQUENCE: 43

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 44
<211> LENGTH: 109
<212> TYPE: PRT
<213> ORGANISM: Artificial Sequence
<220> FEATURE:
<223> OTHER INFORMATION: Synthetic Construct

<400> SEQUENCE: 44

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80
```

```
Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 45
<211> LENGTH: 109
<212> TYPE: PRT
<213> ORGANISM: Artificial Sequence
<220> FEATURE:
<223> OTHER INFORMATION: Synthetic Construct

<400> SEQUENCE: 45

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 46
<211> LENGTH: 109
<212> TYPE: PRT
<213> ORGANISM: Artificial Sequence
<220> FEATURE:
<223> OTHER INFORMATION: Synthetic Construct

<400> SEQUENCE: 46

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 47
<211> LENGTH: 109
<212> TYPE: PRT
<213> ORGANISM: Artificial Sequence
<220> FEATURE:
<223> OTHER INFORMATION: Synthetic Construct

<400> SEQUENCE: 47
```

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 48
<211> LENGTH: 109
<212> TYPE: PRT
<213> ORGANISM: Artificial Sequence
<220> FEATURE:
<223> OTHER INFORMATION: Synthetic Construct

<400> SEQUENCE: 48

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 49
<211> LENGTH: 109
<212> TYPE: PRT
<213> ORGANISM: Artificial Sequence
<220> FEATURE:
<223> OTHER INFORMATION: Synthetic Construct

<400> SEQUENCE: 49

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95
```

```
Ser Tyr Phe Pro Glu Met Glu Val Thr Gln Pro Thr Ser
            100                 105


<210> SEQ ID NO 50
<211> LENGTH: 109
<212> TYPE: PRT
<213> ORGANISM: Artificial Sequence
<220> FEATURE:
<223> OTHER INFORMATION: Synthetic Construct

<400> SEQUENCE: 50

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 51
<211> LENGTH: 109
<212> TYPE: PRT
<213> ORGANISM: Artificial Sequence
<220> FEATURE:
<223> OTHER INFORMATION: Synthetic Construct

<400> SEQUENCE: 51

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 52
<211> LENGTH: 109
<212> TYPE: PRT
<213> ORGANISM: Artificial Sequence
<220> FEATURE:
<223> OTHER INFORMATION: Synthetic Construct

<400> SEQUENCE: 52

Gly Ala Ile Leu Gly Arg Ser Glu Thr Gln Glu Cys Leu Phe Tyr Asn
1               5                   10                  15
```

```
Ala Asn Trp Glu Leu Glu Arg Thr Asn Gln Thr Gly Val Glu Arg Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 53
<211> LENGTH: 109
<212> TYPE: PRT
<213> ORGANISM: Artificial Sequence
<220> FEATURE:
<223> OTHER INFORMATION: Synthetic Construct

<400> SEQUENCE: 53

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Phe Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 54
<211> LENGTH: 109
<212> TYPE: PRT
<213> ORGANISM: Artificial Sequence
<220> FEATURE:
<223> OTHER INFORMATION: Synthetic Construct

<400> SEQUENCE: 54

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 55
<211> LENGTH: 109
<212> TYPE: PRT
<213> ORGANISM: Artificial Sequence
<220> FEATURE:
<223> OTHER INFORMATION: Synthetic Construct

<400> SEQUENCE: 55

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 56
<211> LENGTH: 109
<212> TYPE: PRT
<213> ORGANISM: Artificial Sequence
<220> FEATURE:
<223> OTHER INFORMATION: Synthetic Construct

<400> SEQUENCE: 56

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 57
<211> LENGTH: 109
<212> TYPE: PRT
<213> ORGANISM: Artificial Sequence
<220> FEATURE:
<223> OTHER INFORMATION: Synthetic Construct

<400> SEQUENCE: 57

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30
```

```
Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 58
<211> LENGTH: 109
<212> TYPE: PRT
<213> ORGANISM: Artificial Sequence
<220> FEATURE:
<223> OTHER INFORMATION: Synthetic Construct

<400> SEQUENCE: 58

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 59
<211> LENGTH: 109
<212> TYPE: PRT
<213> ORGANISM: Artificial Sequence
<220> FEATURE:
<223> OTHER INFORMATION: Synthetic Construct

<400> SEQUENCE: 59

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 60
```

<211> LENGTH: 109
<212> TYPE: PRT
<213> ORGANISM: Artificial Sequence
<220> FEATURE:
<223> OTHER INFORMATION: Synthetic Construct

<400> SEQUENCE: 60

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 61
<211> LENGTH: 109
<212> TYPE: PRT
<213> ORGANISM: Artificial Sequence
<220> FEATURE:
<223> OTHER INFORMATION: Synthetic Construct

<400> SEQUENCE: 61

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 62
<211> LENGTH: 109
<212> TYPE: PRT
<213> ORGANISM: Artificial Sequence
<220> FEATURE:
<223> OTHER INFORMATION: Synthetic Construct

<400> SEQUENCE: 62

```
Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Pro Cys
            20                  25                  30

Glu Gly Glu Lys Asp Lys Arg Leu His Cys Tyr Ala Thr Trp Arg Asn
        35                  40                  45
```

```
Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 63
<211> LENGTH: 109
<212> TYPE: PRT
<213> ORGANISM: Artificial Sequence
<220> FEATURE:
<223> OTHER INFORMATION: Synthetic Construct

<400> SEQUENCE: 63

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Lys Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 64
<211> LENGTH: 109
<212> TYPE: PRT
<213> ORGANISM: Artificial Sequence
<220> FEATURE:
<223> OTHER INFORMATION: Synthetic Construct

<400> SEQUENCE: 64

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Ile Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 65
<211> LENGTH: 109
<212> TYPE: PRT
<213> ORGANISM: Artificial Sequence
```

```
<220> FEATURE:
<223> OTHER INFORMATION: Synthetic Construct

<400> SEQUENCE: 65

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Lys Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 66
<211> LENGTH: 109
<212> TYPE: PRT
<213> ORGANISM: Artificial Sequence
<220> FEATURE:
<223> OTHER INFORMATION: Synthetic Construct

<400> SEQUENCE: 66

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Phe Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 67
<211> LENGTH: 109
<212> TYPE: PRT
<213> ORGANISM: Artificial Sequence
<220> FEATURE:
<223> OTHER INFORMATION: Synthetic Construct

<400> SEQUENCE: 67

Gly Ala Ile Leu Gly Arg Ser Glu Thr Gln Glu Cys Leu Phe Tyr Asn
1               5                   10                  15

Ala Asn Trp Glu Leu Asp Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60
```

Phe Asn Cys Tyr Asp Arg Thr Asp Cys Val Glu Thr Glu Glu Asn Pro
65 70 75 80

Gln Val Tyr Phe Cys Cys Cys Glu Gly Asn Met Cys Asn Glu Lys Phe
85 90 95

Ser Tyr Phe Pro Glu Met Glu Val Thr Gln Pro Thr Ser
100 105

<210> SEQ ID NO 68
<211> LENGTH: 109
<212> TYPE: PRT
<213> ORGANISM: Artificial Sequence
<220> FEATURE:
<223> OTHER INFORMATION: Synthetic Construct

<400> SEQUENCE: 68

Gly Ala Ile Leu Gly Arg Ser Glu Thr Gln Glu Cys Leu Phe Tyr Asn
1 5 10 15

Ala Asn Trp Glu Leu Glu Arg Thr Asn Gln Thr Gly Val Glu Pro Cys
20 25 30

Glu Gly Glu Lys Asp Lys Arg Leu His Cys Tyr Ala Thr Trp Arg Asn
35 40 45

Ile Ser Gly Ser Ile Glu Ile Val Lys Lys Gly Cys Trp Leu Asp Asp
50 55 60

Phe Asn Cys Tyr Asp Arg Thr Asp Cys Val Glu Thr Glu Glu Asn Pro
65 70 75 80

Gln Val Tyr Phe Cys Cys Cys Glu Gly Asn Met Cys Asn Glu Lys Phe
85 90 95

Ser Tyr Phe Pro Glu Met Glu Val Thr Gln Pro Thr Ser
100 105

<210> SEQ ID NO 69
<211> LENGTH: 109
<212> TYPE: PRT
<213> ORGANISM: Artificial Sequence
<220> FEATURE:
<223> OTHER INFORMATION: Synthetic Construct

<400> SEQUENCE: 69

Gly Ala Ile Leu Gly Arg Ser Glu Thr Gln Glu Cys Leu Phe Tyr Asn
1 5 10 15

Ala Asn Trp Glu Leu Glu Arg Thr Asn Gln Thr Gly Val Glu Arg Cys
20 25 30

Glu Gly Glu Lys Asp Lys Arg Leu His Cys Tyr Ala Thr Trp Arg Asn
35 40 45

Ile Ser Gly Ser Ile Glu Ile Val Lys Lys Gly Cys Trp Leu Asp Asp
50 55 60

Phe Asn Cys Tyr Asp Arg Thr Asp Cys Val Glu Thr Glu Glu Asn Pro
65 70 75 80

Gln Val Tyr Phe Cys Cys Cys Glu Gly Asn Met Cys Asn Glu Lys Phe
85 90 95

Ser Tyr Phe Pro Glu Met Glu Val Thr Gln Pro Thr Ser
100 105

<210> SEQ ID NO 70
<211> LENGTH: 109
<212> TYPE: PRT
<213> ORGANISM: Artificial Sequence
<220> FEATURE:
<223> OTHER INFORMATION: Synthetic Construct

<400> SEQUENCE: 70

```
Gly Ala Ile Leu Gly Arg Ser Glu Thr Gln Glu Cys Leu Tyr Tyr Asn
1               5                   10                  15

Ala Asn Trp Glu Leu Glu Arg Thr Asn Gln Thr Gly Val Glu Arg Cys
            20                  25                  30

Glu Gly Glu Gln Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 71
<211> LENGTH: 111
<212> TYPE: PRT
<213> ORGANISM: Artificial Sequence
<220> FEATURE:
<223> OTHER INFORMATION: Synthetic Construct

<400> SEQUENCE: 71

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser Asn Pro
            100                 105                 110
```

<210> SEQ ID NO 72
<211> LENGTH: 115
<212> TYPE: PRT
<213> ORGANISM: Artificial Sequence
<220> FEATURE:
<223> OTHER INFORMATION: Synthetic Construct

<400> SEQUENCE: 72

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80
```

```
Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser Asn Pro Val
            100                 105                 110

Thr Pro Lys
        115


<210> SEQ ID NO 73
<211> LENGTH: 109
<212> TYPE: PRT
<213> ORGANISM: Homo sapiens

<400> SEQUENCE: 73

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 74
<211> LENGTH: 115
<212> TYPE: PRT
<213> ORGANISM: Homo sapiens

<400> SEQUENCE: 74

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115


<210> SEQ ID NO 75
<211> LENGTH: 513
<212> TYPE: PRT
<213> ORGANISM: Homo sapiens

<400> SEQUENCE: 75

Met Gly Ala Ala Ala Lys Leu Ala Phe Ala Val Phe Leu Ile Ser Cys
```

```
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430
```

```
Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu


<210> SEQ ID NO 76
<211> LENGTH: 109
<212> TYPE: PRT
<213> ORGANISM: Artificial Sequence
<220> FEATURE:
<223> OTHER INFORMATION: Synthetic Construct

<400> SEQUENCE: 76

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Ala Asn
        35                  40                  45

Ile Ser Gly Ser Ile Glu Ile Val Lys Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 77
<211> LENGTH: 109
<212> TYPE: PRT
<213> ORGANISM: Artificial Sequence
<220> FEATURE:
<223> OTHER INFORMATION: Synthetic Construct

<400> SEQUENCE: 77

Gly Ala Ile Leu Gly Arg Ser Glu Thr Gln Glu Cys Leu Phe Phe Asn
1               5                   10                  15

Ala Asn Trp Ala Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 78
<211> LENGTH: 109
<212> TYPE: PRT
<213> ORGANISM: Artificial Sequence
<220> FEATURE:
<223> OTHER INFORMATION: Synthetic Construct

<400> SEQUENCE: 78

```
Gly Ala Ile Leu Gly Arg Ser Glu Thr Gln Glu Cys Leu Phe Phe Asn
1               5                   10                  15

Ala Asn Trp Glu Lys Asp Ala Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 79
<211> LENGTH: 109
<212> TYPE: PRT
<213> ORGANISM: Artificial Sequence
<220> FEATURE:
<223> OTHER INFORMATION: Synthetic Construct

<400> SEQUENCE: 79

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Ala Lys Arg Arg His Cys Phe Ala Thr Trp Lys Asn
        35                  40                  45

Ile Ser Gly Ser Ile Glu Ile Val Lys Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 80
<211> LENGTH: 109
<212> TYPE: PRT
<213> ORGANISM: Artificial Sequence
<220> FEATURE:
<223> OTHER INFORMATION: Synthetic Construct

<400> SEQUENCE: 80

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30
```

```
Tyr Gly Asp Lys Asp Ala Arg Arg His Cys Phe Ala Thr Trp Lys Asn
        35                  40                  45

Ile Ser Gly Ser Ile Glu Ile Val Lys Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 81
<211> LENGTH: 109
<212> TYPE: PRT
<213> ORGANISM: Artificial Sequence
<220> FEATURE:
<223> OTHER INFORMATION: Synthetic Construct

<400> SEQUENCE: 81

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Ala Arg His Cys Phe Ala Thr Trp Lys Asn
        35                  40                  45

Ile Ser Gly Ser Ile Glu Ile Val Lys Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 82
<211> LENGTH: 109
<212> TYPE: PRT
<213> ORGANISM: Artificial Sequence
<220> FEATURE:
<223> OTHER INFORMATION: Synthetic Construct

<400> SEQUENCE: 82

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Ala Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 83
```

<211> LENGTH: 109
<212> TYPE: PRT
<213> ORGANISM: Artificial Sequence
<220> FEATURE:
<223> OTHER INFORMATION: Synthetic Construct

<400> SEQUENCE: 83

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Tyr Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 84
<211> LENGTH: 109
<212> TYPE: PRT
<213> ORGANISM: Artificial Sequence
<220> FEATURE:
<223> OTHER INFORMATION: Synthetic Construct

<400> SEQUENCE: 84

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Phe Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 85
<211> LENGTH: 109
<212> TYPE: PRT
<213> ORGANISM: Artificial Sequence
<220> FEATURE:
<223> OTHER INFORMATION: Synthetic Construct

<400> SEQUENCE: 85

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45
```

```
Ile Ser Gly Ser Ile Glu Ile Val Ile Gln Gly Cys Trp Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 86
<211> LENGTH: 109
<212> TYPE: PRT
<213> ORGANISM: Artificial Sequence
<220> FEATURE:
<223> OTHER INFORMATION: Synthetic Construct

<400> SEQUENCE: 86

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Ala Leu Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 87
<211> LENGTH: 109
<212> TYPE: PRT
<213> ORGANISM: Artificial Sequence
<220> FEATURE:
<223> OTHER INFORMATION: Synthetic Construct

<400> SEQUENCE: 87

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Ala Asp Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 88
<211> LENGTH: 109
<212> TYPE: PRT
<213> ORGANISM: Artificial Sequence
```

<220> FEATURE:
<223> OTHER INFORMATION: Synthetic Construct

<400> SEQUENCE: 88

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Lys Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 89
<211> LENGTH: 109
<212> TYPE: PRT
<213> ORGANISM: Artificial Sequence
<220> FEATURE:
<223> OTHER INFORMATION: Synthetic Construct

<400> SEQUENCE: 89

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Arg Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105
```

<210> SEQ ID NO 90
<211> LENGTH: 109
<212> TYPE: PRT
<213> ORGANISM: Artificial Sequence
<220> FEATURE:
<223> OTHER INFORMATION: Synthetic Construct

<400> SEQUENCE: 90

```
Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Ala Asp
    50                  55                  60
```

```
Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 91
<211> LENGTH: 109
<212> TYPE: PRT
<213> ORGANISM: Artificial Sequence
<220> FEATURE:
<223> OTHER INFORMATION: Synthetic Construct

<400> SEQUENCE: 91

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Phe Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 92
<211> LENGTH: 109
<212> TYPE: PRT
<213> ORGANISM: Artificial Sequence
<220> FEATURE:
<223> OTHER INFORMATION: Synthetic Construct

<400> SEQUENCE: 92

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Gly Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 93
<211> LENGTH: 109
<212> TYPE: PRT
<213> ORGANISM: Artificial Sequence
<220> FEATURE:
<223> OTHER INFORMATION: Synthetic Construct
```

```
<400> SEQUENCE: 93

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Met Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 94
<211> LENGTH: 109
<212> TYPE: PRT
<213> ORGANISM: Artificial Sequence
<220> FEATURE:
<223> OTHER INFORMATION: Synthetic Construct

<400> SEQUENCE: 94

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Asn Asp
    50                  55                  60

Ile Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 95
<211> LENGTH: 109
<212> TYPE: PRT
<213> ORGANISM: Artificial Sequence
<220> FEATURE:
<223> OTHER INFORMATION: Synthetic Construct

<400> SEQUENCE: 95

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Ile Asp
    50                  55                  60

Ile Asn Cys Tyr Asp Arg Thr Asp Cys Val Glu Lys Lys Asp Ser Pro
65                  70                  75                  80
```

```
Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 96
<211> LENGTH: 109
<212> TYPE: PRT
<213> ORGANISM: Artificial Sequence
<220> FEATURE:
<223> OTHER INFORMATION: Synthetic Construct

<400> SEQUENCE: 96

Gly Ala Ile Leu Gly Arg Ser Glu Thr Gln Glu Cys Leu Phe Phe Asn
1               5                   10                  15

Ala Asn Trp Glu Lys Asp Arg Thr Asn Gln Thr Gly Val Glu Pro Cys
            20                  25                  30

Tyr Gly Asp Lys Asp Lys Arg Arg His Cys Phe Ala Thr Trp Lys Asn
        35                  40                  45

Ile Ser Gly Ser Ile Glu Ile Val Lys Gln Gly Cys Trp Leu Asp Asp
    50                  55                  60

Ala Asn Cys Tyr Asp Arg Thr Asp Cys Val Glu Lys Lys Asp Ser Pro
65                  70                  75                  80

Glu Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 97
<211> LENGTH: 225
<212> TYPE: PRT
<213> ORGANISM: Homo sapiens

<400> SEQUENCE: 97

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
```

```
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225


<210> SEQ ID NO 98
<211> LENGTH: 4
<212> TYPE: PRT
<213> ORGANISM: Artificial Sequence
<220> FEATURE:
<223> OTHER INFORMATION: Synthetic Construct

<400> SEQUENCE: 98

Gly Gly Gly Ala
1


<210> SEQ ID NO 99
<211> LENGTH: 4
<212> TYPE: PRT
<213> ORGANISM: Artificial Sequence
<220> FEATURE:
<223> OTHER INFORMATION: Synthetic Construct

<400> SEQUENCE: 99

Gly Gly Gly Ser
1


<210> SEQ ID NO 100
<211> LENGTH: 4
<212> TYPE: PRT
<213> ORGANISM: Artificial Sequence
<220> FEATURE:
<223> OTHER INFORMATION: Synthetic Construct

<400> SEQUENCE: 100

Gly Gly Gly Gly
1


<210> SEQ ID NO 101
<211> LENGTH: 5
<212> TYPE: PRT
<213> ORGANISM: Artificial Sequence
<220> FEATURE:
<223> OTHER INFORMATION: Synthetic Construct

<400> SEQUENCE: 101

Gly Gly Gly Gly Ala
1               5


<210> SEQ ID NO 102
<211> LENGTH: 5
<212> TYPE: PRT
<213> ORGANISM: Artificial Sequence
<220> FEATURE:
<223> OTHER INFORMATION: Synthetic Construct

<400> SEQUENCE: 102

Gly Gly Gly Gly Ser
1               5


<210> SEQ ID NO 103
<211> LENGTH: 5
```

<212> TYPE: PRT
<213> ORGANISM: Artificial Sequence
<220> FEATURE:
<223> OTHER INFORMATION: Synthetic Construct

<400> SEQUENCE: 103

Gly Gly Gly Gly Gly
1               5

<210> SEQ ID NO 104
<211> LENGTH: 4
<212> TYPE: PRT
<213> ORGANISM: Artificial Sequence
<220> FEATURE:
<223> OTHER INFORMATION: Synthetic Construct

<400> SEQUENCE: 104

Gly Gly Ala Gly
1

<210> SEQ ID NO 105
<211> LENGTH: 4
<212> TYPE: PRT
<213> ORGANISM: Artificial Sequence
<220> FEATURE:
<223> OTHER INFORMATION: Synthetic Construct

<400> SEQUENCE: 105

Gly Gly Ser Gly
1

<210> SEQ ID NO 106
<211> LENGTH: 4
<212> TYPE: PRT
<213> ORGANISM: Artificial Sequence
<220> FEATURE:
<223> OTHER INFORMATION: Synthetic Construct

<400> SEQUENCE: 106

Ala Gly Gly Gly
1

<210> SEQ ID NO 107
<211> LENGTH: 4
<212> TYPE: PRT
<213> ORGANISM: Artificial Sequence
<220> FEATURE:
<223> OTHER INFORMATION: Synthetic Construct

<400> SEQUENCE: 107

Ser Gly Gly Gly
1

<210> SEQ ID NO 108
<211> LENGTH: 4
<212> TYPE: PRT
<213> ORGANISM: Artificial Sequence
<220> FEATURE:
<223> OTHER INFORMATION: Synthetic Construct

<400> SEQUENCE: 108

Gly Ala Gly Ala
1

<210> SEQ ID NO 109
<211> LENGTH: 4
<212> TYPE: PRT

```
<213> ORGANISM: Artificial Sequence
<220> FEATURE:
<223> OTHER INFORMATION: Synthetic Construct

<400> SEQUENCE: 109

Gly Ser Gly Ser
1


<210> SEQ ID NO 110
<211> LENGTH: 6
<212> TYPE: PRT
<213> ORGANISM: Artificial Sequence
<220> FEATURE:
<223> OTHER INFORMATION: Synthetic Construct

<400> SEQUENCE: 110

Gly Ala Gly Ala Gly Ala
1               5


<210> SEQ ID NO 111
<211> LENGTH: 6
<212> TYPE: PRT
<213> ORGANISM: Artificial Sequence
<220> FEATURE:
<223> OTHER INFORMATION: Synthetic Construct

<400> SEQUENCE: 111

Gly Ser Gly Ser Gly Ser
1               5


<210> SEQ ID NO 112
<211> LENGTH: 8
<212> TYPE: PRT
<213> ORGANISM: Artificial Sequence
<220> FEATURE:
<223> OTHER INFORMATION: Synthetic Construct

<400> SEQUENCE: 112

Gly Ala Gly Ala Gly Ala Gly Ala
1               5


<210> SEQ ID NO 113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 113

Gly Ser Gly Ser Gly Ser Gly Ser
1               5


<210> SEQ ID NO 114
<211> LENGTH: 10
<212> TYPE: PRT
<213> ORGANISM: Artificial Sequence
<220> FEATURE:
<223> OTHER INFORMATION: Synthetic Construct

<400> SEQUENCE: 114

Gly Ala Gly Ala Gly Ala Gly Ala Gly Ala
1               5                   10


<210> SEQ ID NO 115
<211> LENGTH: 10
<212> TYPE: PRT
<213> ORGANISM: Artificial Sequence
```

<220> FEATURE:
<223> OTHER INFORMATION: Synthetic Construct

<400> SEQUENCE: 115

Gly Ser Gly Ser Gly Ser Gly Ser Gly Ser
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic Construct

<400> SEQUENCE: 116

Gly Ala Gly Ala Gly Ala Gly Ala Gly Ala Gly Ala
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthetic Construct

<400> SEQUENCE: 117

Gly Ser Gly Ser Gly Ser Gly Ser Gly Ser Gly Ser
1               5                   10

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct

<400> SEQUENCE: 118

Gly Gly Ala Gly Gly Ala
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic Construct

<400> SEQUENCE: 119

Gly Gly Ser Gly Gly Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Construct

<400> SEQUENCE: 120

Gly Gly Ala Gly Gly Ala Gly Gly Ala
1               5

<210> SEQ ID NO 121
<211> LENGTH: 9
<212> TYPE: PRT
<213> ORGANISM: Artificial Sequence
<220> FEATURE:

<223> OTHER INFORMATION: Synthetic Construct

<400> SEQUENCE: 121

Gly Gly Ser Gly Gly Ser Gly Gly Ser
1 5

<210> SEQ ID NO 122
<211> LENGTH: 12
<212> TYPE: PRT
<213> ORGANISM: Artificial Sequence
<220> FEATURE:
<223> OTHER INFORMATION: Synthetic Construct

<400> SEQUENCE: 122

Gly Gly Ala Gly Gly Ala Gly Gly Ala Gly Gly Ala
1 5 10

<210> SEQ ID NO 123
<211> LENGTH: 12
<212> TYPE: PRT
<213> ORGANISM: Artificial Sequence
<220> FEATURE:
<223> OTHER INFORMATION: Synthetic Construct

<400> SEQUENCE: 123

Gly Gly Ser Gly Gly Ser Gly Gly Ser Gly Gly Ser
1 5 10

<210> SEQ ID NO 124
<211> LENGTH: 8
<212> TYPE: PRT
<213> ORGANISM: Artificial Sequence
<220> FEATURE:
<223> OTHER INFORMATION: Synthetic Construct

<400> SEQUENCE: 124

Gly Gly Ala Gly Gly Gly Ala Gly
1 5

<210> SEQ ID NO 125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 125

Gly Gly Ser Gly Gly Gly Ser Gly
1 5

<210> SEQ ID NO 126
<211> LENGTH: 12
<212> TYPE: PRT
<213> ORGANISM: Artificial Sequence
<220> FEATURE:
<223> OTHER INFORMATION: Synthetic Construct

<400> SEQUENCE: 126

Gly Gly Ala Gly Gly Gly Ala Gly Gly Gly Ala Gly
1 5 10

<210> SEQ ID NO 127
<211> LENGTH: 12
<212> TYPE: PRT
<213> ORGANISM: Artificial Sequence
<220> FEATURE:
<223> OTHER INFORMATION: Synthetic Construct

<400> SEQUENCE: 127

Gly Gly Ser Gly Gly Gly Ser Gly Gly Gly Ser Gly
1 5 10

<210> SEQ ID NO 128
<211> LENGTH: 15
<212> TYPE: PRT
<213> ORGANISM: Artificial Sequence
<220> FEATURE:
<223> OTHER INFORMATION: Synthetic Construct

<400> SEQUENCE: 128

Gly Gly Gly Gly Ala Gly Gly Gly Gly Ala Gly Gly Gly Gly Ala
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: Synthetic Construct

<400> SEQUENCE: 129

Gly Gly Gly Gly Ser Gly Gly Gly Gly Ser Gly Gly Gly Gly Ser
1 5 10 15

<210> SEQ ID NO 130
<211> LENGTH: 5
<212> TYPE: PRT
<213> ORGANISM: Artificial Sequence
<220> FEATURE:
<223> OTHER INFORMATION: Synthetic Construct

<400> SEQUENCE: 130

Gly Gly Gly Ala Gly
1 5

<210> SEQ ID NO 131
<211> LENGTH: 6
<212> TYPE: PRT
<213> ORGANISM: Artificial Sequence
<220> FEATURE:
<223> OTHER INFORMATION: Synthetic Construct

<400> SEQUENCE: 131

Gly Gly Gly Ala Gly Gly
1 5

<210> SEQ ID NO 132
<211> LENGTH: 7
<212> TYPE: PRT
<213> ORGANISM: Artificial Sequence
<220> FEATURE:
<223> OTHER INFORMATION: Synthetic Construct

<400> SEQUENCE: 132

Gly Gly Gly Ala Gly Gly Gly
1 5

<210> SEQ ID NO 133
<211> LENGTH: 4
<212> TYPE: PRT
<213> ORGANISM: Artificial Sequence
<220> FEATURE:
<223> OTHER INFORMATION: Synthetic Construct

<400> SEQUENCE: 133

Ala Ala Ala Leu
1

<210> SEQ ID NO 134
<211> LENGTH: 4
<212> TYPE: PRT
<213> ORGANISM: Artificial Sequence
<220> FEATURE:
<223> OTHER INFORMATION: Synthetic Construct

<400> SEQUENCE: 134

Ala Ala Ala Lys
1

<210> SEQ ID NO 135
<211> LENGTH: 4
<212> TYPE: PRT
<213> ORGANISM: Artificial Sequence
<220> FEATURE:
<223> OTHER INFORMATION: Synthetic Construct

<400> SEQUENCE: 135

Ala Ala Ala Arg
1

<210> SEQ ID NO 136
<211> LENGTH: 14
<212> TYPE: PRT
<213> ORGANISM: Artificial Sequence
<220> FEATURE:
<223> OTHER INFORMATION: Synthetic Construct

<400> SEQUENCE: 136

Glu Gly Lys Ser Ser Gly Ser Gly Ser Glu Ser Lys Ser Thr
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic Construct

<400> SEQUENCE: 137

Gly Ser Ala Gly Ser Ala Ala Gly Ser Gly Glu Phe
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic Construct

<400> SEQUENCE: 138

Ala Glu Ala Ala Ala Lys Glu Ala Ala Ala Lys Ala
1               5                   10

<210> SEQ ID NO 139
<211> LENGTH: 18
<212> TYPE: PRT
<213> ORGANISM: Artificial Sequence
<220> FEATURE:
<223> OTHER INFORMATION: Synthetic Construct

<400> SEQUENCE: 139

Lys Glu Ser Gly Ser Val Ser Ser Glu Gln Leu Ala Gln Phe Arg Ser
1 5 10 15

Leu Asp

<210> SEQ ID NO 140
<211> LENGTH: 10
<212> TYPE: PRT
<213> ORGANISM: Artificial Sequence
<220> FEATURE:
<223> OTHER INFORMATION: Synthetic Construct

<400> SEQUENCE: 140

Gly Glu Asn Leu Tyr Phe Gln Ser Gly Gly
1 5 10

<210> SEQ ID NO 141
<211> LENGTH: 8
<212> TYPE: PRT
<213> ORGANISM: Artificial Sequence
<220> FEATURE:
<223> OTHER INFORMATION: Synthetic Construct

<400> SEQUENCE: 141

Ser Ala Cys Tyr Cys Glu Leu Ser
1 5

<210> SEQ ID NO 142
<211> LENGTH: 5
<212> TYPE: PRT
<213> ORGANISM: Artificial Sequence
<220> FEATURE:
<223> OTHER INFORMATION: Synthetic Construct

<400> SEQUENCE: 142

Arg Ser Ile Ala Thr
1 5

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Arg Pro Ala Cys Lys Ile Pro Asn Asp Leu Lys Gln Lys Val Met Asn
1 5 10 15

His

<210> SEQ ID NO 144
<211> LENGTH: 36
<212> TYPE: PRT
<213> ORGANISM: Artificial Sequence
<220> FEATURE:
<223> OTHER INFORMATION: Synthetic Construct

<400> SEQUENCE: 144

Gly Gly Ser Ala Gly Gly Ser Gly Ser Gly Ser Ser Gly Gly Ser Ser
1 5 10 15

Gly Ala Ser Gly Thr Gly Thr Ala Gly Gly Thr Gly Ser Gly Ser Gly
20 25 30

Thr Gly Ser Gly
35

<210> SEQ ID NO 145
<211> LENGTH: 17
<212> TYPE: PRT
<213> ORGANISM: Artificial Sequence
<220> FEATURE:
<223> OTHER INFORMATION: Synthetic Construct

<400> SEQUENCE: 145

Ala Ala Ala Asn Ser Ser Ile Asp Leu Ile Ser Val Pro Val Asp Ser
1 5 10 15

Arg

<210> SEQ ID NO 146
<211> LENGTH: 36
<212> TYPE: PRT
<213> ORGANISM: Artificial Sequence
<220> FEATURE:
<223> OTHER INFORMATION: Synthetic Construct

<400> SEQUENCE: 146

Gly Gly Ser Gly Gly Gly Ser Glu Gly Gly Gly Ser Glu Gly Gly Gly
1 5 10 15

Ser Glu Gly Gly Gly Ser Glu Gly Gly Gly Ser Glu Gly Gly Gly Ser
20 25 30

Gly Gly Gly Ser
35

<210> SEQ ID NO 147
<211> LENGTH: 5
<212> TYPE: PRT
<213> ORGANISM: Artificial Sequence
<220> FEATURE:
<223> OTHER INFORMATION: Synthetic Construct

<400> SEQUENCE: 147

Glu Ala Ala Ala Lys
1 5

<210> SEQ ID NO 148
<211> LENGTH: 5
<212> TYPE: PRT
<213> ORGANISM: Artificial Sequence
<220> FEATURE:
<223> OTHER INFORMATION: Synthetic Construct

<400> SEQUENCE: 148

Pro Ala Pro Ala Pro
1 5

<210> SEQ ID NO 149
<211> LENGTH: 115
<212> TYPE: PRT
<213> ORGANISM: Artificial Sequence
<220> FEATURE:
<223> OTHER INFORMATION: Synthetic Construct

<400> SEQUENCE: 149

Gly Arg Gly Glu Ala Glu Thr Arg Glu Cys Ile Phe Tyr Asn Ala Asn
1 5 10 15

Trp Glu Lys Asp Arg Thr Asn Gln Ser Gly Leu Glu Pro Cys Tyr Gly
20 25 30

Asp Gln Asp Lys Arg Arg His Cys Phe Ala Ser Trp Lys Asn Ser Ser
35 40 45

```
Gly Thr Ile Glu Leu Val Lys Gln Gly Cys Trp Leu Asp Asp Ile Asn
    50                  55                  60

Cys Tyr Asp Arg Gln Glu Cys Val Ala Lys Lys Asp Ser Pro Glu Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115


<210> SEQ ID NO 150
<211> LENGTH: 109
<212> TYPE: PRT
<213> ORGANISM: Artificial Sequence
<220> FEATURE:
<223> OTHER INFORMATION: Synthetic Construct

<400> SEQUENCE: 150

Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Arg Cys
            20                  25                  30

Glu Gly Glu Lys Asp Lys Arg Leu His Cys Tyr Ala Thr Trp Arg Asn
        35                  40                  45

Ile Ser Gly Ser Ile Glu Ile Val Ala Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 151
<211> LENGTH: 246
<212> TYPE: PRT
<213> ORGANISM: Homo sapiens

<400> SEQUENCE: 151

Met Glu Trp Ser Trp Val Phe Leu Phe Phe Leu Ser Val Thr Thr Gly
1               5                   10                  15

Val His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
```

```
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245


<210> SEQ ID NO 152
<211> LENGTH: 11
<212> TYPE: PRT
<213> ORGANISM: Artificial Sequence
<220> FEATURE:
<223> OTHER INFORMATION: Synthetic Construct

<400> SEQUENCE: 152

Asp Ile Cys Leu Pro Arg Trp Gly Cys Leu Trp
1               5                   10


<210> SEQ ID NO 153
<211> LENGTH: 93
<212> TYPE: PRT
<213> ORGANISM: Homo sapiens

<400> SEQUENCE: 153

Gly Pro Val Glu Val Phe Ile Thr Glu Thr Pro Ser Gln Pro Asn Ser
1               5                   10                  15

His Pro Ile Gln Trp Asn Ala Pro Gln Pro Ser His Ile Ser Lys Tyr
            20                  25                  30

Ile Leu Arg Trp Arg Pro Lys Asn Ser Val Gly Arg Trp Lys Glu Ala
        35                  40                  45

Thr Ile Pro Gly His Leu Asn Ser Tyr Thr Ile Lys Gly Leu Lys Pro
    50                  55                  60

Gly Val Val Tyr Glu Gly Gln Leu Ile Ser Ile Gln Gln Tyr Gly His
65                  70                  75                  80

Gln Glu Val Thr Arg Phe Asp Phe Thr Thr Thr Ser Thr
                85                  90


<210> SEQ ID NO 154
<211> LENGTH: 609
<212> TYPE: PRT
<213> ORGANISM: Homo sapiens

<400> SEQUENCE: 154

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45
```

```
Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
```

-continued 465 470 475 480

Leu Asn Gln Leu Cys Val Leu His Glu Lys Thr Pro Val Ser Asp Arg
485 490 495

Val Thr Lys Cys Cys Thr Glu Ser Leu Val Asn Arg Arg Pro Cys Phe
500 505 510

Ser Ala Leu Glu Val Asp Glu Thr Tyr Val Pro Lys Glu Phe Asn Ala
515 520 525

Glu Thr Phe Thr Phe His Ala Asp Ile Cys Thr Leu Ser Glu Lys Glu
530 535 540

Arg Gln Ile Lys Lys Gln Thr Ala Leu Val Glu Leu Val Lys His Lys
545 550 555 560

Pro Lys Ala Thr Lys Glu Gln Leu Lys Ala Val Met Asp Asp Phe Ala
565 570 575

Ala Phe Val Glu Lys Cys Cys Lys Ala Asp Asp Lys Glu Thr Cys Phe
580 585 590

Ala Glu Glu Gly Lys Lys Leu Val Ala Ala Ser Gln Ala Ala Leu Gly
595 600 605

Leu

<210> SEQ ID NO 155
<211> LENGTH: 6
<212> TYPE: PRT
<213> ORGANISM: Homo sapiens

<400> SEQUENCE: 155

Asn Pro Val Thr Pro Lys
1 5